United States Patent [19]
Went

[11] Patent Number: 6,150,179
[45] Date of Patent: *Nov. 21, 2000

[54] METHOD OF USING SOLID STATE NMR TO MEASURE DISTANCES BETWEEN NUCLEI IN COMPOUNDS ATTACHED TO A SURFACE

[75] Inventor: Gregory T. Went, Madison, Conn.

[73] Assignee: Curagen Corporation, Branford, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/678,735

[22] Filed: Jul. 11, 1996

Related U.S. Application Data

[62] Division of application No. 08/418,992, Mar. 31, 1995.

[51] Int. Cl.$^7$ .................................................. G01N 24/00
[52] U.S. Cl. ........................................... 436/173; 425/7.1
[58] Field of Search ........................... 435/7.2; 364/496, 364/497, 500; 436/173, 518, 527, 528

[56] References Cited

U.S. PATENT DOCUMENTS

| | | |
|---|---|---|
| 5,225,533 | 7/1993 | Rutter et al. . |
| 5,241,470 | 8/1993 | Lee et al. . |
| 5,252,743 | 10/1993 | Barrett et al. . |
| 5,265,030 | 11/1993 | Skolnick et al. . |
| 5,270,170 | 12/1993 | Schatz et al. . |
| 5,307,287 | 4/1994 | Cramer, III et al. . |
| 5,331,573 | 7/1994 | Balaji et al. . |

FOREIGN PATENT DOCUMENTS

| | | |
|---|---|---|
| WO 91/05058 | 4/1991 | WIPO . |
| WO 93/08278 | 4/1993 | WIPO . |
| WO 93/10214 | 5/1993 | WIPO . |
| WO 93/17032 | 9/1993 | WIPO . |
| WO 93/20242 | 10/1993 | WIPO . |
| WO 94/18318 | 8/1994 | WIPO . |

OTHER PUBLICATIONS

Rizo et al, Jrnl. of Ace Am. Chem. Soc., vol. 114, pp. 2852–2859 (1992).
Sindorf, J. Am. Chem. Soc., vol. 105, pp. 1848–1851, (1983).
Faicchinin et al, Macromolecules, vol. 17, pp. 2405–2411, (1984).
Blum et al, Polymer Preprints, Am. Chem. Soc., vol. 29(1), pp. 54–55 (1988).
Agouon Corp., Press Release, dated Apr. 1994.
Alberg and Shreiber, 1993, Structure–Based Design of a Cyclophilin–Calcineurin Bridging Ligand, *Science* 262:248–250.
Anglister et al., 1993, "Recent Advances in the Study of Isotopically Enriched Proteins", *Frontiers of NMR in Molecular Biology III*, paper LZ011.
Arkin and Youvan, 1992, "Optimizing Nucleotide Mixtures to Encode Specific Subsets of Amino Acids for Semi–Random Mutagenesis", *Bio/Technology 10*: 297–300.

Benner, Steven A., 1994," Expanding the genetic lexicon: Incorporating non–standard amino acids into proteins by ribosome–based synthesis", *Trend. BioTech. 12*: 158–162.
Biosym Technologies, 1994, *Discover® User Guide*, Chapter 1: 1.1–1.6.
Biosym Technologies, 1993, *Insight II® User Guide*, Chapter 1: 1.1–1.39 and Chapter 4: 4.1–4.76.
Brenner and Lerner, 1992, "Encoded combinatorial chemistry," *Proc. Natl. Acad. Sci.* USA 89:5381–5383.
Brunger and Karplus, 1991, "Molecular Dynamics Simulations with Experimental Restraints", *Acc. Chem. Res. 24*: 54–61.
Bunin et al., 1994, "The combinatorial synthesis and chemical and biological evaluation of a 1,4–benzodiazepine library", *Proc. Natl. Acad. Sci.* USA 91:4708–4712.
Campbell and Downing, 1994," Building protein structure and function from modular units", *Trend. BioTech. 12*: 168–72.
Cane and Yang, 1984, "Biosynthetic Origin of the Carbon Skeleton and Oxygen Atoms of Nargenicin $A_1$" *J. Am. Chem. Soc. 106*: 784–787.
Cantor and Schimmel, 1980, *Biophysical Chemistry Part I: The Conformation of Biological Macromolecules* (New York, W.H. Freeman and Co.), pp. 253–279.
Carpino and Han, 1970, "The 9–Fluorenylmethoxycarbonyl Function, a New Base–Sensitive Amino–Protecting Group", *J. Amer. Chem. Soc. 85*: 5748–5749.
Chandler, David, 1991, "Course 4: Theory of Quantum Processes in Liquids", pp. 194–285, as found in *Liquides, Cristallisation et Transition Vitreuse*, Hansen, Levesque and Zinn–Justin, eds., (Elsevier Science Publishers, New York).
Clackson and Wells, 1994, "In vitro selection from protein and peptide libraries", *Trend. BioTech. 12*: 173–184.
Clore and Gronenborn, 1991, "Comparison of the Solution Nuclear Magnetic Resonance and X–Ray Crystal Structures of Human Recombinant Interleukin–1β", *J. Mol. Biol.*, 221: 47–53.
Cook and McCormick, 1994, "Ras blooms on sterile ground", *Nature 369*: 361–362.
Cornish et al., 1994, "Site–specific incorporation of biophysical probes into proteins", *Proc. Natl. Acad. Sci. USA 91*: 2910–2914.
Creuzet et al., 1991, "Determination of Membrane Protein Structure by Rotational Resonance NMR: Bacteriorhodopsin", *Science 251*:783–786.

(List continued on next page.)

*Primary Examiner*—Ponnathapura Achutamurthy
*Assistant Examiner*—Joseph W. Ricigliano
*Attorney, Agent, or Firm*—Pennie & Edmonds LLP

[57] ABSTRACT

The present method provides for a method of conducting solid state NMR distance measurements between nuclei in compounds attached to a surface. In specific embodiments the measurements are made by rotational echo double resonance (REDOR). Other embodiments are directed to the use of the method wherein the distances measurements involve peptides.

20 Claims, 21 Drawing Sheets

Microfiche Appendix Included
(2 Microfiche, 101 Pages)

OTHER PUBLICATIONS

Cull et al., 1992, "Screening for receptor ligands using large libraries of peptides linked to the C terminus of the lac repressor," *Proc. Natl. Acad. Sci. USA 89*: 1865–1869.

Dodd et al., 1993, "A concerted rotation algorithm for atomistic Monte Carlo simulation of polymer melts and glasses", *Molecular Phys. 78*: 961–996.

Erb et al., 1994, "Recursive deconvolution of combinatorial chemical libraries," *Proc. Natl. Acad. Sci. USA 91*: 11422–11426.

Fields and Song, 1989, "A novel genetic system to detect protein—protein interactions" *Nature 340*: 245–246.

Fowlkes et al,. 1992, "Multipurpose vectors for peptide expression on the M13 viral surface," *BioTechniques* 13(3): 422–427.

Garbow and McWherter, 1993, "Determination of the molecular conformation of melanostatin using $^{13}C$, $^{15}N$–REDOR NMR spectroscopy", *J. Am. Chem. Soc.* 115:238–44.

Gerstein et al., 1985, *Transient Techniques in NMR of Solids* (Academic Press, New York) Chapters 5–6, pp. 164–275.

Goldman and Youvan, 1994, "An Algorithmically Optimized Combinatorial Library Screened by Digital Imaging Spectroscopy", *Bio/Technology 10*: 1557–1561.

Goldstein, 1950, *Classical Mechanics* (Addison–Wesley, Reading, MA) chap. 4, pp. 91–142.

Gordon and Somorjai, 1992, "Fuzzy cluster analysis of molecular dynamics trajectories", *Proteins: Structure, Function, and Genetics 14*: 249–264.

Gullion and Schaefer, 1989, "Rotational–echo double–resonance NMR", *J. Magnetic Resonance 81*: 196–200.

Hall, 1994, "A Biochemical Function for Ras– At Last" *Science*, 264: 1413–14.

Hao et al., 1994, "Statistical Thermodynamics of Protein Folding: Sequence Dependence", *J. Phys. Chem.*, 98: 9882–9893.

Holl et al., 1992, "Determination of an 8–Å Interatomic Distance in a Helical Peptide by Solid–State NMR Spectroscopy", *J. Amer. Chem. Soc. 114*: 4830–4833.

Holl et al, 1990, "Rotational–Echo Triple–Resonance NMR", *J. Magnetic Resonance 81*: 620–626.

Holzman, 1994, " Protein Folding", *American Scientist 82*: 267–274.

Ibba and Hennecke, 1994, "Towards Engineering Proteins by Site–Directed Incorporation In Vivo of Non–Natural Amino Acids", *Bio/Technology 12*: 678682.

Jayawickreme et al., 1994, "Creation and functional screening of a multi–use peptide library," *Proc. Natl. Acad. Sci. USA 91*: 1614–1618.

Kay et al., 1993, "An M13 phage library displaying random 38–amino–acid peptides as a source of novel sequences with affinity to selected targets," *Gene 128*: 59–65.

Kolbert et al., 1994, "Measurement of internuclear distance by switch angle spinning NMR", *J. Phys. Chem. 98*: 7936–7938.

Korman et al., 1982, "cDNA clones for the heavy chain of HLA–DR antigens obtained after immunopurification of polysomes by monoclonal antibody," *Proc. Natl. Acad. Sci. USA 79*: 1844–1848.

Kraus and Rosenberg, 1982, "Purification of low–abundance messenger RNAs from rat liver by polysome immunoadsorption," *Proc. Natl. Acad. Sci. USA 79*: 4015–4019.

Lehninger, 1982, *Principles of Biochemistry* (Worth Publishers, New York) pp. 100–103.

Lesley et al., 1991, "Use of in Vitro Protein Synthesis from Polymerase Chain Reaction–generated Templates to Study Interaction of *Escherichia coli* Transcription Factors with Core RNA Polymerase and for Epitope Mapping of Monoclonal Antibodies," *J. Biol. Chem.* 266(4): 2632–2638.

MacArthur et al., 1994, "NMR and crystallography–complementary approaches to structure determination", *Trend. BioTech. 12*: 149–153.

Marengere et al., 1994, "SH2 domain specificity and activity modified by a single residue", *Nature 369*: 502–505.

Marks et al., 1993, 'Human antibody fragments specific for human blood group antigens from a phage display library, *Bio/Technology 11*: 1145–1149.

Martin, Yvonne C., 1992, "3D Database Searching in Drug Design," *Journal of Medicinal Chemistry 35*: 2145–2154.

Mattheakis et al., 1994, "An in vitro polysome display system for identifying ligands from very large peptide libraries," *Proc. Natl. Acad. Sci. USA 91*: 9022–9026.

McDowell et al., 1994, "From Peptide to non–peptide. I. The elucidation of a bioactive confirmation for the arginine–glycine–aspartic acid recognition sequence", *J. Am. Chem. Soc. 116*: 5069–5076.

Merrifield, 1963, "Solid Phase Peptide Synthesis. I. The Synthesis of a Tetrapeptide", *J. Amer. Chem. Soc. 85*: 2149–2154.

Mueller, 1995, "Analytic solutions for the time–evolution of dipolar–dephasing NMR signals", *J. Magnetic Resonance*, Ser. A, in press.

Murphy, et al., 1993, "Large–Scale Synthesis of Triple Helix Forming Oligonucleotides Using a controlled–Pore Glass Support", *BioTechniques 15*: 1004–1010.

Nikiforovich, Gregory, V., 1994, "Computational molecular modeling in peptide drug design", *International Journal of Peptide & Protein Research 44*: 513–531.

Ohlmeyer et al., 1993, "Complex synthetic chemical libraries indexed with molecular tags," *Proc. Natl. Acad. Sci. USA 90*: 10922–10926.

Olivera et al., 1990, "Diversity of Conus Neuropeptides", *Science 249*: 257–263.

Ostresh et al., 1994, "'Libraries from libraries': chemical transformation of combinatorial libraries to extend the range and repertoire of chemical diversity," *Proc. Natl. Acad. Sci. USA 91*: 11138–11142.

Pan et al., 1990, "Determination of C—N internuclear distance by rotational–echo double–resonance NMR of solids", *J. Magnetic Resonance 90*: 330–340.

Press et al., 1986, *Numerical Recipes: the Art of Scientific Computing* (Cambridge University Press, Cambridge, U.K.) pp. 102–115, 170–176, 191–209, 240–259, and 274–289.

Raleigh et al., 1988 "Rotational Resonance in Solid State NMR", *Chem. Phys. Letts. 146*: 71–76.

Ross, Russell, 1993, The pathogenesis of atherosclerosis: a perspective for the 1990's , *Nature 362*: 801–809.

Rothberg and Artavanis–Tsakonis, 1992, "Modularity of the Slit Protein", *J. Mol. Biol.*, 227: 367–370.

Rowley, 1994, *Statistical Mechanics for Thermophysical Property Calculations* (PTR Prentice Hall, Englewood Cliffs, N.J.) pp. 215–279.

Salmon et al., 1993, "Discovery of biologically active peptides in random libraries: solution–phase testing after staged orthogonal release from resin beads," *Proc. Natl. Acad. Sci. USA 90*: 11708–11712.

Shaanen et al., 1992, "Combining Experimental Information from Crystal and Solution Studies: joint X–ray and NMR Refinement", *Science*, 257:961–964.

Shenkin et al., 1987, "Predicting antibody hypervariable loop conformation. I. Ensembles of Random Conformations for Ringlike Structures", *Biopolymers* 26:2053–2085.

Siepmann et al., 1993, "Simulating the critical behavior of complex fluids", *Nature* 365: 330–332.

Skalicky et al., 1993, "Solution structure of the calcium channel antagonist ω–conotoxin GVIA", *Protein Science* 10: 1591–1603.

Slichter, 1989, *Principles of Magnetic Resonance* (Springer–Verlag, Berlin) Chapter 8; pp. 367–428.

Smit and Siepmann, 1994, "Computer Simulations of the Energetics and Siting of η–Alkanes in zeolites", *J. Phys. Chem.* 98: 8442–8452.

Sternberg and Hoess, 1995, "Display of peptides and proteins on the surface of bacteriophage λ," *Proc. Natl. Acad. Sci. USA* 92: 1609–1613.

Tidor et al., 1993, "The Contribution of Cross–Links to Protein Stability: A Normal Mode Analysis of the Configurational Entropy of the Native State", *Proteins: Structure, Function and Genetics* 15:71–79.

Vasavada et al., 1991, "A contingent replication assay for the detection of protein—protein interactions in animal cells", *Proc. Natl. Acad. Sci. USA* 88: 10686–10690.

Weiner et al., 1986, "An all atom force field for simulations of proteins and nucleic acids", *J. of Computational Chem.* 7: 230–252.

Weiner et al., 1984, "A New Force Field for Molecular Mechanical Simulation of Nucleic Acids and Proteins", *J. Amer. Chem. Soc.* 106: 765–784.

Wells, James A., 1994, Structural and functional baqsis for hormone binding and receptor oligomerizatio , *Curr. Op. Cell Bio.*, 6: 163–173.

Yu et al., 1994, "Structural Basis for the Binding of Proline–Rich Peptides of SH3 Domains", *Cell* 76: 933–945.

Zhang et al., 1993 "Normal and oncogenic p21$^{ras}$ proteins bind to the amino–terminal regulatory domain of c–Raf–1", *Nature* 364: 308–313.

Bianchi et al., 1995, "A conformationally homogeneous combinatorial peptide library", *J. Mol. Biol.* 247:154–160.

Fernandez et al., 1992, "Magnetic resonance of polypeptides adsorbed on silica and hydroxyapatite surfaces", *J. Am. Chem. Soc.* 114:9634–9642.

Hodgkin et al., 1993, "A Monte Carlo pharmacophore generation procedure: Application to the human PAF receptor", *J. Computer–Aided Molecular Design* 7:515–534.

Sepetov et al., 1995, "Library of libraries: Approach to synthetic combinatorial library design and screeening of 'pharmacophere' motifs", *Proc. Natl. Acad. Sci. USA* 92:5426–5430.

Wilson et al., 1993, "The calculation and synthesis of a template molecule", *Tetrahedron* 49:3655–3663.

Blum et al., 1988, Polymer Preprints, Am. Chem Society 29(1):54–55.

Sindorf, 1983, J. Am. Chem. Soc. 105: 1848–1851.

Faccini et al., 1984, Macromolecules 17:2405–2411.

Creuzet et al., 1991, Science 351:783–786.

METHOD OF USING SOLID STATE NMR TO MEASURE DISTANCES BETWEEN NUCLEI IN COMPOUNDS ATTACHED TO A SURFACE

This is a division, of application Ser. No. 08/418,992 filed Mar. 31, 1995, which is incorporated by reference herein in its entirety.

This invention was made with Government support under Grant number 1R43CA62752-01 awarded by the National Institutes of Health. The Government has certain rights in the invention.

This specification includes a microfiche appendix containing a listing of the computer programs of this invention, this appendix comprising 2 microfiche of 101 total frames.

TABLE OF CONTENTS

1. FIELD OF THE INVENTION
2. BACKGROUND
2.1. TARGET STRUCTURE-BASED APPROACHES TO DRUG DESIGN
2.2. DIVERSITY-BASED APPROACHES TO DRUG DESIGN
3. SUMMARY OF THE INVENTION
4. BRIEF DESCRIPTION OF THE DRAWINGS
5. DETAILED DESCRIPTION
5.1. SELECTION OF A TARGET MOLECULE
5.2. DIVERSITY LIBRARIES
5.3. SCREENING OF DIVERSITY LIBRARIES
5.4. DETERMINING THE SEQUENCE OR CHEMICAL FORMULA OF BINDERS
5.5. CANDIDATE PHARMACOPHORE SELECTION
5.6. INTRAMOLECULAR DISTANCE MEASUREMENTS
5.7. CONSENSUS, CONFIGURATIONAL BIAS MONTE CARLO
5.8. CONSENSUS STRUCTURE TEST
5.9. LEAD COMPOUND DETERMINATION
5.10. APPENDIX: CONCERTED ROTATION
6. EXAMPLES
6.1. RELATION BETWEEN EFFECTIVENESS OF POTENTIAL DRUG IDENTIFICATIONS AND PHARMACOPHORE GEOMETRIC TOLERANCE
6.2. EXPRESSION AND PURIFICATION OF TARGET PROTEINS
6.3. SYNTHESIS AND SCREENING OF POLYSOME-BASED LIBRARIES ENCODING RANDOM CONSTRAINED PEPTIDES OF VARIOUS LENGTHS
6.3.1. PREPARATION OF DNA TEMPLATES
6.3.2. IN VITRO SYNTHESIS AND ISOLATION OF POLYSOMES
6.3.3. AFFINITY SELECTION/SCREENING OF POLYSOMES
6.4. PHAGEMID SCREENING
6.4.1. PLATE PROTOCOL
6.4.2. BIOTIN-ANTIBIOTIN IgG BEAD PROTOCOL
6.4.3. BIOTIN-STREPTAVIDIN, MAGNETIC BEAD PROTOCOLS
6.5. AFFINITY MEASUREMENTS OF PEPTIDE-TARGET PROTEIN INTERACTIONS
6.6. REDOR MEASUREMENTS ON A $CX_6C$ PEPTIDE RESIN
7. SPECIFIC EMBODIMENTS, CITATION OF REFERENCES

A portion of the disclosure of this patent document contains material which is subject to copyright protection. The copyright owner has no objection to the facsimile reproduction by any one of the patent disclosure, as it appears in the Patent and Trademark Office patent files and records, but otherwise reserves all copyright rights whatsoever.

1. FIELD OF THE INVENTION

The field of this invention is computer assisted methods of drug design. More particularly the field of this invention is computer implemented smart Monte Carlo methods which utilize NMR and binders to a target of interest as inputs to determine highly accurate molecular structures that must be possessed by a drug in order to achieve an effect of interest. Illustrative U.S. Patents are U.S. Pat. No. 5,331,573 to Balaji et al., U.S. Pat. No. 5,307,287 to Cramer, III et al.; U.S. Pat. No. 5,241,470 to Lee at al., and U.S. Pat. No. 5,265,030 to Skolnick et al.

2. BACKGROUND

Protein interactions have recently emerged as a fundamental target for pharmacological intervention. For example, the top two major uncured diseases in the United States are atherosclerosis (the principal cause of heart attack and stroke) and cancer. These diseases are responsible for greater than 50% of all U.S. mortality and cost the U.S. economy over $200 billion per year. A consistent picture of these diseases, which has gradually emerged during the past ten years of molecular biological and medical research, views both as triggered by disordering of specific molecular recognition events that take place among sets of proteins present in both the normal and disease states.

Hierarchical, organized patterns of protein-protein interactions are often referred to as "pathways" or "cascades." At the molecular level, cancers have been determined to be the deregulation of pathways of interacting proteins responsible for guiding cellular growth and differentiation. During the past year, individual cellular events have been organized into nearly complete mechanistic explanations of how a cell's behavior is controlled by its environment and how communication pathway errors lead to uncontrolled proliferation and cancer. Disruption in similar pathways are responsible for the proliferation of blood vessel walls marking the atherosclerotic disease state (Cook et al., 1994, Nature 369:361–362; Hall, 1994, Science 264:1413–1414; Ross, 1993, Nature 362:801–809; Zhang et al., 1993, Nature 364:308–313).

Inhibition or stimulation of particular protein-substrate interactions have long been known drug targets. Many important anti-hypertensives, neurotransmitter analogues, antibiotics, and chemotherapeutic agents act in this fashion. Captopril, an antihypertensive drug, was designed based on its ability to antagonize a focal blood-pressure-regulating enzyme.

Proteins involved in biological processes, either as part of protein-protein pathways or as enzymes, are composed of domains (Campbell et al., 1994, Trend. BioTech. 12:168–172; Rothberg et al., 1992, J. Mol. Biol. 227:367–370). Domains, or regions of the protein of stable three dimensional (secondary and tertiary) structures, play several major roles, including providing on their surface small regions ("examples of targets"), where proteins and substrates are able to bind and interact, and functioning as structural units holding other domains together as part of a large protein (tertiary and quaternary structure). The interaction surface of a domain or target is fundamental to determining binding specificity. Targets are often small enough that the principal contribution to the binding energy is short range, highly localized to several amino acids (Wells, 1994, Curr. Op. Cell Biol. 6:163–174). The functional specificity of targets and domains, responsible for the incredible diversity of cellular function, ultimately rests with the arrangement of amino acid side chains forming their interaction surfaces, or targets (Marengere et al., 1994, Nature 369:502–505).

It can be appreciated, therefore, that pharmacological intervention affecting the specific protein-protein and protein-substrate recognition events occurring at protein targets is of fundamental importance, particularly for effective drug design.

However, achieving desired pharmacological interventions in a predictable manner remains as elusive as ever. Early approaches to drug design depended on the chance observation of biological effects of a known compound or the screening of large numbers of exotic compounds, usually derived from natural sources, for any biological effects. The nature of the actual protein target was usually unknown.

2.1. TARGET STRUCTURE-BASED APPROACHES TO DRUG DESIGN

Rational approaches to drug design have met with only limited success. Current rational approaches are based on first determining the entire structure of the proteins involved in particular interactions, examining this structure for the possible targets, and then predicting possible drug molecules likely to bind to the possible target. Thus the location of each of the thousands of atoms in a protein must be accurately determined before drug design can begin.

Direct experimental and indirect computational methods for protein structure determination are in current use. However, none of these methods appears to be sufficiently accurate for drug design purposes according to current rational approaches.

The primary direct experimental methods for determining the structure of proteins involved in particular interactions are X-ray crystallography, relying on the interaction of electron clouds with X-rays, and liquid nuclear magnetic resonance (NMR), relying on correlations between polarized nuclear spins interacting via indirect dipole-dipole interactions. X-ray methods provide information on the location of every heavy atom in a crystal of interest accurate to 0.5–2.0 Å (1 Å=$10^{-8}$ cm). Drawbacks of x-ray methods include difficulties in obtaining high-quality crystals, expense and time associated with the crystallization process, and difficulties in resolving whether or not the structure of the crystalline forms is representative of the in vivo conformation (Clore et al., 1991, J. Mol. Biol. 221:47; Shaanan et al., 1992, Science 227:961–964). High resolution, multidimensional, liquid phase NMR techniques represent an attractive alternative, to the extent that they can be applied in situ (i.e., in aqueous environment) to the study of small protein domains (Yu et al., 1994, Cell 76:933–945). However, the complexity of the analysis of the various mutual correlations is time consuming, and the correlations (primarily from the nuclear Overhausser effect) provide no better accuracy than X-ray methods. Isotopic enrichment of proteins with $^{13}C$ and $^{15}N$ reduces the time associated with analysis, but at a great expense (Anglister et al., 1993, Frontiers of NMR in Biology III LZ011).

Protein structures determined by any of these current methods do not predict success in subsequent drug design. Resolution obtainable either by measurement or computation, generally 0.5–2 Å, has often been found to be inadequate for effective direct drug design, or for selection of a lead compound from organic compound libraries. The resolution required to understand both drug affinity and drug specificity, although not precisely known, is probably measured in fractions of an Å, down to 0.1 Å (MacArthur et al., 1994, Trend. BioTech. 12:149–153). This accuracy appears to be beyond the capabilities of many current methodologies.

Prior research has identified tools which, although promising, cannot be used in a coordinated manner for drug design. One promising measurement approach with speed, simplicity, accuracy, and the ability to carefully control the measurement environment is rotational echo double resonance (REDOR) NMR, a type of solid state NMR (Guillion and Schaefer, 1989, J. Magnetic Resonance 81:196; Holl et al., 1990, J. Magnetic Resonance 81:620–626 and McWherter, 1993, J. Am. Chem. Soc. 115:238–244). REDOR accuracy can be below the 0.1 Å believed to be sufficient for direct drug design. However, since REDOR measures only a few selected distances, it is not usable in drug design methods which depend on the initial determination of the complete structure of the protein containing the target of interest.

Once a target's structure is determined by the above methods, most rational drug design paradigms call for the prediction of small drug structures that will bind (or dock) to the target. This prediction is generally done by computational methods, of which several are in current use. Most seek to predict the position of all the thousands of atoms in a drug structure. Purely ab initio computational approaches to high resolution structure analysis, such as quantum statistical mechanics and molecular dynamics, require prohibitive computing resources. To apply either approach, the potential energy, or Hamiltonian, of the entire system must be known. Statistical mechanics provides an expression for the probability of any given protein configuration as a ratio of partition functions. Proper quantum statistical mechanics required for an exact evaluation of full protein partition functions is not currently computationally feasible, as it would involve many thousands of atoms including the target, the protein, and the aqueous environment. The application of even simple, approximate quantum statistical mechanics to simple systems in aqueous environments is currently a non-trivial task (Chandler, 1991, in *Liquids, Freezing, and Glass Transitions,* Elsevier, N.Y., p. 195). Molecular dynamics computes the dynamics of a molecule's motion in time. Computing the atomic dynamics of all the perhaps thousands atoms of a protein is an extreme computational burden. Only picoseconds, or at most a few nanoseconds, of molecular time can be simulated, which is insufficient to determine a high resolution, equilibrium, structure (Smit et al., 1994, J. Phys. Chem. 98:8442–8452). In any case, most of the information determined is wasted, since only the structure of the protein binding target are of interest in drug design.

Further, current approximate computational techniques for protein structure determination are in need of greater accuracy or efficiency. The most common techniques depend on Molecular Dynamics or Monte Carlo methods (Nikiforovich, 1994, Int. J. Peptide Protein Res. 44:513–531; Brünger and Karplus, 1991, Acc. Chem. Res. 24:54–61). These methods randomly alter initial molecular structures by generating simulated thermal perturbations, and then average the ensemble of results to determine a final structure. The generated perturbation must preserve all structural constraints and be energetically favorable. If both conditions are not met, the perturbation will be discarded. Current Monte Carlo methods applied to constrained protein structure determinations productively use only approximately 1 out of $10^5$ perturbed structures generated (Siepmann et al., 1993, Nature 365:330–332). This extreme waste of computer resources results in time consuming, low resolution structure determinations.

To summarize, existing rational drug design methods based on identification of target structure fail to reliably yield drug molecules due to experimental structure determination difficulties and computational difficulties associated with predicting drug structures with ill-defined Hamiltonians.

2.2. DIVERSITY-BASED APPROACHES TO DRUG DESIGN

Another method for exploring protein target interactions utilizes "recognition systems" which comprise huge libraries of related molecules (Clarkson et al., 1994, Trend. BioTech. 12:173–184). From such a library only those members binding to the target of interest are selected. Such recognition systems must encompass the structural diversity of protein targets while being amenable to serve for the selection of lead compounds for drug design. Antibodies are one classic example of such a system that certainly meets the recognition requirement. Unfortunately, there is a need to determine the antibody structures needed for lead compound selection more rapidly and accurately. While about 2000 recognition regions have been sequenced, only about 23 in the Brookhaven Protein Structural Database have structures determined to even within 2 Å (Rees et al., 1994, Trends in Biotech. 12:199–206).

Promising recognition systems at the opposite extreme comprise huge libraries of small peptides. The small peptides must be sufficiently diverse so that they attain a level of affinity and specificity similar to that obtained by protein domains. Given the role peptides play in nature, this condition can be met by surprisingly small structures, with 6 to 12 amino acids. However, linear peptides are either unstructured or weakly structured at room temperature in aqueous solutions (Alberg et al., 1993, Science 262:248; Skalicky et al., 1993, Protein Science 10:1591–1603). From a practical viewpoint, linear peptides must be constrained to reduce their degrees of freedom (reduced conformational entropy) and to increase their chances for strongly binding. These constraints, or scaffolds, limit the range of stable conformations and make more straightforward determining bound structure (Olivera et al., 1990, Science 249:259; Tidor et al., 1993, Proteins: Structure Function and Genetics 15:71).

Methods are now available to create such libraries and to select library members that recognize a specific protein target. The production of constrained peptide diversity libraries requires synthesizing oligonucleotides with the desired degeneracy to code for the peptides and ligating them into selection vectors (Goldman et al., 1994, Bio/Tech. 10:1557–1561). Once a constrained structured diversity library is created, it is a source from which to select specific members that bind to a target of interest. Beginning with a known pathway involving specific domain-domain or protein-substrate interactions at a target, molecular biological methods can be used to identify in a matter of days small ensembles of highly constrained peptides from these huge libraries that bind to these domains with high affinity and specificity.

While this field has been exploding in the last few years and showing great potential, it is severely limited by its use in isolation without the benefit of integrated structural analysis needed both to derive the high resolution structures of binding peptides and also to direct the construction of additional structured libraries. Drug design is not aided by having library members recognizing the protein target of interest but without any understanding of why the recognition occurs. This is entirely similar to the random screening methods of early fortuitous drug design efforts.

Unfortunately, rational drug design according to current approaches (target structure-based) remains an inefficient, laborious process with a disproportionately high lead-compound failure rate. Presently, about 90% of lead compounds fail to emerge successfully from clinical trials (Trends in U.S. Pharmaceutical Sales and Research and Development, Pharmaceutical Manufacturing Association, Washington, D.C., 1993).

It is becoming clear that low-resolution structures of an entire protein or target (at 0.5–2 Å), or an uncharacterized lead, such as produced by chemical diversity methods, leave much to be desired for use in drug design.

If the limitations of prior art methods were overcome and a sufficiently accurate structure needed by a molecule to bind to a target of interest could be determined, existing chemical libraries could be searched for highly targeted lead compounds with similar structure (Martin, 1992, J. Medicinal Chem. 35:2145–2154). This database search can be based not only on chemical and electronic properties, but also on geometric information. Such searches that have high resolution (better than 0.25 Å), would provide a vast improvement over the prior art, as lower resolutions lead to an exponentially increasing number of potential leads.

Computational methods to determine high resolution drug structures from recognition system binding information or NMR partial distance measurements are not currently available. No current structure determination methods uses such additional information to make more efficient or more accurate determination of high resolution structures (Holzman, 1994, Amer. Sci. 872:267).

Citation of a reference or discussion hereinabove shall not be construed as an admission that such is prior art to the present invention.

3. SUMMARY OF THE INVENTION

It is a broad object of this invention to address the prior art problems of drug design by providing a method of rational design of drugs that achieve their effect by binding to a target molecule or molecular complex of interest. Importantly, this object is achieved without requiring determination of the structure of the molecule or molecular complex ("target molecule") bearing the target or even of the target itself. The method is target structure independent. The method of the invention uses an interdisciplinary combination of computational modeling and simulation, experimental distance constraints, and molecular biology.

In an important aspect, the invention provides a computer implemented modeling and simulation method to determine a highly accurate consensus structure for the pharmacophore and a structure for the remainder of the molecule from diversity library members that bind to the protein target of interest. Where prior structure determination methods focused on the structure of the target molecule or of the target, the method of this invention is uniquely adapted to focus instead on the structures of molecules that bind to the target. Such structural information is directly applicable to drug design since it defines the structure a drug must possess to bind to the target of interest. Also, this structural information is much easier to determine by use of the present invention, since it concerns molecules with many fewer atoms than the target molecule. The method of the invention achieves accuracy by improving upon the accuracy and utility of the input structural information. In a further embodiment of the invention, the method employed for structural determination is a smart Monte Carlo technique adapted to small constrained molecules.

The structure determination method of the invention allows one to take maximum advantage of the information obtained from the molecular biological selection of the diversity library members that tightly and specifically bind to the target molecule of interest. The selected library members must share some common structure to bind to the same target molecule. The smart Monte Carlo computer method of this invention specifically seeks and provides this common structure.

The invention also provides a method of performing REDOR NMR measurements of molecules on a solid phase substrate. In a preferred embodiment, the substrate is a solid phase on which the molecule (e.g., peptide) has been synthesized, with a high degree of purity. In another preferred embodiment, performing REDOR measurements of such a molecule on a substrate can be done in a dry nitrogen atmosphere, under hydrated conditions, and when the molecule is either free or bound to a target. In a specific embodiment, the REDOR measurements are accurate to better than 0.05 Å from 0 to 4 Å, and to better than 0.1 Å from 4 to 8 Å. In an advantageous aspect of the invention, the structure determination method makes maximum use of these highly accurate internuclear distance measurements to constrain the determined common structure for the binding library members.

The invention also provides methods of identifying a compound that specifically binds to a target molecule, by first screening a diversity library, and then using a genetic selection method for screening the compounds identified from the diversity library.

In broad aspects, the invention provides a method and apparatus for rational and predictable design of new and/or improved drugs that achieve their effect by binding to a specified target molecule. More particularly, the invention is directed to a method for the rational selection of highly specific lead compounds for such drug design, including the computer implemented step of highly accurate determination of the structure responsible for this target binding by the highly accurate, consensus, configurational bias Monte Carlo method.

A lead compound serves as a starting point for drug development both because it specifically binds to the protein target of interest, achieving the biological effect of interest, and because it has or can be modified to have good pharmacokinetics and medicinal applicability. A final drug may be the lead compound or may be derived therefrom by modifying the lead to maximize beneficial effects and minimize harmful side-effects. Although any lead compound is useful, a lead that tightly and specifically binds to the target molecule of interest in a known manner, such as can be provided by the invention, is of great use. Knowledge of the high resolution structures' in a lead compound responsible for its binding and activity provides a more focused and efficient drug development process.

The methods of the invention improve lead compound determination, by determining the "pharmacophore", the precise structural characteristics needed for a lead compound to specifically bind to a target of interest. The most fundamental specification of a pharmacophore is in terms of the electronic properties necessary for a molecule to specifically bind to the surface of a target molecule. These properties may be fundamentally represented by requirements on the ground and low lying excited state wave functions of a pharmacophore, such as, for example, by specifying requirements on the well known multiple expansion of these wave functions.

The preferred pharmacophore specification according to the invention is in terms of both the chemical groups making up the pharmacophore and determining its electronic properties and also the geometric relationships of these groups. This chemical representation is not the only possible representation of the pharmacophore. Several chemical arrangements may have similar electronic properties. For example, if a pharmacophore specification included an —OH group at a particular position, a substantially equivalent specification might include an —SH group at the same position. Equivalent chemical groups that may be substituted in a pharmacophore specification without substantially changing its nature are called "homologous".

In particular embodiments, therefore, this invention provides a method and apparatus for the highly accurate determination of the pharmacophore needed to specifically bind to the target molecule of interest, by a specification of the geometric relationships of the important chemical groups. The pharmacophore is preferably determined by a smart Monte Carlo method from molecular biological input specifying molecules (preferably selected from among diversity libraries) that specifically bind to the target molecule and also preferably from REDOR NMR data specifying a few highly accurate distances in these selected molecules.

An important advantage provided by the invention is the ability to make a pharmacophore structure determination without relying on any knowledge of the structure of the target molecule or target. Where the target molecule is a protein, conventional prior art methods have sought to sequence and determine the structure of the protein containing the target, hoping thereby to determine active sites by examination of the structure. A further important advantage of the invention is that this structure determination can be made by use of a relatively small number of actual physical position measurements. In contrast, conventional methods using X-ray crystallography and liquid NMR require determination of positions of all atoms in the molecule ("binder") that specifically binds to the target, and the target. An additional advantage provided by the invention is that, in a preferred embodiment wherein REDOR structural measurements provide input information, the accuracy of the pharmacophore structure determination can be at least approximately 0.25–0.50 Å or better. This accuracy is provided by the combination of an efficient, Monte Carlo technique for structure determination with a few highly accurate distance determinations.

4. BRIEF DESCRIPTION OF THE DRAWINGS

These and other features, aspects, and advantages of the present invention will become better understood by reference to the accompanying drawings, following description, and appended claims, where:

5. DETAILED DESCRIPTION

Figure 1:
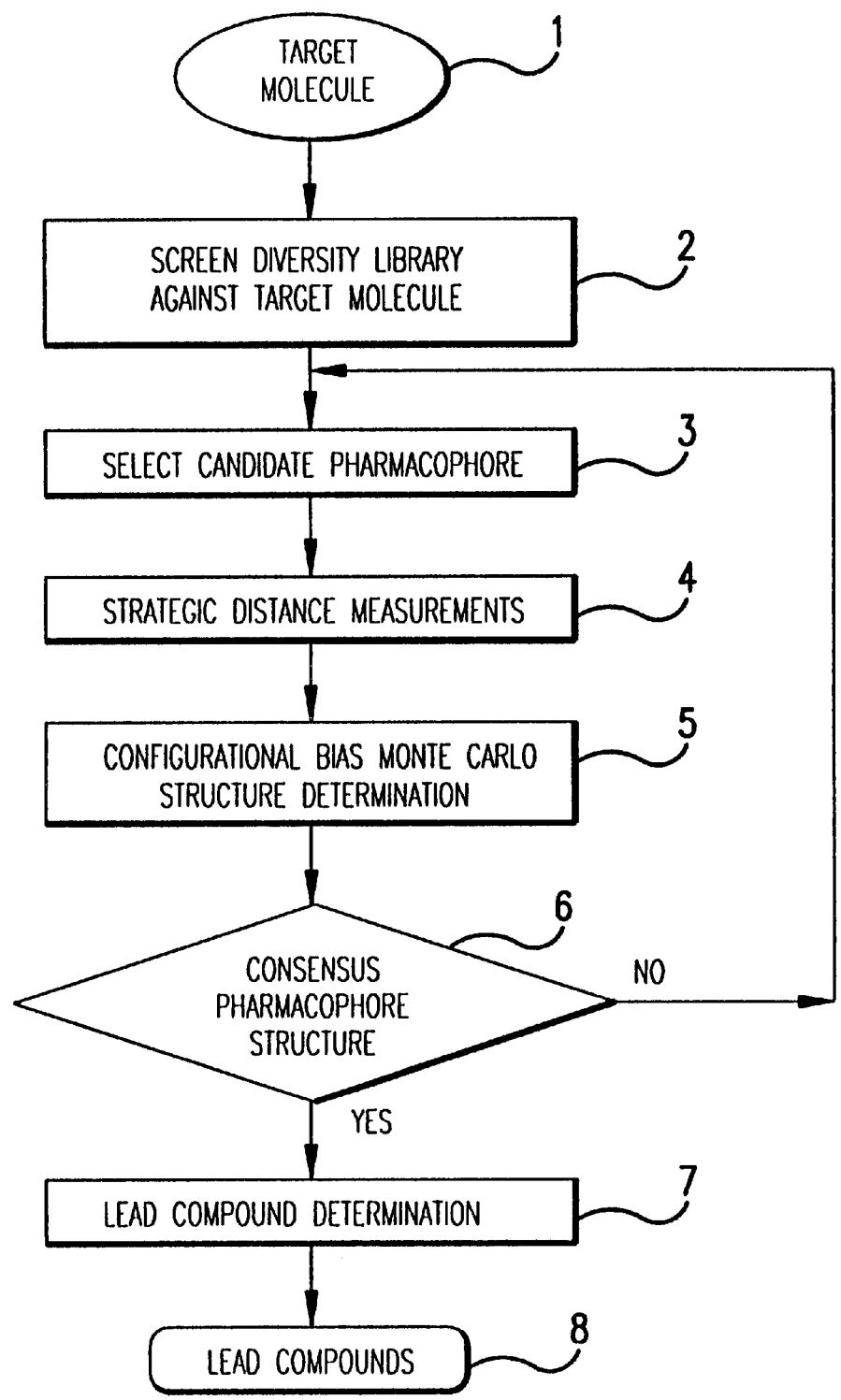
FIG. 1 is the overall method of this invention in its broadest aspect.

For clarity of disclosure, and not by way of limitation, the detailed description of the invention is described as a series of steps. A broad view of the exemplary steps of which the invention is comprised is presented in FIG. 1, a brief overview of which is presented in the text that follows.

The invention method preferably begins with a target molecule (or molecular complex) 1 having a binding target of biological or pharmacological interest. Specific binding of a molecule to the target is predicted to affect its biological activity and may provide biological effects of interest. For example, these effects might include amelioration of a disease process or alteration of a physiological response. Lead compounds 8 output from the invention are able to specifically bind to target molecule 1 and can serve as starting points for the design of a drug able to specifically bind to the target.

Diversity library screening, step 2, allows the selection from among library members of a plurality of molecules [hereinafter called "binders"] that specifically bind to target molecule (or molecular complex) 1; the chemical building block structure (e.g., sequence, structural formula) is then determined. If predetermined binders and their structure are already available, the invention can use this information directly without the need for library screening. If library screening is done, one or more libraries may be screened. The selected binders all share a common pharmacophore structure, allowing their specific binding to the target in a chemically and physically similar manner. This common structure is preferably iteratively determined by a select and test method. Candidate pharmacophore selection, step 3, is based upon chemical structure homologies. Geometric and conformational information is not needed to be used at this step and is preferably not considered. A candidate pharmacophore shared by all the N binders is selected, step 3, for structure determination by subsequent steps. The binders will typically present several candidate chemical pharmacophores, ignoring conformation considerations. These candidates are small groups of library building blocks, often contiguous, each candidate group in one binder being homologous to the candidate groups in all the other binders. Building block homologies are determined by applying rules appropriate to the diversity library. In the preferred embodiment, homologous building blocks have similar surface chemical groups, since pharmacophores are defined by a similar geometric arrangement of chemical structures. In the case of the preferred library, $CX_6C$, candidate pharmacophores are amino acid sequences whose side chain surface groups have similar chemical properties. Amino acid homologies are determined by mechanical rules described below. These candidate sequences are typically 3 amino acids long, but may range from 2 all the way to 6. Where pharmacophores are defined by their charge distributions, homologous library building blocks must have similar charge distributions.

Having selected N binders by screening one or more libraries and determined a candidate pharmacophore in each binder, the subsequent steps of distance measurement, step 4, and Monte Carlo structure determination, step 5, determine a highly accurate structure for the candidate pharmacophore, if possible. This determination will be possible if the candidate is the actual pharmacophore. A subsequent test, step 6, checks for success of this structure determination. In particular cases, distance measurements may not be necessary in order to determine an adequately precise pharmacophore structure.

Measurements are made, step 4, of a few strategic distances in the binders, that will be most useful for the subsequent structure determination step. A minimum number of strategic interatomic distances in the binders are measured in step 4. These few distances constrain possible binder structures and make the subsequent complete structure determination more efficient and more accurate. In preferred but not limiting embodiments, measurement methods yielding distances accurate to at least approximately 0.25 Å or less are used. The preferred methods use nuclear magnetic resonance ["NMR"] techniques. Particularly preferred is the rotational-echo double resonance ["REDOR"] NMR method for directly measuring $^{13}C-^{15}N$ internuclear distances in peptides, the most accurate current method for simply and inexpensively obtaining such distances. It is generally capable of accuracy to 0.1 Å and a span of 8 Å. In a specific embodiment, peptide binders are synthesized from amino acids labeled with $^{13}C$ and $^{15}N$. Labeling is chosen to obtain the most useful distance data about the selected candidate pharmacophore structures. Either backbone nuclei, side chain nuclei, or both can be labeled. The step is detailed below. Liquid NMR techniques can also be used to indirectly determine internuclear distances in peptides, but are less preferred since they require considerable data interpretation to obtain distances of less accuracy than those obtained by use of REDOR.

Structure determination, step 5, determines a precise geometric conformation for both the candidate shared chemical structures, if possible, and the remainder of the binders. The preferred but not limiting method, consensus, configurational bias, Monte Carlo ["CCBMC"] determination, step 5, is an efficient smart Monte Carlo method uniquely able to incorporate knowledge from prior steps to obtain highly accurate physical binder structures. From library screening, step 2, it is deduced that the binders have a shared, actual pharmacophore, structure because they all bind specifically to the same target molecule (hence, a "consensus" method). It is not significant to the method if the binders come from more than one library as long as they all have a structure adaptable to representation in the consensus structure determination step (see infra). From distance measurements, step 4, a few strategically chosen distances are accurately known. This information is heuristically utilized along with an accurate model of the physical atomic interactions and the allowed molecular conformations.

Further, these means are particularly adapted for determining structures of molecules having limited conformational degrees of freedom at the temperature of interest and conformationally constrained by, e.g., internal bonds. Potential conformations are generated and selected by smart configuration bias techniques which avoid generation of unnecessarily improbable new conformations. (Hence, a "configuration bias" method.) The technique is preferably applied herein to conformationally constrained peptides. A concerted rotation technique is combined with configurational bias conformation generation so that new conformations automatically preserve the internally linked backbone structure constraints. This technique is preferably applied to the preferred constrained peptide library, of a sequence comprising $CX_6C$ (wherein X is any amino acid). The technique is also applicable to other constrained peptide libraries, to peptoid libraries, and to any more general organic diversity libraries that meet certain geometric limitations. (i.e., that have structures adaptable to representation in the consensus structure determination step (see infra)).

The methods of the invention are not limited to the use of CCBMC for determining a consensus pharmacophore structure. Alternative embodiments of this invention may use alternative structure determination methods to determine a consensus pharmacophore structure. For example, a simple yet expensive method is to make exhaustive REDOR NMR measurements characterizing the candidate pharmacophore in each binder and then average these measurements. A somewhat less expensive method is to use a conventional Monte Carlo molecular structure determination method to limit somewhat the number of REDOR NMR measurements required to characterize the candidate pharmacophore. Conventional Monte Carlo methods, being unable to directly make use of partial distance measurements or consensus binding information, are less efficient than the CCBMC method and require more distance measurements. Further, other known techniques of molecular structure determination, for example folding rules or molecular dynamics, can be used in place of conventional Monte Carlo.

The success of the structure determination is tested, step 6, against various convergence and success criteria. Consistency tests, step 6, are applied to the resulting structure to determine whether the candidate pharmacophore previously selected is the actual pharmacophore. One set of tests checks predicted distances against new distance measurements or against previous measurements temporarily not used as structure constraints. A second set of tests checks heuristically whether the candidate pharmacophore exhibits the expected low energy consensus structure. The test are described further below. If a shared structure is found, the candidate pharmacophore must be the actual pharmacophore. If not, another candidate pharmacophore and another shared structure is determined, if possible. An actual pharmacophore exists and will eventually be found and accurately structured.

Upon passing these tests, the methods of the invention have provided a consensus structure for the selected candidate pharmacophore, preferably accurate to at least approximately 0.25–0.50 Å, as well as structures for the remainder of the binder molecules. Lead compound selection, step 7, uses these structures to determine or select highly targeted lead compounds 8. One method of lead selection is to design new organic molecules of pharmacologic utility with the determined pharmacophore structure. Another method selects leads from databases of molecular descriptions. Conventionally known to medicinal chemists are databases of potential drug compounds indexed by their significant chemical and geometric structure (e.g., the Standard Drugs File (Derwent Publications Ltd., London, England), the Bielstein database (Bielstein Information, Frankfurt, Germany or Chicago), and the Chemical Registry database (CAS, Columbus, Ohio)). The determined pharmacophore, being a chemical and geometric structure in the preferred embodiment, is used to query such a database. Search results will be those compounds with homologous chemical groups arrayed in a very closely similar geometric arrangement. These are lead compounds 8 output from this invention and input to the process of drug testing and development.

Although the preferred identity and ordering of the method steps is presented in FIG. 1, the invention is not limited to this identity and ordering. Other orderings, especially of steps 3, 4, and 5, are possible to achieve certain efficiencies. Steps can be inserted and deleted, for optimal effect. For example, an additional partial structure determination step can be inserted between existing steps 3 and 4 to provide information on how best to make the step 4 strategic measurements. As another example, in an alternative aspect, in lieu of screening one or more libraries to select binders, predetermined binders can be obtained and used (e.g., binders determined by any means to be specific to the same target molecule); thus, step 2 can be omitted. In another embodiment, step 4, the measurement step, can be omitted. While all method steps in the preferred embodiment assume an aqueous environment at body temperature (37° C.), to the extent these parameters are relevant to the particular step, the invention is not limited to human environmental parameters.

Screening against a diversity library consists of selecting by assay those library members which bind specifically to the target molecule of interest. Binding specificity is preferably a binding constant of less than 1 μm (micromolar), and more preferably less than 100 nm (nanomolar). Preferably, an assay is done that detects an effect of binding of the binder to the target molecule on the target molecule's biological activity, to ensure that the binding is actually to the biological target of interest. Also, preferably, the selected binders are tested to further select those binders that bind to the target molecule competitively, to ensure that each binds to the same target in the target molecule.

The output of the screening step is a number, N, of binders selected from one or more libraries for use by the subsequent steps of the method. The binders with highest affinity are preferably selected for use by the subsequent steps. The chemical structure of each of the N binders selected for use is determined as part of the member synthesis and library screening. The primary chemical structure of the preferred constrained peptide library is specified by the amino acid sequence of the —$X_6$— portion of the $CX_6C$ molecule. For more general organic diversity libraries, the selection and arrangement of library building blocks in the binders must be determined.

It is a preferred aspect of this invention that the set of determined lead compounds is selective and small. Example 1 illustrates that as pharmacophore distance tolerances are relaxed, the number of compounds retrieved by drug database searches increases geometrically. As this invention determines high resolution pharmacophore geometries, it can be expected that database searches, or other methods of determining leads from pharmacophore structure, will return only a few, selective, targeted leads. Methods limiting the number of leads decrease the cost of drug development and are consequently of considerable utility to the pharmaceutical industry and medical community. The expense of developing and evaluating lead compounds for biological effect and medicinal usefulness is well known. Each lead compound must be screened for pharmacological usefulness, efficacy, and safety. Often chemical modifications are required and the process must be repeated. Finally, the required in vivo pharmacologic toxicity and clinical trials alone can consume years of time and millions of dollars.

Therefore, starting with a target molecule 1 having a biologically or pharmacologically interesting target, the method and apparatus of this invention determines a consensus pharmacophore structure. This consensus pharmacophore structure can then be used to determine a selective set of highly specific lead compounds 8 (FIG. 1) for rational design of drugs, e.g., capable of acting as ligand-mimics (agonists or antagonists) for the particular target molecule.

In the following discussion and examples, each of these steps will be more fully described.

5.1. SELECTION OF A TARGET MOLECULE

The target molecule is any one or more molecules containing a target or putative target of interest. The target is a binding interaction region. The target can be in a single molecule or can be a product of a molecular complex. The target can be a continuous or discontinuous binding region. The target molecule selected for use (FIG. 1, step 1) is preferably any molecule that is found in vivo (preferably in mammals, most preferably in humans) and that has biological activity, preferably involved or putatively involved in the onset, progression, or manifestation of a disease or disorder. The target molecule can also be a fragment or derivative of such an in vivo molecule, or a chemical entity that contains the same target as the in vivo molecule. Examples of such molecules are well known in the art. Such molecules can be of mammalian, human, viral, bacterial, or fungal origin, or from a pathogen, to give just some examples. The target molecule is preferably a protein or protein complex. The target molecules that can be used include but are not limited to receptors, ligands for receptors, antibodies or portions thereof (e.g., Fab, Fab', F(ab')$_2$, constant region), proteins or fragments thereof, nucleic acids, glycoproteins, polysaccharides, antigens, epitopes, cells and cellular components, subcellular particles, carbohydrates, enzymes, enzyme substrates, oncogenes (e.g., cellular, viral; oncogenes such as ras, raf, etc.), growth factors (e.g., epidermal growth factor, platelet-derived growth factor, fibroblast growth factor), lectins, protein A, protein G, organic compounds, organometallic compounds, viruses, prions, viroids, lipids, fatty acids, lipopolysaccharides, peptides, cellular metabolites, steroids, vitamins, amino acids, sugars, lipoproteins, cytokines, lymphokines, hormones, T cell surface antigens (e.g., CD4, CD8, T cell antigen receptor), ions, organic chemical groups, viral antigens (hepatitis B virus surface or core antigens, HIV antigens (e.g., gp120, gp46)), hepatitis C virus antigens, toxins (e.g., bacterial toxins), cell wall components, platelet antigens (e.g., gpiibiiia), cell surface proteins, cell adhesion molecules, neurotrophic factors, and neurotrophic factor receptors.

In specific embodiments, vEGF (vascular endothelial growth factor) or KDR (the receptor for vEGF) (Terman et al., 1992, Biochem. Biophys. Res. Comm. 187:1579–1586) is the target molecule. vEGF and its receptor are the major regulators of vasculogenesis and angiogenesis (Millauer et al., 1993, Cell 72:835). Inhibition of the vEGF and the concomitant inhibition of its mitogenic activity and angiogenic capacity has been shown to suppress tumor growth in vivo (Kendall et al., 1993, Proc. Natl. Acad. Sci. USA 90:10705–10709; Kim et al., 1993, Nature 362:841–844).

Use of vEGF or KDR or portions thereof, as a target molecule is a preferred embodiment for use of the present invention to develop lead molecules as drugs in the area of cardiovascular disease or cancer.

The proteins ras and raf, or portions thereof (e.g., modules—functional portions), are also preferred target molecules, particularly in an embodiment wherein the methods of the present invention are employed to develop lead molecules for drugs that are cancer therapeutics. ras is a member of an intracellular signaling cascade that controls cell growth and differentiation (Cook and McCormick, 1994, Nature 369:361–362). ras functions in signal transduction by specifically recognizing the protein raf and bringing it to the cell membrane (Hall, 1994, Science 264:1413–1414; Vojtek et al., 1993, Cell 74:205–214). The recognition modules in both ras and raf have been determined (Zhang et al., 1993, Nature 364:308–313; Warne et al., 1993, Nature 364:352–355; and Vojtek et al., 1993, Cell 74:205–214); in a specific embodiment, such a recognition module is used as a target molecule according to the invention.

In another specific embodiment, an integrin is used as a target molecule. Such molecules are known to function in clot formation, and can be used according to the present invention to develop lead molecules for drugs in the area of cardiovascular disorders.

Target molecules for use can be obtained commercially (where the target is commercially available), or can be synthesized or purified from natural or recombinant sources. In a specific embodiment, a target molecule is prepared that has been modified to incorporate an "affinity tag," i.e., a structure that specifically binds to a known binding partner, to facilitate recovery/isolation/immobilization of the target molecule. In a preferred aspect, recombinant expression methods well known in the art can be used to produce a protein target molecule as a fusion protein, incorporating a peptide affinity tag. Such affinity tags include but are not limited to epitopes of known antibodies.(e.g., c-myc epitope (Evan et al., 1985, Mol. Cell. Biol. 5:3610–3616)), a series (e.g., 5–7) of his residues (which bind to zinc), maltose binding sequences such as pmal, etc. Tags are incorporated into protein targets at either the amino or carboxy-terminus. In another embodiment, the target is chemically attached to a tag (e.g, biotin (which binds to avidin, streptavidin), streptavidin), e.g., by biotinylation.

The target molecule is purified by standard methods. For example, a protein target can be purified by standard methods including chromatography (e.g., ion exchange, affinity, and sizing column chromatography), centrifugation, differential solubility, or by any other standard technique for the purification of proteins; in a preferred embodiment, reverse phase HPLC (high performance liquid chromatography) is employed.

Once the target molecule has been purified, it is preferably tested to ensure that it retains its biological activity (and thus retains its native conformation). Any suitable in vitro or in vivo assay can be used. In instances where the desired target molecule is a fragment or derivative of a molecule found in vivo, or is a chemical entity putatively containing the same target as a molecule found in vivo, it is highly preferred that testing be done of such desired target molecules prior to their use, so that among such desired target molecules, only those that have the same biological activity as the in vivo molecule or compete with a known ligand to the in vivo molecule, are selected for actual use as target molecules according to the invention. In the event that biological activity has been reduced or lost in a recombinant protein relative to the native form of the protein, the protein can be recombinantly expressed in a different host (e.g., yeast, mammalian, or insect) and/or with a variety of tags and location of tags (on either the amino- or carboxy-terminal side), in order to attempt to achieve, or to optimize, recovery of biological activity.

5.2. DIVERSITY LIBRARIES

According to a preferred embodiment of the invention, diversity libraries are screened to select binders, which specifically bind to the target molecule. Diversity libraries are those containing a plurality of different members. Generally, the greater the number of library members and the greater the probability that all possible members are represented, the more preferred the library. In preferred embodiments, the diversity libraries have at least $10^4$ members, and more preferably at least $10^6$, $10^8$, $10^{10}$, or $10^{14}$, members.

Many libraries suitable for use are known in the art and can be used. Alternatively, libraries can be constructed using standard methods. Chemical (synthetic) libraries, recombinant expression libraries, or polysome-based libraries are exemplary types of libraries that can be used.

In a preferred embodiment, the library screened is a constrained, or semirigid library (having some degree of structural rigidity). Examples of constrained libraries are described below. A linear, or nonconstrained library, is less preferred although it may be used. Additionally, one or more different libraries can be screened to select binders.

In a preferred embodiment, the library contains peptide or peptide analogs having a length in the range of 5–18 amino acids or analogs thereof in each library member.

In specific embodiments, binders are identified from a random peptide expression library or a chemically synthesized random peptide library. The term "random" peptide libraries is meant to include within its scope libraries of both partially and totally random (variant) peptides.

In one embodiment, the peptide libraries used in the present invention may be libraries that are chemically synthesized in vitro. Examples of such libraries are given in Fodor et al., 1991, Science 251:767–773, which describes the synthesis of a known array of short peptides on an individual microscopic slide; Houghten et al., 1991, Nature 354:84–86, which describes mixtures of free hexapeptides in which the first and second residues in each peptide were individually and specifically defined; Lam et al., 1991, Nature 354:82–84, which describes a "one bead, one peptide" approach in which a solid phase split synthesis scheme produced a library of peptides in which each bead in the collection had immobilized thereon a single, random sequence of amino acid residues; Medynski, 1994, Bio/Technology 12:709–710, which describes split synthesis and T-bag synthesis methods; and Gallop et al., 1994, J. Medicinal Chemistry 37(9):1233–1251. Simply by way of other examples, a combinatorial library may be prepared for use, according to the methods of Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; or Salmon et al., 1993, Proc. Natl. Acad. Sci. USA 90:11708–11712. PCT Publication No. WO 93/20242 and Brenner and Lerner, 1992, Proc. Natl. Acad. Sci. USA 89:5381–5383 describe "encoded combinatorial chemical libraries," that contain oligonucleotide identifiers for each chemical polymer library member.

In another embodiment, biological random peptide libraries are used to identify a binder which binds to a target molecule of choice. Many suitable biological random peptide libraries are known in the art and can be used or can be constructed and used to screen for a binder that binds to a target molecule, according to standard methods commonly known in the art.

According to this approach, involving recombinant DNA techniques, peptides are expressed in biological systems as either soluble fusion proteins or viral capsid fusion proteins.

In a specific embodiment, a phage display library, in which the protein of interest is expressed as a fusion protein on the surface of a bacteriophage, is used (see, e.g., Smith, 1985, Science 228:1315–1317). A number of peptide libraries according to this approach have used the M13 phage. Although the N-terminus of the viral capsid protein, protein III (PIII), has been shown to be necessary for viral infection, the extreme N-terminus of the mature protein does tolerate alterations such as insertions. The protein PVIII is a major M13 viral capsid protein, which can also serve as a site for expressing peptides on the surface of M13 viral particles, in the construction of phage display libraries. Other phage such as lambda have been shown also to be able to display peptides or proteins on their surface and allow selection; these vectors may also be suitable for use in production of libraries (Sternberg and Hoess, 1995, Proc. Natl. Acad. Sci. USA 92:1609–1613).

Various random peptide libraries, in which the diverse peptides are expressed as phage fusion proteins, are known in the art and can be used. Examples of such libraries are described below.

Scott and Smith, 1990, Science 249:386–390 describe construction and expression of a library of hexapeptides on the surface of M13. The library was made by inserting a 33 base pair Bgl I digested oligonucleotide sequence into an Sfi I digested phage fd-tet, i.e., fUSE5 RF. The 33 base pair fragment contains a random or "degenerate" coding sequence $(NNK)_6$ where N represents G, A, T or C and K represents G or T. Cwirla et al., 1990, Proc. Natl. Acad. Sci. USA 87: 6378–6382 also described a library of hexapeptides expressed as pIII gene fusions of M13 fd phage. PCT publication WO 91/19818 dated Dec. 26, 1991 by Dower and Cwirla describes a library of pentameric to octameric random amino acid sequences.

Devlin et al., 1990, Science, 249:404–406, describes a peptide library of about 15 residues generated using an (NNS) coding scheme for oligonucleotide synthesis in which S is G or C.

Christian and colleagues have described a phage display library, expressing decapeptides (Christian, R. B., et al., 1992, J. Mol. Biol. 227:711–718). The DNA of the library was constructed by use of an oligonucleotide comprising the degenerate codons $[NN(G/T)]_{10}$ (SEQ ID NO:8) with a self-complementary 3' terminus. This sequence forms a hairpin which creates a self-priming replication site that was used by T4 DNA polymerase to generate the complementary strand. The double-stranded DNA was cleaved at the SfiI sites at the 5' terminus and hairpin for cloning into the fUSE5 vector described by Scott and Smith, supra.

Lenstra, 1992, J. Immunol. Meth. 152:149–157 describes a library that was constructed by annealing oligonucleotides of about 17 or 23 degenerate bases with an 8 nucleotide long palindromic sequence at their 3' ends. This resulted in the expression of random hexa- or octa-peptides as fusion proteins with the β-galactosidase protein in a bacterial expression vector. The DNA was then converted into a double-stranded form with Klenow DNA polymerase, blunt-end ligated into a vector, and then released as Hind III fragments. These fragments were then cloned into an expression vector at the sequence encoding the C-terminus of a truncated β-galactosidase to generate $10^7$ recombinants.

Kay et al., 1993, Gene 128:59–65 describes a random 38 amino acid peptide phage display library.

PCT Publication No. WO 94/18318 dated Aug. 18, 1994 describes random peptide phage display "TSAR libraries" that can be used.

Other biological peptide libraries which can be used include those described in U.S. Pat. No. 5,270,170 dated Dec. 14, 1993 and PCT Publication No. WO 91/19818 dated Dec. 26, 1991.

In a specific embodiment, a "peptide-on-plasmid" library, containing random peptides fused to a DNA binding protein that links the peptides to the plasmids encoding them, can be used (Cull et al., 1992, Proc. Natl. Acad. Sci. USA 89:1865–1869).

Another alternative to phage display or chemically synthesized libraries is a polysome-based library, which is based on the direct in vitro expression of the peptides of interest by an in vitro translation system (in some instances, coupled to an in vitro transcription system). These methods rely on polysomes to translate the genomic information (in this case encoded by an mRNA molecule, in some instances made in vitro by transcription from synthetic DNA) (see, e.g., Korman et al., 1982, Proc. Natl. Acad. Sci. USA 79:1844–1848). Such in vitro translation-based libraries include but are not limited to those described in PCT Publication No. WO 91/05058 dated Apr. 18, 1991; and Mattheakis et al., 1994, Proc. Natl. Acad. Sci. USA 91:9022–9026.

Diversity library screening, step 2 of FIG. 1, determines a few, N, members (compounds) from one or more libraries and their primary sequences all of which specifically bind to target molecule 1 in a similar manner. A structured organic diversity library is a prescription for the creation of a huge number of related molecules all built from combinations of a small number of chemical building blocks. Preferred diversity libraries for use according to the invention have members whose binding to a target molecule is characterized by configurational entropy change that are relatively small to the binding energy. This means that library members have definite structures in the bound and, especially, the unbound states. A preferred example of a chemical diversity library for use in the invention contains short peptides with a constrained conformation. Short peptides without constrained conformations are often freely flexible in an aqueous environment and adopt no fixed unbound structure. The binding of such library members is complicated by significant configurational entropy changes. To eliminate this complication, it is preferred that all library members have a constrained structure and bind to the target molecule in a specific and identifiable manner. One method of achieving constrained conformation is to require internal linking, such as by disulfide bonds.

Figure 10:
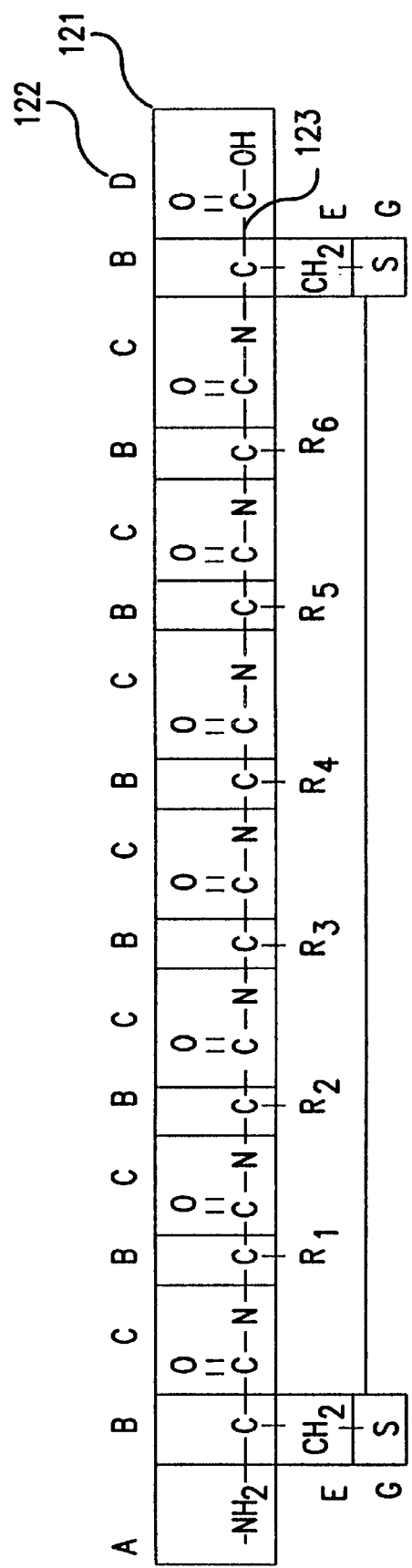
FIG. 10 is further detail of peptide memory representation used in the method of FIG. 8.

In one embodiment, disulfide bond formation is achieved by use of libraries that contain peptides having a pair of invariant cysteine residues, preferably positioned in the range of 2–16 residues apart, most preferably 6–8 residues apart, that cross-link in an oxidizing environment to form cystines (disulfide bonds between cysteines). An example of such libraries are those containing or expressing peptides of the form $R^1CX_nCR^2$ wherein $R^1$ is a sequence of 0–10 amino acids, C is cysteine, $X_n$ is a sequence of n variant amino acids (e.g., if all 20 classical amino acids are represented, X means any one of the 20 classical amino acids); n is an integer ranging from 2 to 16; and $R^2$ is a sequence of 0–10 amino acids. $R^1$ and $R^2$ can contain invariant or variant amino acids. Another example is such libraries are those containing or expressing peptides of the form $R^1CX_nR^2$, where $R^1$, X, n, and $R^2$ are as described above; n is preferably 8 or 9. A preferred constrained peptide library, of at least $10^6$ members, consists of peptides comprising the sequence $CX_6C$ (SEQ ID NO:1), wherein C is cysteine, X is any naturally occurring amino acid, and a disulfide bond is formed between the two cysteines. Additional invariant amino acids (e.g., preferably no more than 5–10 amino acids) on either the amino- or carboxy-terminus of $CX_6C$ (SEQ ID NO:1) can be incorporated as part of the peptide in this preferred embodiment. FIG. 10 schematically illustrates such a molecule. The disulfide bridge between the two cysteines acts as a sufficient conformational constraint for the preferred practice of this invention. By way of example, the library is constructed by generating oligonucleotides with the desired degeneracy to code for the peptides and ligating them into vectors of choice. These inserted oligonucleotides are suitable for both use in in vivo genetic expression systems exemplified by phage display, or in vitro translation methods based on coupled transcription and translation from DNA of interest (see below). The creation and use of an exemplary library is described in Section 6.3 hereinbelow. The invention is easily and readily adaptable to other alternative peptide libraries which include short peptides with alternative disulfide scaffolding, for example, comprising the sequence $CX_nCX_mCC$ (SEQ ID NO:11) with two disulfide bridges, wherein n and m are each independently an integer in the range of 2–10, and X is any amino acid. More generally, any peptide library containing members of definite conformation which bind to a target molecule in a specific and identifiable manner may be used.

Further, more general, structurally constrained, organic diversity (e.g., nonpeptide) libraries, can also be used. By way of example, a benzodiazepine library (see e.g., Bunin et al., 1994, Proc. Natl. Acad. Sci. USA 91:4708–4712) may be adapted for use.

Constrained libraries that can be used are also known in the art. For example, PCT Publication No. WO 94/18318 dated Aug. 18, 1994 describes semirigid phage display libraries, in which the plurality of expressed peptides can adopt only a single or a small number of conformations. Examples of such libraries have a pair of invariant cysteine residues positioned in or flanking random residues which, when expressed in an oxidizing environment, are most likely cross-linked by disulfide binds to form cystines. Also disclosed are libraries having a cloverleaf structure by appropriate arrangement of cysteine residues. Also disclosed are libraries with peptides having invariant cysteine and histidine residues positioned within the random residues, or invariant histidines alone within the random residues. TSAR-13 and TSAR-14 are exemplary semirigid libraries disclosed therein.

Other conformationally constrained libraries that can be used include but are not limited to those containing modified peptides (e.g., incorporating fluorine, metals, isotopic labels, are phosphorylated, etc.), peptides containing one or more non-naturally occurring amino acids, non-peptide structures, and peptides containing a significant fraction of γ-carboxyglutamic acid.

As stated above, libraries of non-peptides, e.g., peptide derivatives (for example, that contain one or more non-naturally occurring amino acids) can also be used. One example of these are peptoid libraries (Simon et al., 1992, Proc. Natl. Acad. Sci. USA 89:9367–9371). Peptoids are polymers of non-natural amino acids that have naturally occurring side chains attached not to the alpha carbon but to the backbone amino nitrogen. Since peptoids are not easily degraded by human digestive enzymes, they are advantageously more easily adaptable to drug use. Another example of a library that can be used, in which the amide functionalities in peptides have been permethylated to generate a chemically transformed combinatorial library, is described by Ostresh et al., 1994, Proc. Natl. Acad. Sci. USA 91:11138–11142).

The peptide or peptide portions of members of the libraries that can be screened according to the invention are not limited to containing the 20 naturally occurring amino acids. In particular, chemically synthesized libraries and polysome based libraries allow the use of amino acids in addition to the 20 naturally occurring amino acids (by their inclusion in the precursor pool of amino acids used in library production). In specific embodiments, the library members contain one or more non-natural or non-classical amino acids or cyclic peptides. Non-classical amino acids include but are not limited to the D-isomers of the common amino acids, α-amino isobutyric acid, 4-aminobutyric acid, Abu, 2-amino butyric acid; γ-Abu, ε-Ahx, 6-amino hexanoic acid; Aib, 2-amino isobutyric acid; 3-amino propionic acid; ornithine; norleucine; norvaline, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, Nα-methyl amino acids, fluoro-amino acids and amino acid analogs in general. Furthermore, the amino acid can be D (dextrorotary) or L (levorotary).

By way of example, the incorporation of non-standard or modified amino acids into libraries can be done by taking advantage of concurrent development in reassigning the genetic code (Noren et al., 1989, Science 244:182–188; Benner, 1994, Trend. BioTech. 12:158–163) and the charging of specific tRNAs with the desired amino-acid (Cornish et al., 1994, Proc. Natl. Acad. Sci. USA 91:2910–2914). See also Ibba and Hennecke, 1994, Bio/Technology 12:678–682 (particularly Table I), and references cited therein. These pre-charged tRNAs are then utilized in the in vitro translation system to incorporate the non-standard amino acid into the library of choice. The position of incorporation can be either random (variant) or defined (invariant). The defined case can be chosen to maximize the utility of the resulting placement of the non-natural functional group to maximize either binding properties or the ability to perform structural measurements. Similar techniques may be used to incorporate non-standard amino acids into the peptides.

In a specific embodiment, an iterative approach to library construction can be taken, as structural information on the mode of binding to a given target is obtained. For example, information from structural analysis can be used to make libraries with library members containing chemical backbones that match known chemical scaffolds, enhance solubility or membrane permeability, reduce effect of water on structure, and incorporate other physical parameters suggested by structural analysis. Use of algorithmically optimized library inserts can be used to increase the chances of finding binders of interest (see e.g., Arkin and Youvan, 1992, Bio/Technology 10:297–300).

In other embodiments, the following can be used to improve library use in both phage and bacterial systems: production of libraries in bacteria which overproduce the chaperonins GroES and GroEL (Soderlind et al., 1993, Bio/Technology 11:503–507), and production in *E. coli* strains which prevent degradation in the periplasmic space (Strauch and Beckwith, 1988, Proc. Natl. Acad. Sci. USA 85:1576–1580; Lipinska et al., 1989, J. Bacteriology 171:1574–1584). Purified cofactors such as GroES and GroEL could also be directly added to an in vitro expression and selection system.

5.3. SCREENING OF DIVERSITY LIBRARIES

Once a suitable diversity library has been constructed (or otherwise obtained), the library is screened to identify binders having binding affinity for the target. Screening is done by contacting the diversity library members with the target molecule under conditions conducive to binding and then identifying the member(s) which bind to the target molecule. Screening the libraries can be accomplished by any of a variety of commonly known methods. See, e.g., the following references, which disclose screening of peptide libraries: Parmley and Smith, 1989, Adv. Exp. Med. Biol. 251:215–218; Scott and Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. No. 5,096,815, U.S. Pat. No. 5,223,409, and U.S. Pat. No. 5,198,346, all to Ladner et al.; Rebar and Pabo, 1993, Science 263:671–673; and PCT Publication No. WO 94/18318. See also the references cited in Section 5.2 hereinabove (disclosing libraries) regarding methods for screening.

Screening can be carried out by contacting the library members with an immobilized target molecule and harvesting those library members that bind to the target. Examples of such screening methods, termed "panning" techniques are described by way of example in Parmley and Smith, 1988, Gene 73:305–318; Fowlkes et al., 1992, BioTechniques 13:422–427; PCT Publication No. WO 94/18318; and in references cited hereinabove. In panning methods that can be used to screen the libraries, the target molecule can be immobilized on plates, beads, such as magnetic beads, sepharose, etc., or on beads used in columns. In particular embodiments, the immobilized target molecule has incorporated an "affinity tag," as described above, which can be used to effect immobilization by attaching the tag's binding partner to the desired solid phase.

In one embodiment, the primary method of selecting from libraries is the use of solid phase plastic affinity capture to immobilize the target molecule prior to its use in the selection (screening) process. This method can be improved upon to increase throughput, selectivity and specificity. Solid phase plastic supports can be replaced with magnetic particles. In phage-based systems, large beads can be used, but these are not believed to be suitable, due to steric hindrance, for use in bacterial systems. This steric hindrance can be avoided by using high gradient magnetic cell separation with small particles (<<0.5 $\mu$m) (Miltenyi et al., 1990, Cytometry 11:231–238).

In a specific embodiment involving the use of a peptide phage display library, selection of a binder protein expressed on the surface of a bacteriophage thus selects both the binder protein and the DNA that encodes it (the DNA being within the phage particle). Following binding between the target molecule and library members, phage are released from a solid support on which the binder-target molecule complex is immobilized, and are amplified, e.g., by infecting *E. coli* and propagating each isolated binding phage. Repeating this process of affinity capture and amplification allows those peptides which bind with the highest affinity to the target molecule to be selectively enriched from the original library.

In one particular embodiment, presented by way of example but not limitation, a phage display library can be screened as follows using magnetic beads (see PCT Publication No. WO 94/18318):

Target molecules are conjugated to magnetic beads, according to the instructions of the manufacturers. The beads are incubated with excess bovine serum albumin (BSA), to block non-specific binding. The beads are then washed with numerous cycles of suspension in phosphate buffered saline (PBS) with 0.05% Tween® 20 and recovered by drawing a strong magnet along the sides of a plastic tube. The beads are then stored under refrigeration, until use.

An aliquot of a library is mixed with a sample of resuspended beads, at 4° C. for a time period in the range of 2–24 hrs. The magnetic beads are then recovered with a strong magnet and the liquid is removed by aspiration. The beads are then washed by resuspension in PBS with 0.05% Tween® 20, and then drawing the beads to the tube wall with the magnet. The contents of the tube are removed and washing is repeated 5–10 additional times. 50 mM glycine-HCl (pH 2.0), 100 μg/ml BSA solution is added to the washed beads to denature proteins and release bound phage. After a short incubation, the beads are drawn to the side of the tubes with a strong magnet, and the liquid contents are then transferred to clean tubes. 1 M Tris-HCl (pH 7.5) or 1 M $NaH_2PO_4$ (pH 7) is added to the tubes to neutralize the pH of the phage sample. The phage are then diluted, e.g., $10^{-3}$ to $10^{-6}$, and aliquots plated with E. coli DH5αF' cells to determine the number of plaque forming units of the sample. In certain cases, the platings are done in the presence of XGal and IPTG for color discrimination of plaques (i.e., lacz+ plaques are blue, lacZ− plaques are white). The titer of the input samples is also determined for comparison.

Alternatively, as yet another non-limiting example, screening a diversity library of phage expressing peptides can be achieved by panning using microtiter plates (see PCT Publication No. WO 94/18318) as follows:

The target molecule is diluted and a small aliquot of target molecule solution is adsorbed onto wells of microtiter plates (e.g. by incubation overnight at 4° C.). An aliquot of BSA solution (1 mg/ml, in 100 mM $NaHCO_3$, pH 8.5) is added and the plate incubated at room temperature for 1 hr. The contents of the microtiter plate are flicked out and the wells washed carefully with PBS-0.05% Tween® 20. The plates are repeatedly washed free of unbound target molecules. A small aliquot of phage solution is introduced into each well and the wells are incubated at room temperature for 2–24 hrs. The contents of microtiter plates are flicked out and washed repeatedly. The plates are incubated with wash solution in each well for 20 minutes at room temperature to allow bound phage with rapid dissociation constants to be released. The wells are then washed five more times to remove all unbound phage.

To recover the phage bound to the wells, a pH change is used. An aliquot of 50 mM glycine-HCl (pH 2.0), 100 μg/ml BSA solution is added to the washed wells to denature proteins and release bound phage. After 10 minutes at 65° C., the contents are then transferred into clean tubes, and a small aliquot of 1 M Tris-HCl (pH 7.5) or 1M $NaH_2PO_4$ (pH 7) is added to neutralize the pH of the phage sample. The phage are then diluted, e.g., $10^{-3}$ to $10^{-6}$ and aliquots plated with E. coli DH5αF' cells to determine the number of the plaque forming units of the sample. In certain cases, the platings are done in the presence of XGal and IPTG for color discrimination of plaques (i.e., lacZ+ plaques are blue, lacZ− plaques are white). The titer of the input samples is also determined for comparison (dilutions are generally $10^{-6}$ to $10^{-9}$).

By way of another example, diversity libraries expressing peptides as a surface protein of either a particle or a host cell, e.g., phage or bacterial cell, can be screened by passing a solution of the library over a column of the target molecule immobilized to a solid matrix, such as sepharose, silica, etc., and recovering those particles or host cells that bind to the column after washing and elution.

In yet another embodiment, screening a library can be performed by using a method comprising a first "enrichment" step and a second filter lift step as described in PCT Publication No. WO 94/18318.

Several rounds of serial screening are preferably conducted. In a particularly preferred aspect, each round is varied slightly, e.g., by changing the solid phase on which immobilization occurs, or by changing the method of immobilization on (e.g., by changing the linker to) the solid phase. When using a phage display library, the recovered cells are then preferably plated at a low density to yield isolated colonies for individual analysis. By way of example, the following is done: The individual colonies are selected, grown and used to inoculate LB culture medium containing ampicillin. After overnight culture at 37° C., the cultures are then spun down by centrifugation. Individual cell aliquots are then retested for binding to the target molecule attached to the beads. Binding to other beads, having attached thereto a non-relevant molecule, can be used as a negative control.

In a specific embodiment, different rounds of screening can respectively involve selection against targets in primarily their purified form, and then in their natural state (e.g., on the surface of a mammalian cell) (see, e.g., Marks et al., 1993, Bio/Technology 11:1145–1149, describing selection against cell surface blood group antigens).

In other examples, subsequent rounds of screening can involve immobilization of the target molecule by attachment at different ends (e.g., amino or carboxy-terminus) of the target molecule to a solid support, or presentation of library members by attachment to or fusion at different ends of the library members.

By way of other examples of screening methods that can be used, genetic selection methods can be adapted for screening of libraries, or can be used in a recursive scheme. Thus, in a specific aspect, the invention provides screening methods in which methods allowing high throughput and diversity screening (e.g., screening phage display or polysome libraries against a ligand) are utilized in initial rounds, with subsequent rounds employing a genetic selection technique, in which the presence of a binder of appropriate specificity increases the activity of or activation of a transcriptional promoter or origin of replication. Genetic selection techniques that can be adapted for use (e.g., by inserting random oligonucleotides in the test plasmid) include the two-hybrid system for selecting interacting proteins in yeast, replicative based systems in mammalian cells, and others (see, e.g., Fields & Song, 1989, Nature 340:246–246; Chien et al., 1991, Proc. Natl. Acad. Sci. USA 88:9578–9582; Vasavada et al., 1991, Proc. Natl. Acad. Sci. USA 88:10686–10690). Thus, in a specific embodiment, compounds are produced as fusion proteins, and contacted with a different fusion protein comprising a target fused to another molecule, in which specific binding of the fusion proteins to each other results in an increase in activity or activation of a transcriptional promoter or an origin of replication. In a specific embodiment, a genetic selection method is used in a later round of screening to either select directly for a library member that binds to a target molecule, or to select a library member that competitively inhibits binding of a ligand to the target molecule.

Several exemplary methods for screening a phage/phagemid library are presented by way of example in Section 6.4 hereinbelow. An exemplary method for screening a polysome-based library is presented in Section 6.3.3 hereinbelow.

Once binders are selected from a diversity library which bind to a target molecule of interest, additional assays are preferably, although optionally, performed, including but not limited to those described below. Thus, in vivo or in vitro assays can be performed to test whether binding of a binder to the target molecule affects the target molecule's biological activity; binders that exert such an effect are preferred for use in subsequent steps of the invention. Alternatively, or in addition, competitive binding assays can be carried out to test whether the binder competes with other binders or with a natural ligand of the target molecule, for binding to the target molecule; binders that compete with each other, and that compete with the natural ligand, are preferably selected for use in subsequent steps of the invention. Alternatively, or in addition to the above assays, the binding affinity of binders for the target molecule is determined, by standard methods, or by way of example, as described in Section 6.5 infra. Binders of the highest affinity are preferred for use in subsequent steps of the invention.

5.4. DETERMINING THE SEQUENCE OR CHEMICAL FORMULA OF BINDERS

Many of the references cited in Section 5.2 and 5.3 hereinabove, which disclose library construction and/or screening, also disclose methods that can be used to determine the sequence or chemical formula of binders isolated from such libraries. By way of example, a nucleic acid which expresses a binder can be identified and recovered from a peptide expression library or from a polysome-based library, and then sequenced to determine its nucleotide sequence and hence the deduced amino acid sequence that mediates binding. (In an instance wherein the sequence of an RNA is desired, cDNA is preferably made and sequenced.) Alternatively, the amino acid sequence of a binder can be determined by direct determination of the amino acid sequence of a peptide selected from a peptide library containing chemically synthesized peptides. In a less preferred aspect, direct amino acid sequencing of a binder selected from a peptide expression library can also be performed.

Nucleotide sequence analysis can be carried out by any method known in the art, including but not limited to the method of Maxam and Gilbert (1980, Meth. Enzymol. 65:499–560), the Sanger dideoxy method (Sanger et al., 1977, Proc. Natl, Acad. Sci. U.S.A. 74:5463), the use of T7 DNA polymerase (Tabor and Richardson, U.S. Pat. No. 4,795,699; Sequenase™, U.S. Biochemical Corp.), or Taq polymerase, or use of an automated DNA sequenator (e.g., Applied Biosystems, Foster City, Calif.).

Direct determination of the chemical formulas of non-peptide or peptide binders can be carried out by methods well known in the art, including but not limited to mass spectrometry, NMR, infrared analysis, etc.

In preferred aspects involving certain types of libraries well known in the art, sequencing or the use of known analytic techniques for chemical formula determination will not be necessary. In some such libraries, the identity and composition of each member of the library is uniquely specified by a label or "tag" which is physically associated with it and hence the compositions of those members that bind to a given target are specified directly (see, e.g., Ohlmeyer et al., 1993, Proc. Natl. Acad. Sci. USA 90:10922–10926; Brenner et al., 1992, Proc. Natl. Acad. Sci. USA 89:5381–5383; Lerner et al., PCT Publication No. WO 93/20242). In other examples of such libraries, the library members are created by step wise synthesis protocols accompanied by complex record keeping, complex mixtures are screened, and deconvolution methods are used to elucidate which individual members were in the sets that had binding activity, and hence which synthesis steps produced the members and the composition of individual members (see, e.g., Erb et al., 1994, Proc. Natl. Acad. Sci. USA 91:11422–11426).

Step 2 of the invention provides as output N binding library members (binders) and their sequences or chemical formulas.

5.5. CANDIDATE PHARMACOPHORE SELECTION

The prior diversity library screening, step 2, determines a set of size N of specifically binding members from one or more diversity libraries. While the binders are preferably but not necessarily isolated from one or more diversity libraries (e.g., binders need not be isolated from diversity libraries; known binders can be simply provided), the following description shall refer to the preferred embodiment wherein diversity library members are the binders. It will be apparent that the description is also readily applicable to binders that are not isolated from diversity libraries.

The pharmacophore responsible for the library member binding is preferably determined by an overall select and test method in this and subsequent steps. In general, a pharmacophore is specified by the precise electronic properties on the surface of the binder that causes binding to the surface of the target molecule. In the preferred embodiment, these properties are specified by the underlying, causative, chemical structures. Chemical structures are specified generally by groups such as —$CH_2$—, —COOH, and —$CONH_2$. The preferred pharmacophore representation consists of a specification of the underlying chemical groups and their geometric relations. The more precisely the geometric relations are specified, the more preferred. In preferred but not limiting aspects, the geometric relations are precise to at least 0.50 Å, and most preferably, at least 0.25 Å. A pharmacophore will usually comprise 2 to 4 of such groups, with 3 being typical. However, for complex protein recognition targets, a pharmacophore may comprise a greater number of groups. For example, it is possible that the entire 6 amino acid sequence, —$X_6$—, may be needed for a member of the preferred $CX_6C$ library to bind to complex targets, in which case the pharmacophore includes the entire binder.

Figure 11:
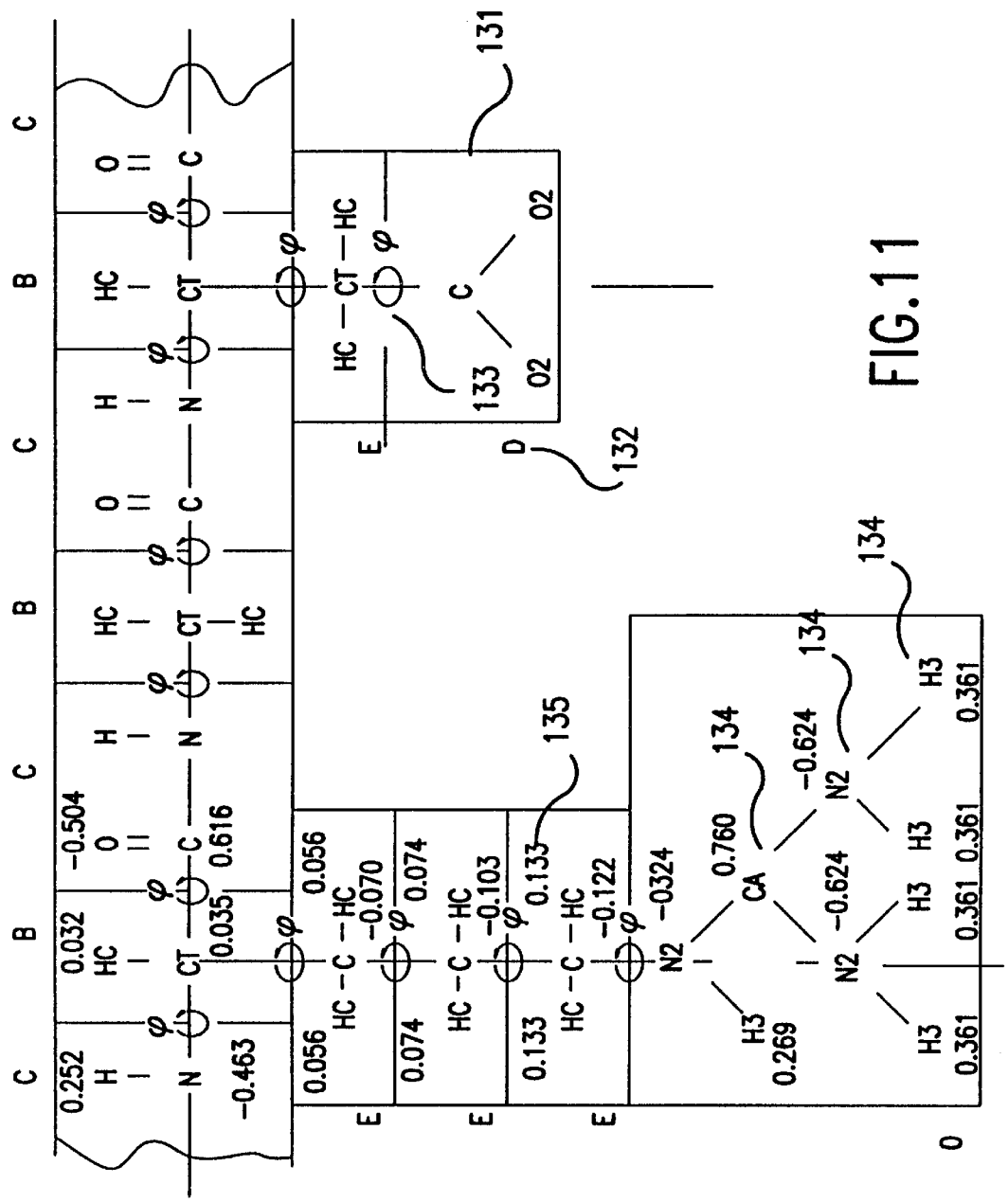
FIG. 11 is additional detail of peptide memory representation used in the method of FIG. 8.

Considering by way of example, the case of binders isolated from the preferred library, of sequence $CX_6C$, the chemical groups defining a peptide pharmacophore are terminal groups on amino acid side chains. Typically, therefore, a sequence of two to four contiguous amino acids will contain the pharmacophore of interest. For example, FIG. 11 illustrates an Arginine-Glycine-Aspartate sequence forming a well known platelet aggregation inhibiting pharmacophore, which is defined by the positions and orientations of the adjacent —$CN_3H_4$, —$C\alpha H_2$—, and —COOH groups. Pharmacophores formed by discontiguous amino acids are not likely to occur in the preferred library due to the conformational constraint on the short peptide imposed by the disulfide bridge.

The selection step determines candidate amino acid sequences in each binder that define a candidate pharmacophore by the positions of their terminal groups. Candidate selection depends substantially only on the chemical structures of the amino acid side chains and terminal groups (only very rarely on backbone groups). Geometric structure is not yet available and cannot be used for candidate selection. In the preferred embodiment, amino acids are grouped into homologous groups defined by group members having similar side chain structure and activity (see infra). Candidate pharmacophores are found by searching the sequences of the N binders for short sequences of homologous amino acids. This search will produce at least one candidate, because all the binders share the actual pharmacophore. Several candidates will usually be found since geometric information is ignored, and the search is thereby underdetermined.

Figure 2A:
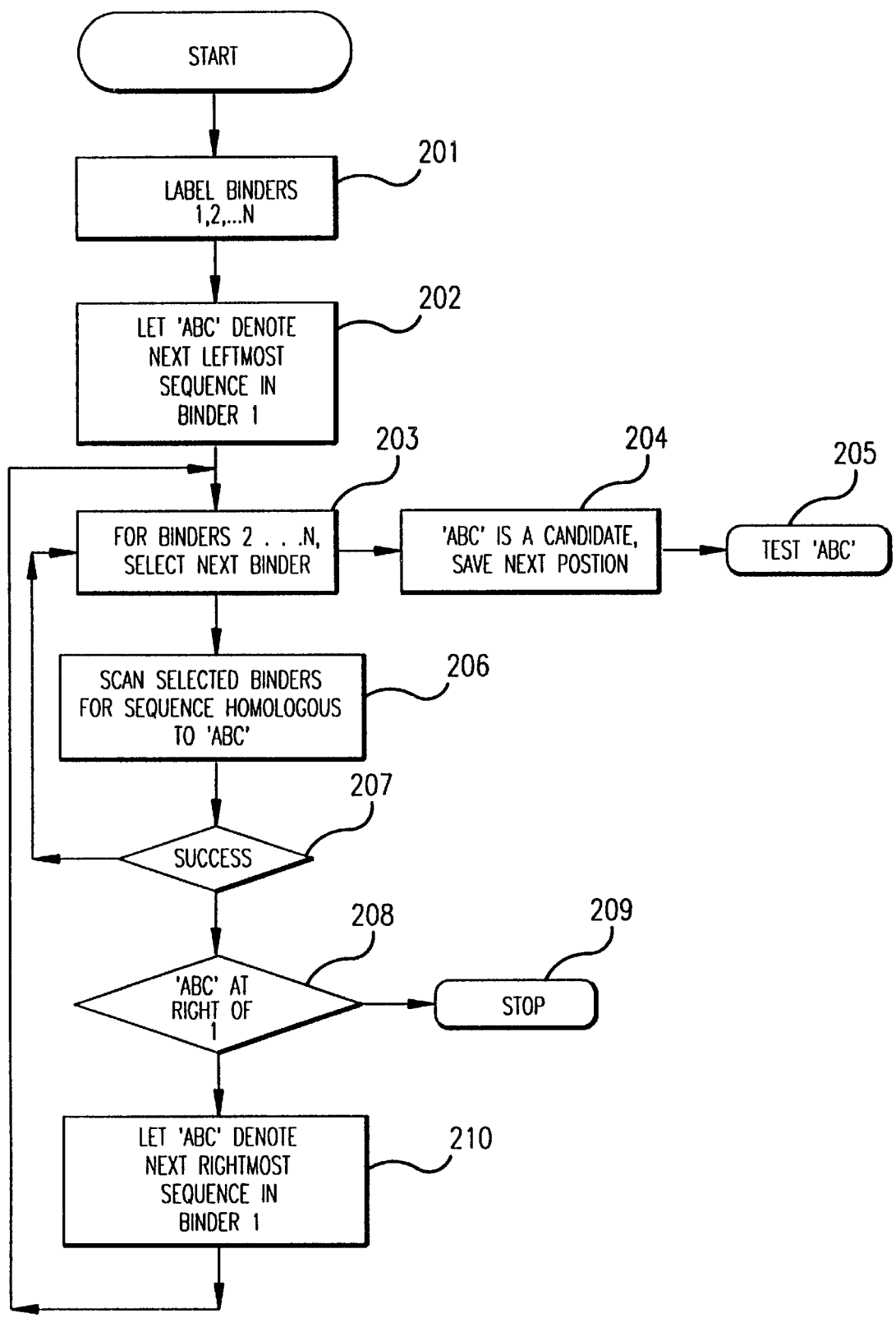
FIGS. 2A and 2B are more detail for the step of FIG. 1 for selecting candidate pharmacophore structures.

FIG. 2A illustrates an exemplary method of performing the search for homologous sequences. Although this method is illustrated as searching for homologous contiguous sequences of length 3, it is easily adaptable to search for homologies of other lengths and also for discontiguous homologous sequences. If no candidate pharmacophores of length 3 have a consistent consensus structure, then pharmacophores of length 2, 4, or longer or discontiguous sequences must be searched and selected for test. For some complex targets, the pharmacophore may include the entire variable part of the library member. The exemplary method is a simple depth-first search for matching amino acid strings. More sophisticated string search methods are known and are equally applicable to this invention.

The method begins with the administrative steps 201 and 202 of labeling the binders with integers from 1 to N and assigning the string variable 'ABC' to the next left most sequence of three amino acids to test in binder 1. If this is the first candidate selection, 'ABC' will be at the left most position in binder 1. If prior candidates have been selected, 'ABC' will be assigned one amino acid to the right of its prior assignment. The FOR loop, formed by steps 203, 206, and 207, then selects each binder from 2 to N for scanning for a sequence homologous to 'ABC'. Step 203 does loop administration. Step 206 does the scanning. If homologous sequences are found, test 207 loops back to scan the next binder. If homologous sequences have been found in all binders from 2 to N, the loop exits at step 204. In this case 'ABC' is a string in binder 1 which is homologous to other strings in all remaining binders and is thus a candidate pharmacophore. The method exits at 205 for this candidate to be structured and tested for whether it is the actual pharmacophore. If a binder does not have a sequence homologous to 'ABC', then this string is not a candidate. In this case, test 208 determines if 'ABC' is at the right end of binder 1. If so, there are no more homologies to test for and the method exits at 209. If not, then 'ABC' is advanced one amino acid to the right 210 and the scan of all binders is repeated beginning at 203.

Figure 2B:
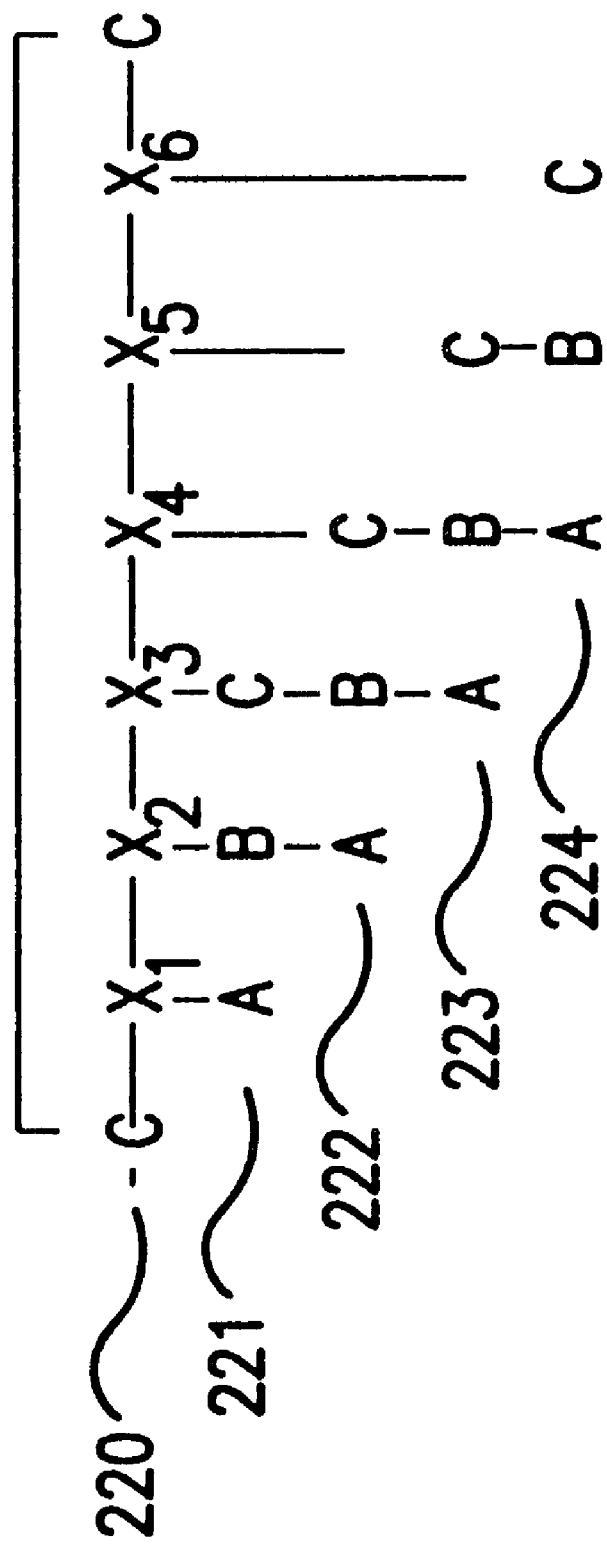

FIG. 2B illustrates how string variable 'ABC' is scanned across binder 1, represented schematically by 220. First, 'ABC' is assigned to $X_1X_2X_3$ at 221, then to $X_2X_3X_4$ at 222, to $X_3X_4X_5$ at 223, and finally to $X_4X_5X_6$ at 224.

Given an assignment to 'ABC', step 206 scans each other binder, for example binder K with K>1, for homologous sequences. This is simply done by comparing all contiguous substrings of binder K with 'ABC' to determine if they are homologous. They are homologous if corresponding amino acids in the substring and 'ABC' are homologous. In turn, two amino acids are homologous if they satisfy established homology rules. Each homologous sequence found in binder K defines a separate candidate pharmacophore, if sequences homologous to 'ABC' are found in all other binders.

In a case where discontiguous homologous sequences are sought, 'ABC' is assigned to amino acids in discontiguous positions in binder 1 and then compared for homologies to amino acids in the same relative positions throughout the other binders.

Various rules of amino acid homology may be used in this invention. In the preferred embodiment, amino acids are homologous if they are found in the same class of amino acids, based on side chain activity (see Lehninger, *Principles of Biochemistry*, (1982), chap. 5). Preferred homologous groups of amino acids are as follows. The nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. The foregoing classes may be modified by those skilled in chemical arts to create finer classifications. For example, phenylalanine and tryptophan could be placed in a separate aromatic nonpolar group. Further, homology rules could depend on amino acid sequence, such as by dividing contiguous doublets or triplets of amino acids into homology groups.

The invention is not limited to the above-described exemplary method of selecting candidate pharmacophores. Any automatic method of selecting candidates that depends only on chemical structure of binder library members, preferably expressed in terms of building block composition and sequence, can be used. For example, in the case of the preferred $CX_6C$ library, candidates could be selected by a clustering analysis performed on the entire amino acid string in a multi-dimensional space.

This above method of selecting candidate pharmacophores is not limited to the preferred $CX_6C$ diversity library. For example, this method is immediately applicable to any diversity library having members comprising building blocks linked by a linear backbone by simply specifying rules of homology appropriate for the building blocks. These homology rules would group building blocks presenting similar structure and reactivity to targets. This method then selects candidates comprising sequences of homologous building blocks present on all the binding library members. If the library members do not have a linear backbone, a related candidate selection method can be used. In this case, the search for homologous building blocks would need to be confined to adjacent building blocks. Adjacent building blocks in this case are those building blocks brought physically close by whatever chemical structures form the library members (instead of simply being linearly adjacent on a backbone). An adjacency determination would be specific to the particular chemical structure and would be algorithmicly specified. In addition appropriate rules of homology would be specified. The method would then select candidates comprising groups of adjacent, homologous building blocks, a group being present on each binding library member.

The above-described step is the selection step of the overall select and test method. Distance measurements and Monte Carlo structuring, steps 4 and 5, determine a consensus pharmacophore structure for the candidate, if possible. If a consensus is found, the candidate is the actual pharmacophore. If a consensus is not found, this selection step must be revisited, and a new candidate selected for test.

5.6. INTRAMOLECULAR DISTANCE MEASUREMENTS

Having obtained N binders, their chemical building block structures (chemical formula or primary sequence), and the identification of a candidate pharmacophore in each binder, steps 4 and 5 of the method of this invention cooperatively determine a precise spatial structure for the candidate pharmacophore (if it exists; if not, a new candidate pharmacophore is selected.) In the preferred (but not limiting) embodiment of this invention, N members of the $CX_6C$ library that specifically bind to the protein target of interest have been screened; their sequences determined; and a candidate pharmacophore consisting of homologous triplets (more generally from 2 to 6 mers) of amino acids has been determined in each binder.

Step 4 measures one or more strategic distances, preferably no more than 10–20, e.g., 1–10 or, more preferably, 1–5 interatomic distances are measured. The remainder of the structure is determined in subsequent steps, other than by direct measurement. The interatomic distances measured in step 4 are preferably with an accuracy of at least 2 Å, more preferably at least 1 Å or 0.5 Å or 0.25 Å, and most preferably at least 0.05 Å. Thus, in a preferred but not limiting embodiment, distances in the pharmacophore are specified to at least approximately 0.25 Å. Step 5, using the CCMBC computational method, then completes determination of the pharmacophore structure at a high resolution and the structures of the rest of the binder molecules with a secondary resolution. Having a high resolution structure for the pharmacophore of interest is orders of magnitude more useful than having a low resolution structure for an entire binder. Consequently, steps 4 and 5 focus resources on the former problem.

A distance measurement method is preferred for use if it meets certain conditions, as follows. First, accuracy of distance measurements is preferably better than at least 0.25 Å for distances on the order of those between amino acids in a peptide. Second, measurement conditions preferably approximate target binding conditions, i.e., are approximately physiologic. For example, crystallization, which may induce conformational changes, is preferably avoided. Also, the employed measurement methods preferably allow one binder sample to be measured when dry, when hydrated and when bound to the target molecule of interest, thereby observing the effects of water and conformational changes on binding. Third, the measurement method is preferably quick and inexpensive.

Important advantages are conveyed by these certain conditions. First, as the method of the invention determines high resolution pharmacophore structures, use of distances less accurate than the intended results would almost certainly result in decreased resolution. Second, as the CCMBC structure determination method approximates the structural effects of hydration and target binding, use of accurate distances including the physical effects of hydration or binding helps increase the resolution of the computational results. These distances as used in the CCMBC method pull the binder structures towards a more accurate representation both of the bound, hydrated pharmacophore and also of the remainder of the binder molecule without a computationally burdensome inclusion of water molecules and without knowledge of the target molecule's structure.

REDOR NMR is the preferred method of distance determination. REDOR is a solid phase NMR technique which directly measures the inter-nuclear dipole-dipole interaction strength between two spin ½ nuclear species, denoted $D_{AB}$ where A and B are the two nuclear species measured. The internuclear distance between A and B is simply determined from $D_{AB}$ by the following equation:

$$D_{AB} = \frac{h\gamma_A\gamma_B}{2\pi R_{AB}^3} \quad (1)$$

where $R_{AB}$ is the inter-nuclear distance, h is Planck's constant, and $\gamma_A$, and $\gamma_B$ are the respective gyromagnetic ratios of nuclei A and B. REDOR is typically accurate to less than 0.05 Å and can generally measure distances up to about 8 Å.

Any two nuclear species observable and resolvable by NMR methods and, preferably, adaptable to chemical inclusion in the diversity library members of interest, may be the basis of REDOR measurements. Although the subsequent description is often directed to distance determinations between $^{13}C$ and $^{15}N$ nuclei in members of a preferred library comprising the sequence $CX_6C$, this invention is not so limited. One skilled in the art can readily adapt the method for use in making measurements of other types of molecules (e.g., peptides and nonpeptides); additionally, other nuclear species may be used. Other common spin ½ species that can be used include but are not limited to $^{31}P$ and the halogen $^{19}F$.

General references on NMR techniques are Slichter, *Principles of Magnetic Resonance,* Berlin, Springer-Verlag, (1989) and Mehring, *High Resolution NMR in Solids,* Berlin, Springer-Verlag (1983). REDOR references include Gullion et al., *Rotational-echo double-resonance NMR,* J. Magn. Res. 81:196–200 (1989); Pan et al., *Determination of C-N internuclear distance by rotational-echo double-resonance NMR of solids,* J. Magn. Res. 90:330–40 (1990); Garbow et al., *Determination of the molecular conformation of melanostatin using 13C, 15N-REDOR NMR spectroscopy,* J. Am. Chem. Soc. 115:238–44 (1993), all of which are incorporated herein by reference.

Other solid phase NMR techniques are applicable but less preferred. These include but are not limited to those disclosed in Kolbert et al., *Measurement of internuclear distances by switched angle spinning,* J. Physical Chemistry 98:7936 et seq. (1994), and in Raleigh et al., *Rotational Resonance NMR,* Chemical Physics Letters 146:71 (1988). These techniques measure homonuclear distances only to 0.5 Å accuracy and are less accurate than REDOR. Liquid phase NMR techniques of NOE (nuclear overhausser) and COESY (correlation enhanced spectroscopy) can also be used but are less preferred. They require complex interpretation to obtain comparable distance accuracy greater than 0.5 Å in small molecules with complete rotational freedom.

X-ray crystallography can also be used, although it is much less preferred, since crystallization may induce conformational changes in the binder, and since binding to the target molecule may be necessary for crystallization.

In the case of REDOR measurements of the heteronuclear distances between $^{13}C$ and $^{15}N$, $^{13}C$ and $^{15}N$ are introduced ("labeled") at the positions between which a distance measurement is needed. The preferred embodiment of the invention measures the $^{15}N$ NMR resonance. Since nearly all the $^{15}N$ signal will originate with nuclear labels, very little background signal due to natural abundance nuclei need be accounted for. Alternatively, the $^{13}C$ resonance may be measured, in which case the natural abundance background is subtracted from the measurements.

Since REDOR depends on observing the internuclear dipole-dipole interaction, the binder being measured should be substantially stationary on the time scale of the NMR signal. The measurement system preferably ensures this condition. The substrate holding the binder to be measured can be chosen so as to restrain binder motion, or the measured sample may be cooled to restrain motion, or, alternatively, the binder may be bound to its target molecule in order to restrain its motion.

Figure 3:
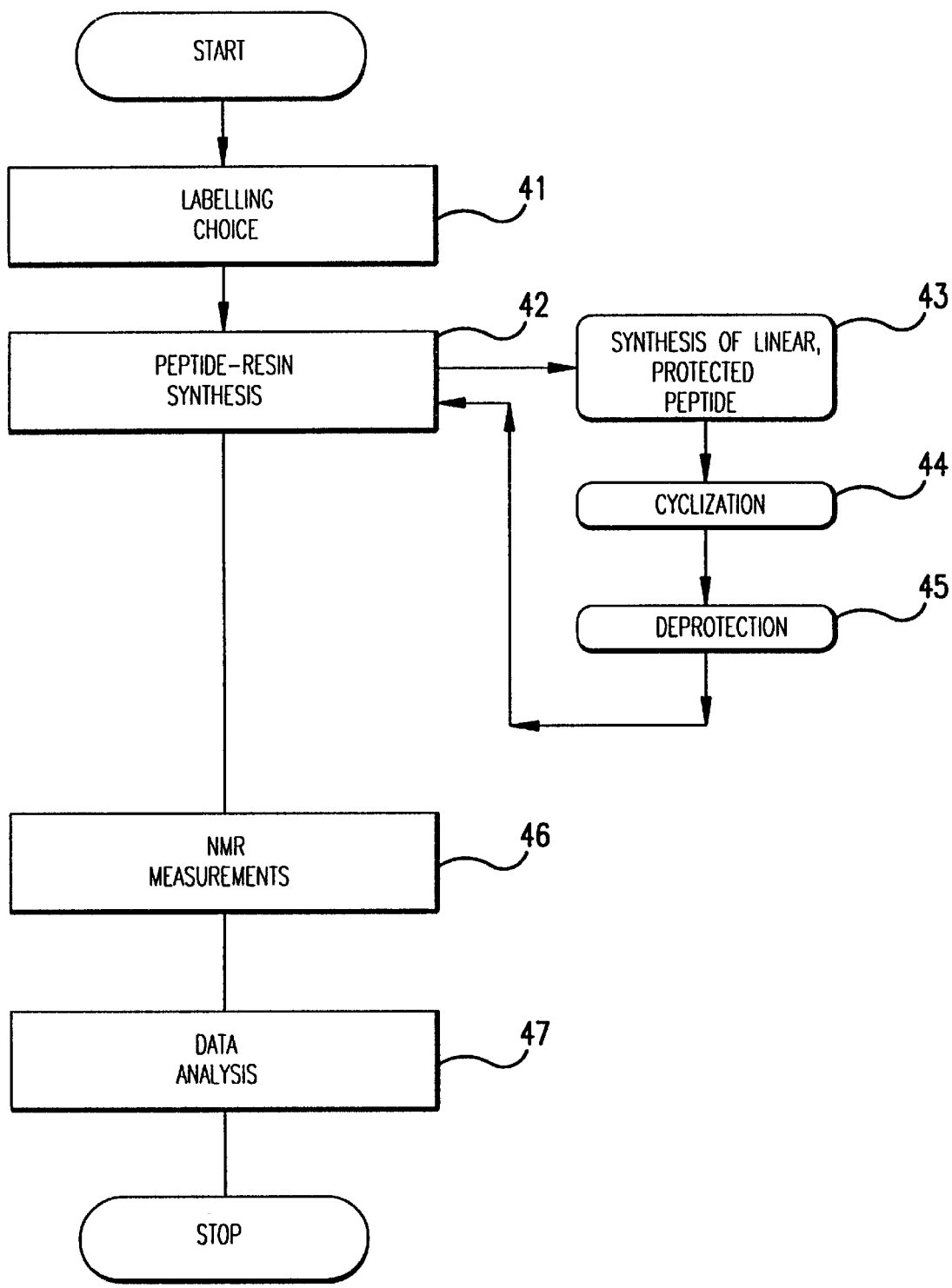
FIG. 3 is more detail for the step of FIG. 1 for preforming distance measurements.

Further details of the REDOR distance measurements will make reference to FIG. 3. This illustrates the measurement method for one labeling of one binder, which is repeated if the binder requires multiple labelings and also is repeated for each binder. Subsequent description will focus on only one binder.

Step 41 chooses a binder labeling. Labeling is preferably done to obtain the most information about the pharmacophore consistent with chemical labeling opportunities and available labeled amino acids. Backbone labeling, for example, labels the amide N of one amino acid and one of the backbone C's of a next adjacent or more distant amino acid. Backbone labeling is typically done in the backbone in the vicinity of the candidate pharmacophore. It might also be done away from a candidate pharmacophore to confirm a previously determined structure as described for step 6. Side chain labeling strategies vary with the chemical opportunities offered by the candidate pharmacophore. If a terminal N is available, an adjacent side chain or backbone C can be labeled. If not, the side chain C and backbone amino N can be labeled. Side chain labeling is preferably on side chains in the candidate pharmacophore. Preferred labeling in the candidate pharmacophore is either a backbone amino N and a nearby backbone C or a side chain C or, if available, a side chain amino N and an adjacent or nearby side chain C.

In an alternative embodiment, to get the most structural information on the binders, these labelings are designed to select the actual major conformation from known possible conformations. For example, if it is known from preliminary determinations that a binder may exist in one of a few, e.g. two, major backbone or side chain folding patterns, the labelings are chosen to distinguish these conformations. Nuclear pairs labeled for measurement are preferably those that have significantly different distances in the possible conformations.

Multiple labeling of one binder to determine multiple distances at once is possible, for example, by including one $^{13}C$ and several $^{15}N$ nuclei, or vice versa, in one labeled molecule. Multiple labeling is limited, however, as is obvious to one skilled in the NMR arts, by chemical shifts of the various nuclear resonances. REDOR measurement of multiple $^{15}N$–$^{13}C$ distances requires that each spectroscopically observed $^{15}N$ or $^{13}C$ resonance have a distinguishable chemical shift. If these conditions are not met, several separately labeled versions of the binder are prepared and measured, one for each internuclear distance sought.

Step 42 synthesizes the labeled binder after a labeling has been determined by applying these preferences and rules. In an embodiment wherein the binder is a peptide, variously labeled $^{13}C$ or $^{15}N$ labeled amino acid reagents for the synthesis of the labeled binder are widely available from commercial sources. A preferred supplier is Isotec Inc. (Miamisburg, Ohio). Other commercial sources include MSD Isotopes (Montreal, Canada) and Sigma Chemical Co. (St. Louis, Mo.). Step 42 has three substeps: linear peptide synthesis 43, cyclization 44 (by forming the disulfide bond), and deprotection of the side groups 45. Synthesis and side chain deprotection are performed by solid phase peptide synthesis using standard Boc (tert-butoxycarbonyl) and Fmoc (9-fluorenylmethyloxycarbonyl) chemistry. Exemplary references for this method are Merrifield, J. Amer. Chem. Soc., vol 85, pp 2149 et seq. (1963); Caprino et al., J. Amer. Chem. Soc. (1970); and Stewart et al., *Solid Phase Peptide Synthesis,* Berlin, Springer-Verlag (1984), which are herein incorporated by reference. Cyclization is by conventional mild oxidation, well known in the chemical arts. The method of these steps is detailed in Example 2 supra.

To obtain accurate REDOR NMR measurements, the binder sample is preferably highly purified. Accordingly, it is preferable that the sample be at least 90% pure (but not necessary if spurious NMR signals can be discriminated), and even more preferable that the sample be at least 95% pure. Such pure samples can be obtained as follows. In a first synthesis method, the binder peptide is synthesized directly on the substrate to be used in the subsequent NMR measurements. In this case particular care is preferably taken with the standard solid phase synthesis steps of Example 2. By way of example, synthesis reagents should be pure, adequate time should be allowed for diffusion of reagents and solvents throughout the interstices of the substrate resin, and between steps, prior reagents should be thoroughly washed from the resin before new reagents applied. That the purity, reaction time, and washings are adequate is gauged by subsequent analysis. An aliquot of the resulting peptide-resin is taken, the peptide is cleaved (Example 2) and its purity analyzed by mass spectroscopy or high performance liquid chromatography (HPLC).

In a second synthesis method, the peptide can be synthesized on any convenient solid phase substrate in a standard manner and then cleaved from the substrate. The peptide is purified by standard methods (e.g., HPLC) and then attached to the NMR measurement substrate. The attachment can be done by any methods known in the art, preferably at either the amino- or carboxy-terminus, e.g., by condensation of the free carboxy terminal group on the peptide with an amino labeled resin, with the attachment step preceding deprotection of any side chain carboxy groups on the peptide; by use of heterofunctional linker groups, etc.

Great care is preferably exercised in forming the binder-substrate used for the REDOR NMR measurements. This invention is also directed to binder-substrates suitable to precise REDOR NMR measurements in the following environmental conditions: dry unbound, hydrated unbound, and bound to its molecular target molecule (e.g., in lyophilized or hydrated forms).

For any binder and any NMR measurement substrate utilized, the substrate should restrain the attached binder sufficiently so that binder motion will not average out the dipole-dipole interactions necessary for the REDOR measurement. Generally, this requires that the frequency of motion of the binder be less than the frequency of the dipole-dipole interaction being observed, which varies with the nuclear species being observed and the measurement distance. For $^{13}C$–$^{15}N$ observations to 2.5 Å the binder motion frequency should be less than approximately 200 Hz; for observations to 5 Å, less than approximately 30–50 Hz; and for observations beyond 5 Å, less than approximately down to 10 Hz. The more polar the substrate, such as glass beads or p-MethylBenzhydrilamine ["mBHA"] resin, the more are polar attached binders (such as are many peptides) restrained. Less polar substrates, such as polystyrene resin, provide less restraints for polar binders. In an embodiment wherein a peptide comprising the sequence $CX_6C$ is bound to an mBHA resin with an glycine residue serving as a linker to a binding site on the resin, probably no additional steps need be taken for 2.5 Å measurements. Additional steps that can be used, if needed, to slow binder motions include cooling the measurement sample to, for example, liquid $N_2$ temperatures (approximately 77° K) or binding to a large, relatively immobile target molecule.

Second, the net hinder density is important and typically is adjusted. The substrate preferably has an adjustable number of binder synthesis sites or binding sites per unit of substrate surface area. Too high a binder density on the substrate surface will cause inter-molecular nuclear dipole-dipole interactions to distort the REDOR distance measurements. To obtain accurate intra-molecular distances, the peptides should be kept sufficiently far apart so that only intra-molecular nuclear dipole-dipole interactions are significant. Inter-molecular nuclear dipole-dipole interactions are preferably kept less than about 10% of the intra-molecular interaction. In the case of $^{13}C-^{15}N$ measurements, this criterium can be monitored by observing $^{13}C-^{13}C$ dipolar couplings. As the dipole interaction falls off as $R^{-3}$, keeping adjacent binders apart by more than approximately 2–3 times the distance to be measured is sufficient. For measurements to 5 Å, this criterion can be satisfied by keeping binders approximately 10 Å or more apart. At a 10 Å spacing interfering $^{13}C$ or $^{15}N$ signals will not exceed 2.8 hz, which is sufficient attenuation for 30 hz or greater measurements.

In an embodiment wherein the binder is a peptide comprising the sequence $CX_6C$, that is synthesized on an mBHA resin that is also to serve as the NMR substrate, there is an additional upper bound on the peptide density. To prevent disulfide dimer formation in more than approximately 5% of peptides, the peptides are preferably kept apart by at least their average size. Dimer formation and incorrect disulfide scaffolds result in unconstrained, flexible peptides of altered structure distorting the REDOR distance determination of the properly conformationally constrained, cyclized binder peptides. A 10 Å or more separation will meet this requirement. In this case, more than 95% of the disulfide bonds will result in intended intra-molecular constraints. This separation may be adjusted based on a determination of actual dimer formation by chromatographic (e.g., HPLC) or mass spectroscopic analysis of the peptide after cleavage from the substrate (see Section 6.6, infra).

NMR instrumental sensitivity places a lower bound on binder density. By way of example, for an adequate observed signal to noise ratio using a preferred NMR spectrometer, no less than approximately $10^{18}$ observed nuclear spins should be present in a 0.1 g sample. This translates to having a binder density of no less than approximately 0.017 mmole/g (1 mmole=$10^{-3}$ mole). For alternative NMR spectrometers with higher field magnets ($^1H$ Larmor frequency of 500 mHz), the binder density may be as low as 0.0017 mmole/g.

A third substrate condition to be considered is pore size, which is relevant when measurement of binder bound to a target molecule is desired. In a preferred method of conducting such bound measurements, the substrate must have sufficient pore size so that the target molecules can diffuse to all binders on the surface of the substrate and bind to them. For example, folded, moderate sized protein targets of 50 kd are typically roughly spherical with diameters of approximately 50 Å. Preferable substrate pore sizes for use with such moderate sized protein targets are no less than 100–200 Å. Excessive pore sizes can result in a too dilute binder that decreases NMR signal intensity. The preferable pore sizes also facilitate high purity peptide synthesis directly onto substrate resins by similarly facilitating diffusion of reagents and solvents to synthesis sites. Also, binder substrate binding is preferably of such a nature that it will not be disrupted under either dry conditions, aqueous conditions, and conditions suitable to binder-target binding. Generally, adequate pore sizes are in the range of 100–500 Å, although this will vary with the size of the target molecule.

Solid phase substrates that can be used include but are not limited to mBHA resins, divinylbenzyl polystyrene resins, and glass beads. All of these substances can be manufactured to have binding sites in the range from 0 to 1.0 mmol/g. In addition, these substrates can be made so as to have the following surface areas: for mBHA about 100 $m^2/g$, for polystyrene from 50–100 $m^2/g$, and for glass from 0.1–100 $m^2/g$. These substrates also can be manufactured so as to have a surface binding site density in the range of from 0 to 1.0 $mmol/m^2$. More generally any microporous material with a surface density of binding sites adjustable from 0 to at least 1.0 $mmol/m^2$, and preferably with pore sizes in the preferred ranges, can be used. Suppliers of such adjustable resins include Chiron Mimotope Peptide Systems (San Diego, Calif.) and Nova Biochem (San Diego, Calif.).

Peptide binders can be synthesized directly on the surface of the substrates, by way of example as set forth in Section 6.6 infra, to achieve a purity of preferably at least 90%, more preferably at least 95%. In the case of a peptide comprising the sequence $CX_6C$, the preferred peptide spacing on the substrate is no closer than approximately 10 Å, or a peptide density of no greater than one peptide every 100 $Å^2$. Peptide synthesis on the preferred resin p-MethylBenzhydrilamine ["mBHA"] with 0.16 mmole/g of peptide binding sites, a surface of 100 $m^2/g$, and a preferable pore size of 100–200 Å results in a binder-substrate having such a preferable peptide surface density and suitable for accurate REDOR NMR measurements in dry, hydrated, and bound conditions. The total binder density is more than tenfold above instrumental sensitivity. The glycine linker provides a sufficient spacer from the substrate surface.

Steps 43, 44, and 45 in the preferred embodiment of the invention are carried out by one of a number of commercial peptide synthesis sources, such as Chiron Mimotope Peptide Systems (San Diego, Calif.) and Nova BioChem (San Diego, Calif.). Methods that can be used in these steps are known in the art. However, the preferred practice of these steps is detailed in the example in Section 6.6.

The invention thus provides a method of performing solid state NMR, preferably REDOR NMR, measurements of molecules on a solid phase substrate. In one embodiment, the molecule is a compound having conformational degrees of freedom at the temperature of interest that are limited to torsional rotations about bonds between otherwise rigid subunits, the torsional rotations respecting any conformational constraints. The molecule is preferably a peptide, more preferably a peptide of constrained conformation, and is most preferably a peptide having one or more cystines (e.g., comprising the sequence $CX_6C$). In other embodiments, the molecule is a peptide analog or derivative. In a preferred embodiment, the substrate is a solid phase on which the molecule (e.g., peptide) has been synthesized, with a high degree of purity. In specific embodiments, the REDOR measurements of the molecule on the substrate can be done in a dry nitrogen atmosphere, under hydrated conditions, and when the molecule is either free or bound to a target. The invention is also directed to a solid phase substrate having a surface to which is attached a population of molecules (preferably peptides, peptide derivatives, or peptide analogs), suitable for obtaining REDOR NMR measurements of the molecules. In specific embodiments, at least 90% of the population consists of a single molecule (i.e., 90% purity). In a more preferred aspect, 95% purity is present. Methods of producing such solid phase substrates, as described above, are also provided.

Step 46 REDOR spectroscopy is performed on the strategically labeled, binder peptide-resin sample. Step 46 details include final sample preparation, spectrometer parameters and tuning, and excitation pulse sequence. Sample preparation can be carried out by standard methods. The binder peptide-substrate sample is dried in $N_2$, and an approximately 0.1 g amount is sealed in the NMR measurement rotor. The rotor can be cooled, if necessary, to limit binder motion.

An alternative final sample preparation step is to bind the target molecule to the binder peptide-resin sample and then dry the complex in $N_2$. Optionally, the binder peptide can be split from the resin before binding to the target. In this alternative, the highly accurate REDOR NMR distances are of the bound binder and thus reflect any conformational changes that occur upon binding with the target.

A triple resonance, magic angle spinning ["MAS"] NMR machine is adaptable to REDOR measurements. Such machines are commercially available from Bruker (Billerica, Mass.), Chemmagnetics (Fort Collins, Colo.), and Varian (Palo Alto, Calif.). An exemplary machine suitable for use is in the laboratory of Prof. Zax, Cornell University (Ithaca, N.Y.). This machine includes a 7.05 Telsa magnet from Oxford Instruments (Oxford, United Kingdom) and RF pulse excitation and receiving hardware conventional in the NMR art. An exemplary measurement rotor is a triple resonance, MAS probe from Chemmagnetics.

The exemplary magnetic field is adjusted for a $^1H$ Larmor frequency of 300 Mhz with, corresponding Larmor frequencies for $^{13}C$ and $^{15}N$ of 75.4 and 30.4 Mhz, respectively. An exemplary probe spin frequency ($\omega_r$) is 4.8 kHz, with corresponding rotor period ($T_r$) of 0.208 msec. $^{15}N$ resonances are measured. The low natural abundance of $^{15}N$ eliminates the need for natural background corrections. Alternatively, $^{13}C$ measurements can be done with conventional background corrections.

REDOR is a pulse NMR technique requiring careful excitation of appropriate $^1H$, $^{13}C$, and $^{15}N$ resonances synchronous with the MAS rotor and followed by observation of the $^{15}N$ free induction decay. Many alternative REDOR excitation sequences have been described in the literature, some of which are found in the references cited hereinabove. These sequences can involve multiple $^{13}C$ excitations per rotor period. The simple pulse sequence preferred for use in this invention requires only one $^{13}C$ excitation per period.

Figure 4:
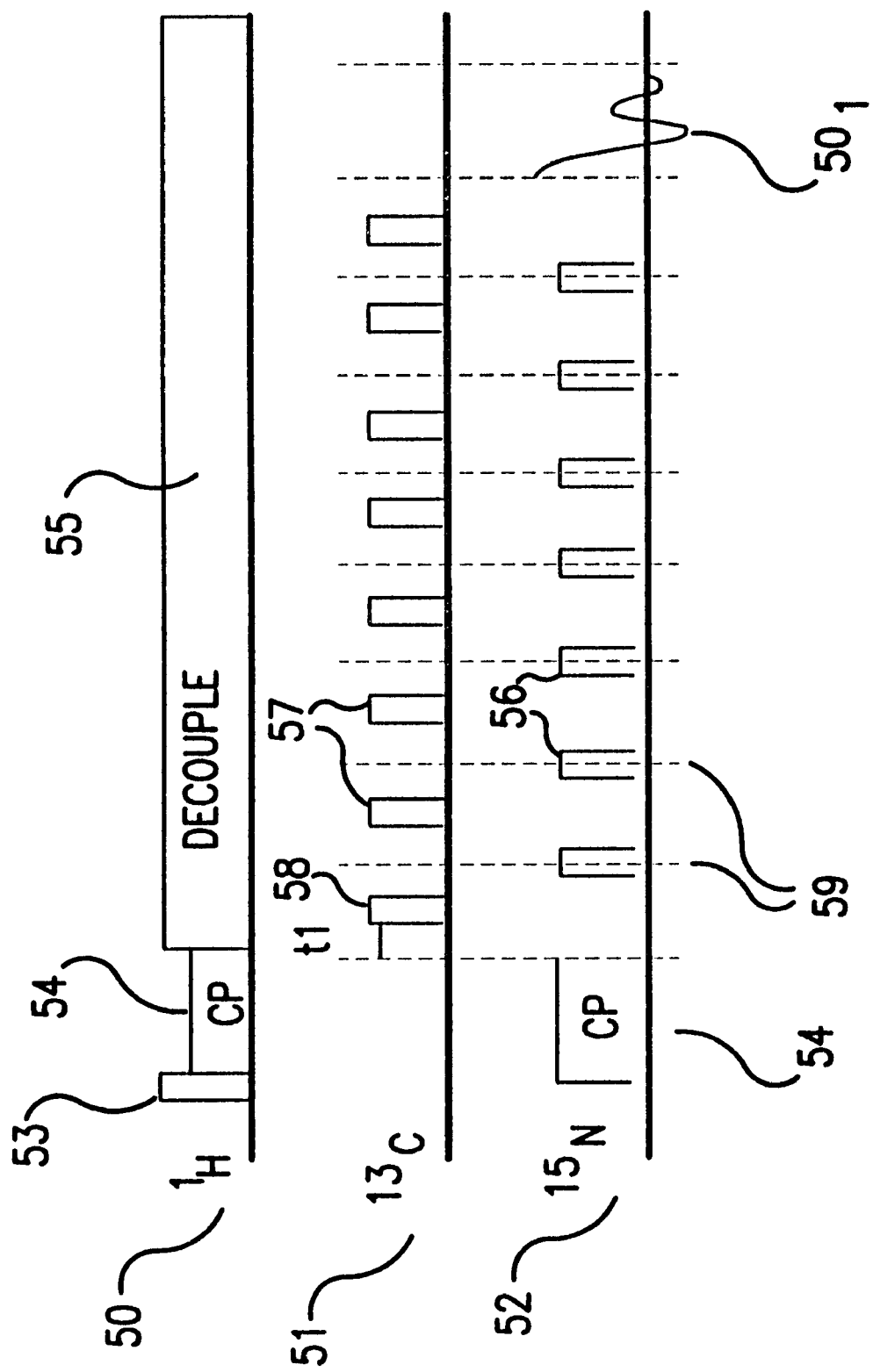
FIG. 4 is more detail for the step of FIG. 3 for performing NMR measurements.

The exemplary sequence for 8 rotor periods is illustrated in FIG. 4, and is detailed herein in a manner such that those skilled in the NMR arts can program an NMR spectrometer for similar measurement. Three channels excited are the $^1H$ channel 50, the $^{13}C$ channel 51, and $^{15}N$ channel 52. The $^{13}C$ and $^{15}N$ RF power supplies are tuned to the resonances of the nuclei whose distance is to be measured. The $^1H$ channel RF power is initially tuned to the resonance of a proton coupled to the $^{15}N$ of interest. The time sequence, (increasing to the right) of the exciting signals (increasing vertically) in each of these channels is illustrated.

In the $^{15}N$ channel, an initial excitation is applied to the $^{15}N$ spins in either of two manners: either an initial $\pi/2$ pulse may be applied or, as illustrated and preferred, a cross polarization transfer from the protons is made. Sufficient RF intensity is applied at time 54 in both the $^1H$ and $^{15}N$ channels, 50 and 51 respectively, to achieve a Hartman-Hahn precession match at a $\pi$ spin flip time of 13.2 $\mu$sec. Subsequent to the initial $^{15}N$ excitation, synchronous $\pi$ pulses 56 are applied in phase with the MAS probe rotor for $N_c$ rotor cycles, denoted by line 59, with sufficient RF intensity to achieve a $\pi$ spin flip time of 13.2 $\mu$sec. The phase of these $\pi$ pulses is varied systematically to reduce artifacts in a manner well known in the NMR arts. The preferred sequencing is detailed in Table 1.

TABLE 1

| $^{15}N$ $\pi$ Pulse Phase sequencing | |
|---|---|
| Number of rotor cycles between excitation and observation | Phase sequence (in processing frame) |
| 2 | YY |
| 4 | XYXY |
| 8 | XYXYYXYX |

The phase sequence is expressed as the axis, in the frame processing with the $^{15}N$ spins, about which the $\pi$ spin flip is made. This axis is systematically varied depending on the number of rotor periods intervening between the $^{15}N$ excitation and signal observation. The illustrated phase sequences may be varied into equivalent sequences in a conventional manner. For example, "XYXY" is equivalent to "—YX—YX". Finally, at 501 the free induction decay of the $^{15}N$ spins is observed and generates the time domain output signal.

In the $^1H$ channel, the preferred sequence is an initial exciting $\pi/2$ pulse 53 followed with the previously described cross polarization transfer 54 to the $^{15}N$ spins. The less preferred sequence omits these initial pulses in favor of a $\pi/2$ $^{15}N$ excitation. During the subsequent spin evolution time for $N_c$ rotor cycles and the free induction decay time 501, a decoupling field 55 is applied to the protons. The preferred decoupling field has a 66 kHz RF intensity to achieve a $^1H$ $\pi$ spin flip in 7.6 $\mu$sec.

In the $^{13}C$ channel, two distinct options must be measured. The first option (not illustrated) has no $^{13}C$ exciting pulses. The second option (illustrated) has synchronous $\pi$ pulses 57 applied for $N_c$ rotor cycles at the rotor frequency but with a fixed phase delay 58, denoted by $t_1$, and at sufficient signal intensity sufficient to achieve a $\pi$ spin flip time of 10.6 $\mu$sec. Any value of $t_1$ may be used; the preferred value is ½ the rotor period, $T_r/2$. Alternative REDOR pulse sequences include 2 or more $^{13}C$ pulses per rotor cycle.

Summarizing still with reference to FIG. 4, a REDOR measurement scan is characterized by the number of rotor cycles, $N_c$, of spin evolution. A complete scan comprises, first, an equilibration period, preceding the illustrated pulse sequences. Second, there is a $^{15}N$ excitation period comprising pulses 53 and 54. Third, there is a spin evolution period for $N_c$ rotor cycles which has two options, both measured. Both options comprise the application of decoupling $^1H$ field 55 and synchronous in phase $^{15}N$ $\pi$ pulses 56. The first option has no $^{13}C$ excitation; the second has synchronous phase displaced $^{13}C$ $\pi$ pulses 57. Fourth, and finally, there is observation of free induction decay 501 of the $^{15}N$ spins. FIG. 4 illustrates an $N_c$ of 8. Each scan option is repeated, and the induction decay signal accumulated, for a sufficient number of times to obtain acceptable signal to noise ratio. With the preferred practice, this has required less than approximately 5,000 scans, and typically 3000 have been sufficient.

An alternative implementation of the REDOR measurement interchanges the roles of $^{13}C$ and $^{15}N$ and measures the free induction decay of $^{13}C$. Further, the invention is not limited to this described pulse sequence and is adaptable to equivalent pulse sequences yielding direct inter-nuclear dipole-dipole interaction strengths.

Following REDOR measurement step 46, is data analysis step 47. This comprises several substeps. As is conventional, the free induction decay signal is Fourier transformed from the time domain to the frequency domain. The scan option without the $^{13}$C excitation produces a transformed signal with an observed $^{15}$N resonance peak of magnitude S; the scan option with $^{13}$C excitation produces an observed $^{15}$N resonance peak of magnitude $S_f$. The REDOR output signal, denoted $\Delta S/S$, is conventionally formed according to the equation:

$$\frac{\Delta S}{S} = \frac{(S - S_f)}{S} \quad (2)$$

The output signal is observed for different $N_c$. Preferably 0, 2, 4, and 8 rotor cycles are observed. Other preferred $N_c$ will be apparent during the following description.

Further analysis of the REDOR output signal, $\Delta S/S$, is made clearer by a very brief explanation of how this output signal represents the spin ½ dipole-dipole interaction between the $^{13}$C and $^{15}$N. In the spin evolution period, the $^{1}$H decoupling excitation eliminates all proton effects from the $^{13}$C and $^{15}$N NMR spectra. Magic angle spinning, in the scan option without any $^{13}$C excitation, eliminates all nuclear dipole-dipole and chemical shift anisotropy from the NMR line. Thus signal S represents an NMR resonance without any dipole interaction. However, in the second scan option, the $^{13}$C $\pi$ spin flip pulses reintroduce in a controlled manner the dipole-dipole interaction. This interaction causes additional dephasing, or loss of signal strength, in the observed $^{15}$N signal. Thus signal $S_f$ represents an NMR resonance with dipole interaction and the output signal $\Delta S/S$ represents the percentage strength of pure dipole-dipole interaction between the $^{13}$C and $^{15}$N nuclei. The exact loss of signal strength depends on the timing of the $^{13}$C pulses and the number of rotor cycles for which they are applied.

In the alternative where a general phase delay, $t_1$, is used, the expression for the REDOR signal is derived by numerically integrating the following equations from the Pan et al. reference (1990, J. Magnetic Resonance 90:330–340):

$$S_f = 1 - \frac{1}{2\pi} \int_0^{\frac{\pi}{2}} \int_0^{2\pi} \cos[T_r \omega'_D(\alpha, \beta, t_1)] \sin\beta \, d\beta \, d\alpha \quad (3)$$

where $$\omega_D(\alpha, \beta, t) = \quad (4)$$
$$\pm \frac{1}{2} D_{CN} \left[ \sin^2(\beta) \cos 2(\alpha + \omega_r t) - \sqrt{2} \sin 2\beta \cos(\alpha + \omega_r t) \right] \omega'_D(\alpha, \beta, t_1) =$$
$$\frac{1}{T_r} \left[ \int_0^{t_1} \omega_D(\alpha, \beta, t') dt' - \int_{t_1}^{T_r} \omega_D(\alpha, \beta, t') dt' \right]$$

This integration can be done by standard numerical integration techniques such as are found in Press et al., *Numerical recipes: the art of scientific computing,* Cambridge, U.K., Cambridge University Press, (1986), chapter 4, which is herein incorporated by reference. Alternatively the expression can be directly evaluated from the symbolic representations by numerical tools such as Mathematica from Wolfram Research Inc. (Champaign, Ill.) or Mathcad from Mathsoft Inc. (Cambridge, Mass.). In a preferred embodiment, however, a much simpler approach is used.

Figure 5:
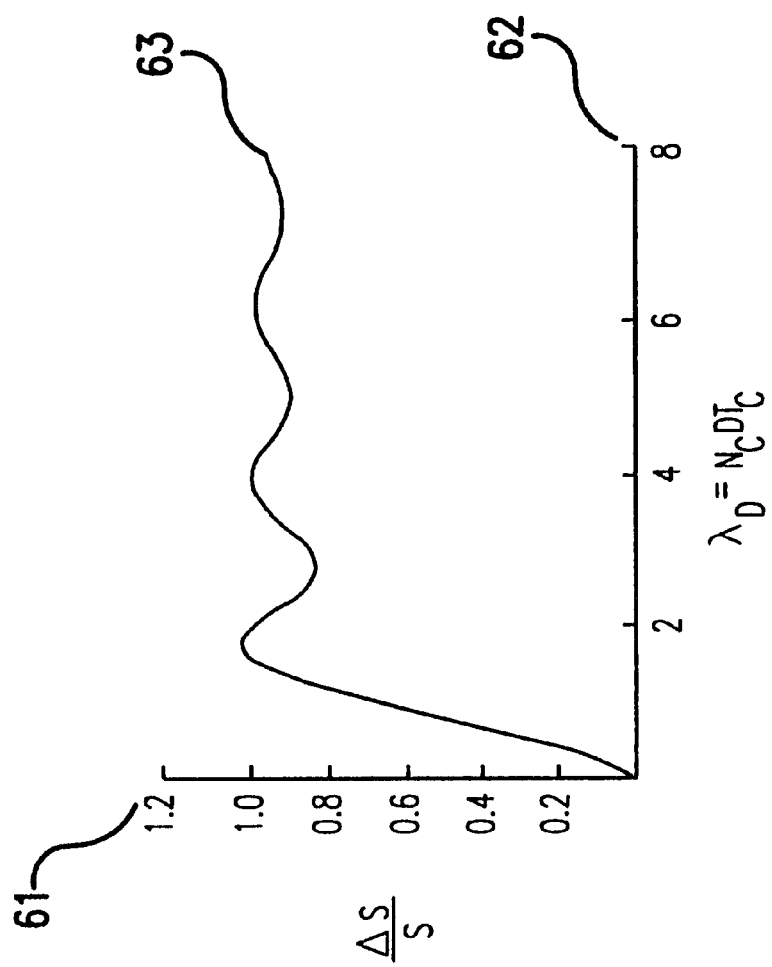
FIG. 5 is REDOR NMR signal response details for step of FIG. 3 of data analysis.

In the preferred embodiment, the $^{13}$C pulse phase delay is ½ the rotor period, $T_r$, and the preceding equations can be simply expressed (Mueller et al., 1995, J. Magnetic Resonance, in press):

$$\frac{\Delta S}{S} = 1 - [J_0(\sqrt{2})\lambda]^2 + 2 \sum_{k=1}^{\infty} \frac{1}{16k^2 - 1} [J_k(\sqrt{2}\lambda)]^2 \quad (5)$$

$$\lambda = N_c T_r D_{CN}$$

where $J_k$ is a Bessel function of the first kind. Adequate accuracy is obtained by limiting the summation of equation 5 to its first five terms. FIG. 5 is a graph of this equation. Vertical axis 61 represents $\Delta S/S$; horizontal axis 62 represents $\lambda$; and graph 63 represents equation 5.

In detail, step 47 of FIG. 3 uses equation 5 and the REDOR output signal, $\Delta S/S$, for various values of $N_c$ to obtain a best value for $D_{CN}$, the dipole interaction strength. The internuclear distance is simply and directly determined from $D_{CN}$ by equation 1. An exemplary method for finding the best value of $D_{CN}$ is to use a least squares method. First, form the sum of the squares of the differences of the observed $\Delta S/S$ and $\Delta S/S$ computed from equation 5, which will be a function of $D_{CN}$, $T_r$, and $N_c$ through $\lambda$. Second, find the value $D_{CN}$ minimizing this function by searching exhaustively in sufficiently small increments over the relevant range. For example, $D_{CN}$ can be varied by varying R in 0.01 Å increments from 0.5 to 8 Å. More efficient minimization methods as presented in Press et al. chapter 10 can also be used. Values of the Bessel functions can be simply calculated by the methods in Press et al, supra, §6.4. Alternatively, this minimization and best value determination is easily performed directly from the symbolic representations with the previously cited mathematical packages.

The example in Section 6.6 provides typical results of this measurement and analysis method.

This completes the method of FIG. 3 and determines the internuclear distance between the $^{13}$C and $^{15}$N nuclei to which the excitation channels were tuned for the REDOR NMR measurements. If other C-N pair distances are to be determined in the labeled binder, step 46 as detailed above is repeated for the other distinct resonances. If the alternative $^{15}$N resonances cannot be distinguished, separately labeled binders are prepared and measured.

5.7. CONSENSUS, CONFIGURATIONAL BIAS MONTE CARLO

Broad overview

With reference to FIG. 1, having found N specifically binding members of one or more libraries, step 2, selected a candidate pharmacophore shared by all these binders, step 3, and determined a few strategic distances in the vicinity of the candidate pharmacophore, step 4, precise pharmacophore and binder peptide structures are now determined by the preferred method, the consensus, configurational bias Monte Carlo method. Other orderings and identities of these steps are possible. For example, the binders may be predetermined thereby rendering step 2 unnecessary. Further, no strategic distance measurements may need to be made, and step 4 may be omitted. Alternatively, a partial structure determination step may be inserted before step 4 to guide selection of distances for measurement.

Pharmacophore structure determination of this invention is not limited to the CCBMC method to be described. CCMBC makes the most efficient use of heuristic consensus binding and partial distance measurement information. However, the consensus pharmacophore can be determined by methods including but not limited to use of exhaustive REDOR NMR measurements or by extensive but fewer REDOR measurements in conjunction with a conventional molecular structure determination method, such as molecular dynamics, conventional Monte Carlo, or even peptide folding rules.

In the following description, the CCBMC method is broadly overviewed; subsequently, details of important steps are described; and finally a description of the preferred computer method and apparatus for practicing the invention is given. From the description of the methods, equations, data structures, and programs provided herein, one will be able readily to translate them into implementations.

Although the following descriptions are directed to binders isolated from the preferred library of peptides comprising the sequence $CX_6C$ (constrained by disulfide bonds), the method is applicable to more general organic diversity library members. It is immediately applicable to compounds from constrained peptide libraries with other scaffolds and also to compounds from similar peptoid libraries. It will be readily apparent that the method is applicable to any compounds whose structural region of interest exhibits conformational degrees of freedom at a temperature of interest (e.g., body temperature—37° C.) that are limited to torsional rotations of rigid molecular subunits about bonds between the subunits, in which any loops present in the structural region of interest are independently rotatable by concerted rotation (see Section 7. Appendix: Concerted Rotation). Examples of such compounds include but are not limited to peptides, peptoids, peptide derivatives, peptide analogs, etc., including members of libraries discussed in Section 5.2, supra.

General features of Monte Carlo simulation methods are known. A reference is Rowley, *Statistical mechanics for thermophysical Property calculations*, Englewood Cliffs, N.J., PTR Prentice Hall (1994), especially chapters 5 and 7, which is herein incorporated by reference. The application of simple Monte Carlo to constrained peptides has conventionally been hindered by difficulty generating geometrically proper and energetically useful conformational alterations, and by the consequent wasteful and inefficient exploration of conformational space. This method overcomes these problems for constrained peptides with a novel combination of techniques. In addition, this method is uniquely able to incorporate partial information about binding affinities and distance measurements to improve determination of the pharmacophore structure, one goal of the invention.

Figure 8:
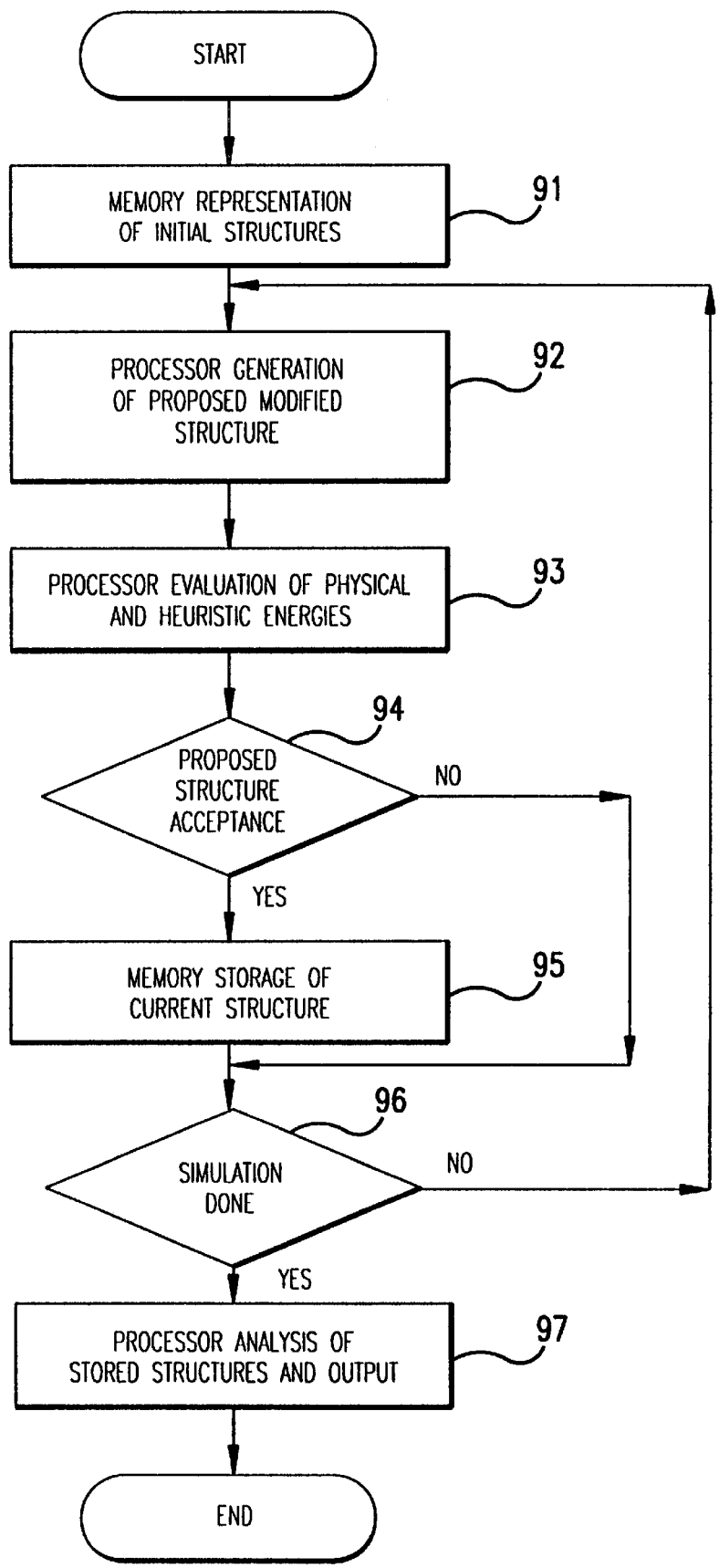
FIG. 8 is more detail for the Step of FIG. 1 for configurational bias Monte Carlo structure determination.

FIG. 8 is a overview of the method. Step 91 represents the initial geometric and chemical structure of each binding peptide in computer memory. Peptide geometric structure is represented as a set of records, each record representing one rigid subunit or one atom of the peptide. The subunit records are linked together as the subunits are linked in the peptide molecule. Each rigid unit record includes fields for the composition, structure, and connectivity of the rigid unit represented. Since the rigid units only undergo torsional rotations about mutual bonds, their internal geometric structure is fixed.

If a previous run with these peptides has been done, peptide initial structure may be chosen as one of the structures generated late in that run. Such an initial structure is desirable since the effects of arbitrary initial conditions have been eliminated. Alternatively, an initial structure is generated from a prototypical backbone without side chains by adding sidechains with random torsional orientations. For members of each type of diversity library, a prototypical backbone meeting structural constraints and representing an allowed configuration for a member possessing no side chains can be defined. The prototypical backbone for the $CX_6C$ library is generated from the CCBMC model itself as run for the linear peptide $C(gly)_6C$ (SEQ ID NO:7) using a Hamiltonian consisting only on the $H_{NMR}$ term. The $H_{NMR}$ term contains only terms which, in the disulfide bond backbone region $—C_1—S_1—S_2—C_2—$, limit the $S_1-S_2$ distance to 2.038 Å and both the $C_1—S_2$ and the $S_1—C_2$ distances to 2.883 Å. When run for a linear peptide, no Type II backbone moves are made. Only Type I backbone moves which remove and regrow randomly selected portions of the backbone are used to generate backbone alterations. The model is run with temperatures gradually decreasing from room temperature to a small temperature, approximately 1° K. The final low temperature structure is used for the prototyptical backbone. Backbones for similar constrained peptide libraries can be constructed in similar manners.

In memory, for each peptide, a current structure is represented; the initial current structures being the just assigned initial structures. Also in memory is represented a proposed modified structure for one peptide. At step 92 the processor generates "moves" that transform the current structure of a randomly chosen peptide into a proposed modified structure. The moves mimic body temperature (37° C.) thermal agitation experienced by the binders so that their equilibrium structure may be determined.

Generation of these moves for conformationally constrained peptides is an important aspect of this method. There are two move types. Type I moves alter the conformation of the side chain of a randomly chosen amino acid of the randomly chosen peptide. The alteration is built by side chain removal followed by side chain regrowth into a new torsional conformation. During regrowth, unfavorable overlap with neighboring side chains is avoided. Type II moves alter the conformation of a limited random region of the peptide backbone of a randomly chosen binder by performing linked, or "concerted", rotations, the linking being such that only four backbone rigid units are spatially displaced. Thereby the internally bonded ring of 8 amino acids will not be disrupted. A reference describing a similar move in linear alkane molecules is Dodd et al., A concerted rotation algorithm for atomistic Monte Carlo simulation of polymer melts and glasses, Molecular Phys., vol 78, pp 961 et seq. (1991), which is herein incorporated by reference. The ratio between the Types I and II moves is an adjustable parameter with a preferred value of 4.

Another important aspect of this method is that both moves are selected in a "configurationally biased" manner. Normal Monte Carlo methods use standard Metropolis procedures, in which each proposed structure is generated randomly and independently of the current structure with an equal a priori probability. However, for complex molecules, it is known that this typically results in the generation of many highly improbable or energetically unlikely structures. In some situations up to $10^5$ wasted moves are generated for each useful move, a very considerable waste of processor resources. In contrast, the method of this invention generates proposed structures according to an a priori probability depending on the current structure and the energetic cost of the new structure. This bias toward more acceptable structures of lower energy avoids generating highly improbable structures, making a very much more efficient use of processor resources. Because detailed balance must be satisfied, the acceptance probability of the configurationally biased method must include factors in addition to the usual Boltzman factor. A reference applying a similar method for simple linear alkanes is Smit et al., Computer simulations of the energetics and siting of n-alkanes in zeolites, J. Phys. Chem. vol 98, pp 8442 et seq. (1994), which is herein incorporated by reference.

At Step 93 the processor evaluates the energy, or Hamiltonian, of the proposed configuration. The Hamiltonian contains two groups of terms: conventional physical energy terms, and heuristic constraint terms. Conventional terms include the energies of rigid unit torsional rotations and of Lenard-Jones, electrostatic interactions, and H-bonding between atoms in different rigid units. Bond lengths and angles are assumed fixed at the temperature of interest and their energies constant. These conventional interactions are exclusively intramolecular; no physical intermolecular interaction effects are considered in this invention.

References for the conventional energies are Weiner et al., An all atom force field for simulations of proteins and nucleic acids, J. of Computational Chem., 7:230–52 (1986); and Weiner et al., A new force field for molecular simulation of nucleic acids and Proteins, J. Amer. Chem. Soc. 106:765 (1984) (herein referred to as the "AMBER references"), which are herein incorporated by reference.

Another important aspect of the Monte Carlo method of this invention is the heuristic terms: the consensus term and the measurement constraint term. They uniquely make use of partial information on the binder peptides to guide the Monte Carlo simulation. The consensus term, $H_{consensus}$, is added to the Hamiltonian to represent that all the binders do in fact bind to the same protein target in the same physical and chemical manner. Since binding occurs at the shared candidate pharmacophore in each binder, this term makes energetically unfavorable moves that cause the geometric structure in the shared pharmacophore to depart from an average, common structure. Pseudo chemical "bonds" to this average structure are added which mimic the actual physical bonding to the surface groups of the protein target. If the candidate pharmacophore is in fact the actual pharmacophore, this energy will become minimized and small in the equilibrium configuration, since there will be an actual, shared, geometric configuration. If the candidate pharmacophore is not the actual one, this term will not become minimized or small, as there is no physical reason for this region of the peptide molecules to share a common structure. This is the only Hamiltonian term which couples the N binders together; no physical intermolecular effects are considered. The binders are otherwise treated independently by the method.

The measurement constraint term, $H_{NMR}$, is added to represent the distance measurements made, which are in fact actual distances in the molecules and constrain any simulated structure. This term makes energetically unfavorable, by adding pseudo chemical bonds of the measured lengths, moves that cause the constrained internuclear distance to depart from their measured values. Of course if no partial distance measurements have been made or are otherwise available, this term may simply be omitted from the Hamiltonian without adversely affecting the practice of this step. Which measurements to make, if any, is guided by the results of the consensus structure determined. If an adequate structure can be obtained without assistance of distance measurements, none need be incorporated. If inadequate results are obtained, additional iterations of the method will need distance measurement inputs.

Step 94 tests the proposed structure against an acceptance probability, accept(curr→prop). This acceptance probability is determined by the energy of the proposed structure previously computed in step 93. If the proposed structure fails this test and is not accepted, the method progresses immediately to step 96. If the proposed structure meets the test and is accepted, the accepted proposed structure replaces and becomes the current structure. The proposed structure of this peptide is also saved (given certain other conditions detailed later) in a separate memory store of structures for later analysis. This structure store is preferably on disk.

Repeated application of the concerted rotation may lead to a slightly imperfect structure, due to numerical precision errors. In an alternative embodiment, peptide geometry would be restored to an ideal state by application of the Random Tweek algorithm after several thousand moves (Shenkin et al., 1987, Biopolymers 26:2053–85).

Step 96 tests whether enough structures of equilibrated total energy have been generated in this simulation run. The run terminates if a sufficient number have been generated. Sufficiency is determined on the basis of whether the statistical sampling errors of the average pharmacophore structure determined at step 97 is adequate (typically, less than 0.25 Å). Preferably, 25,000 equilibrated structures would be accumulated for each run. Also, preferably, three runs would be performed for a total of 75,000 saved structures.

Figure 9:
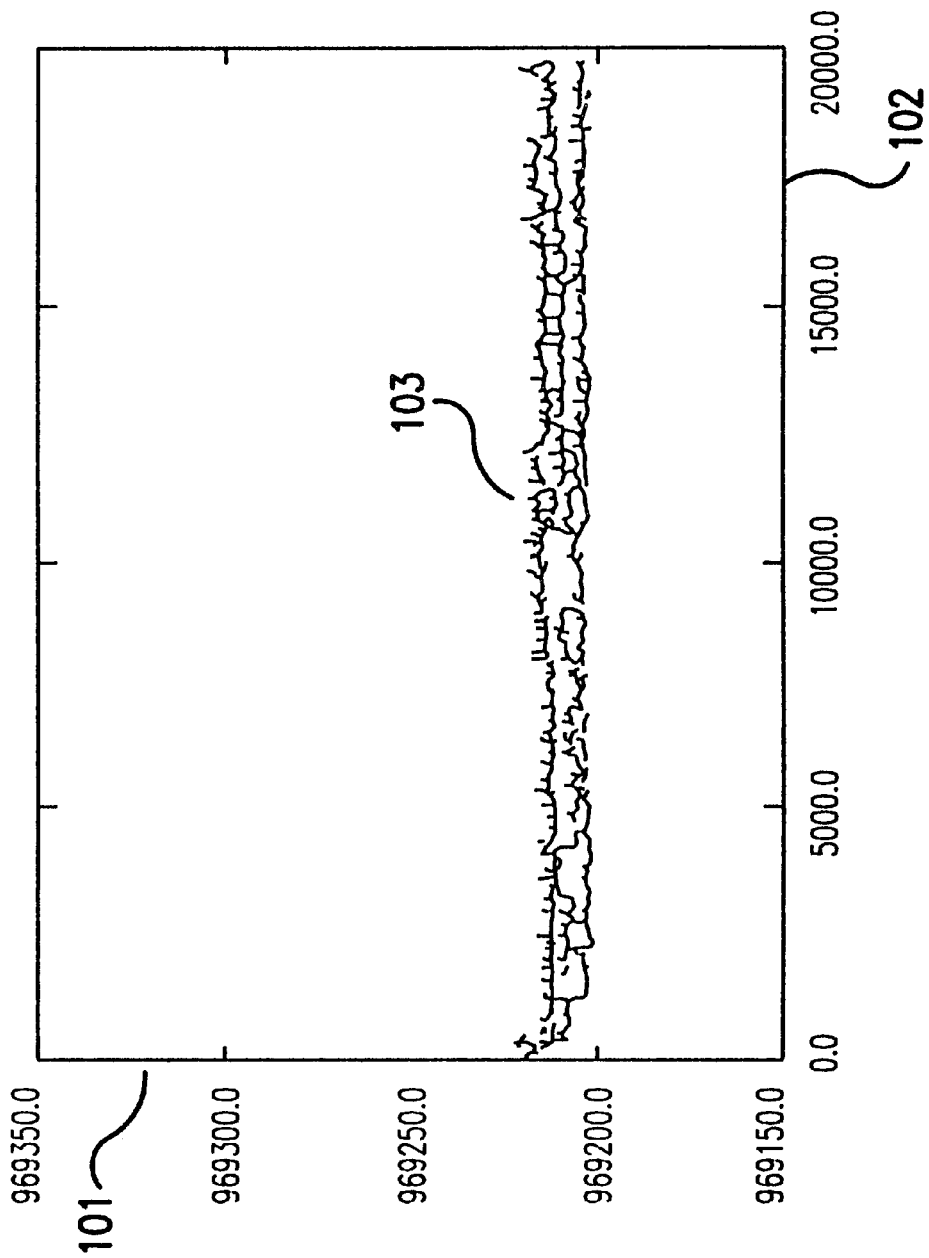
FIG. 9 is a sample of simulation completion data.

FIG. 9 illustrates energy equilibration of an actual run. Axis 101 is the total energy of a set of peptide binders; axis 102 is the number of moves accepted. Traces 103 represent total energies of all binders from each of the three runs. Typically, run energy rapidly equilibrates within less than approximately 2000 moves in most cases. Subsequent saved structures are counted toward termination. Traces 103 display typical energy variations superimposed on a secular stability. The illustrated energy variations typically comprise several components having different variabilities. First, there is a very high frequency oscillation with a period of a few tens of moves (known as "hair"). Second, there is a low frequency oscillation with a period of several hundred to a few thousand moves and with low amplitude.

Step 97 analyzes the structure stored in memory. In the simplest preferred embodiment, the stored geometric structures for each binder are simply averaged, yielding a final structure for each binder and for the candidate pharmacophore. In another alternative, clustering software seeks clusters of similar structures for each binder. The clusters are then averaged to give a final structure for each variant structure for each binder. The variants represent alternative foldings for the binder. Exemplary clustering methods are found in Gordon et al. Fuzzy cluster analysis of molecular dynamics trajectories, Proteins: Structure, Function and Genetics 14:249–264 (1992).

Alternative post-processing can be-done on the clustered structures to account for small bond angle vibrations. Such vibrations are expected to make small perturbations to the clustered structures determined by the Monte Carlo method and can be accounted for by a brief molecular dynamics simulation. Such a simulation is fully defined by the Hamiltonian, comprising the physical and heuristic energies to be described infra in Eqn. 8, and by the temperature of interest. The structures observed during the simulation are averaged to determine a final more accurate equilibrium structure. A code capable of performing such a simulation is Discover® from BIOSYM (San Diego, Calif.). Preferably, the molecular dynamics simulation would be run for approximately $10^5$ bond angle vibration periods. Since the typical bond angle vibration period is $10^{-2}$ ps (1 ps=$10^{-12}$ sec.), such a run will encompass approximately 1 ns of molecular time.

Configurational Bias Move Generation Details

One Type I or II move will, in general, alter the position of several rigid units on a side chain or along the backbone. Each altered rigid unit is sequentially considered during move generation. The Hamiltonian describing the energy of the rigid unit currently being considered in a move is divided into an internal, $u^{int}$, and an external, $u^{ext}$, part, where $u^{ext}$ is all energy not included in $u^{int}$. In the preferred embodiment, $u^{int}$ is set to 0; an alternative choice would be to include only the torsional interaction energy between this rigid unit and units to which it is currently bound. $u^{int}$ generates a probability distribution, $p^{int}$, according to which is generated a set, $\phi_k$, k=1 ... K, of candidate torsional angles for the bond between the rigid unit being examined and rigid units already examined. $u^{ext}$ generates another probability distribution, $p^{ext}$, according to which is selected one torsional angle from the prior set as the proposed new angle for the rigid unit being examined. These probabilities are defined by the equations:

$$p_i^{int}(\phi_{i,k}) \propto \exp[-\beta u_i^{int}(\phi_{i,k})] \quad (6)$$

$$p_i^{ext}(\phi_{i,k}) = \frac{\exp[-\beta u_i^{ext}(\phi_{i,k})]}{w_i^{ext}}$$

$$w_i^{ext} = \sum_{k=1}^{K} p_i^{ext}(\phi_{i,k})$$

In this equation, "$_i$" signifies the rigid unit being considered, K is the total number of candidate torsional angles generated by $p^{int}$, and $\beta=1/kT$ (k is Boltzman's constant; T the temperature, preferably 37° C.). The overall probability of generating a transition from the current to the proposed structures and accepting the proposed structure are given by the equations:

$$P(curr \to prop) \propto \prod_{i=1}^{M} p_i^{int}(\phi_{i,k}) p_i^{ext}(\phi_{i,k}) \quad (7)$$

$$W^{new} = \sum_{i=1}^{M} w_i^{ext}$$

$$accept(curr \to prop) = \min\left(1, \frac{W^{new}}{W^{old}}\right)$$

In this equation, M is the total number of rigid units added in the move. $W^{old}$ is a weight for the reverse move and will be described subsequently.

Because energy is included in the generation probabilities, proposed structures are preferentially of lower energy. Since the acceptance of proposed structures depends on their energies, the acceptance of proposed structures is thereby more probable.

Peptide Memory Representation Details

It is well known that at body temperature peptides consist of linked rigid units capable only of torsional rotational about mutual bonds whose lengths and angles are fixed. The torsional rotations respect any molecular conformational constraints. See Cantor et al., *Biophysical chemistry part I the conformation of biological macromolecules,* New York, W. H. Freeman and Co. (1980), which is herein incorporated by reference. Table 2 lists the rigid units encountered in the preferred embodiment of this invention utilizing libraries of conformationally constrained peptides. Table 2, where applicable, also lists dihedral bond angles between incoming and outgoing bonds to a rigid unit and the assigned unit type.

TABLE 2

| Type | Chemical Structure | Bond angle (if applicable) |
|---|---|---|
| Backbone and side chain rigid units | | |
| A | $-NH_2$ | |
| B | $-C\alpha H-$ | 70.5° |
| C | $-CONH-$ | 70.5° |
| D | $-COOH$ | |
| Side chain only rigid units | | |
| E | $-CH_2-$ | 70.5° |
| F | $-CH_2-$ | 70.5° |
| G | $-S-$ | 70.5° |
| H | $-C_6H_4-$ | 0° |
| I | $-CH_3$ | |
| J | $-OH$ | |
| K | $-SH$ | |

Table 3 illustrates the decomposition of all amino acid side chains into rigid units. Glycine is a special case, without a side chain. Proline is a special case with a side chain cyclically bonded to the backbone amino N.

TABLE 3

| Amino Acid | Rigid Units |
|---|---|
| Glycine | $-C\alpha H_2-$ (SPECIAL CASE) |
| Alanine | $-CH_3-$ |
| Arginine | $-CH_2-CH_2-CH_2-CN_3H_4$ |
| Aspartate | $-CH_2-COOH-$ |
| Asparagine | $-CH_2-CONH_2$ |
| Cysteine | $-CH_2-SH$ |
| Glutamate | $-CH_2-CH_2-COOH$ |
| Histidine | $-CH_2-C_3N_2H_3$ |
| Isoleucine | $-CH(-CH_3)-CH_2-CH_3$ |
| Leucine | $-CH_2-CH(-CH_3)_2$ |
| Lysine | $-CH_2-CH_2-CH_2-CH_2-NH_2$ |
| Methionine | $-CH_2-CH_2-S-CH_3$ |
| Phenylalanine | $-CH_2-C_6H_5$ |
| Serine | $-CH_2-OH$ |
| Threonine | $-CH(-CH_3)-OH$ |
| Tryptophan | $-CH_2-C_8NH_6$ |
| Valine | $-CH(-CH_3)-CH_3$ |
| Tyrosine | $-CH_2-C_6-H_4-OH$ |

FIG. 10 illustrates a structurally correct but geometrically inaccurate decomposition of the peptide backbone $CX_6C$ into rigid units (inessential hydrogens have been omitted). Rigid units are set off in boxes 121 and their types 122 are indicated. FIG. 11 illustrates a structurally correct but geometrically inaccurate decomposition of the peptide backbone and side chains of -arginine-glycine-aspartate- ("RGD") into rigid units. Rigid units are set off in boxes 131 and their types 132 are indicated.

Rigid units are represented as records in memory. The data structure for a peptide comprises records for its constituent rigid units linked together by data pointers exactly as the actual rigid units in the peptide are chemically linked. The record representing a rigid unit comprises fields for: type of the unit, pointers to chemically bonded units, all atoms of the unit and their spatial positions, atoms of the unit that are the target of the incoming and outgoing bonds, amino acid to which the unit belongs, and atomic composition of the unit.

A known, conventional representation of atoms and atomic interactions is taught by the AMBER references. Each atom is divided into a series of subtypes of specific properties. For example, for carbon there are subtypes C, C2, CA, CT, etc.; for nitrogen, there are N, N2, etc.; for oxygen, there are O, O2, etc.; and for hydrogen, there are H, H2, etc. Bonds between each pair of subtypes are separately characterized by equilibrium lengths, angles, and torsional energies. Interactions between each pair of subtype atoms are separately characterized by Lenard-Jones force parameters, hydrogen bonding force parameters, and electrostatic charges. Amino acid charge distributions are in Weiner et al., J. of Computational Chem., 7:230–52 (1986).

Thus each atom in each rigid unit is represented by an in-memory record comprising fields for: its AMBER reference subtype and any electrostatic charge. The atom's spatial position relative to its containing rigid unit, stored in that unit's record, is geometrically determined from the unit's internal chemical structure and bonds by the AMBER bond lengths and angles defined for each of these bonds. The relative spatial positions of atoms within a rigid unit are, of course, fixed, and there is no interaction energy to consider between atoms within a rigid unit.

FIG. 11 is a complete memory representation of a tripeptide sequence -RGD- (a known pharmacophore). Rigid units are set off in boxes 131 and their types 132 are indicated. The torsional degrees of freedom between the rigid units are indicated by angle arrows 133. AMBER atoms types are indicated as at 134. Net atomic charges are indicated only for arginine as at 135. Rigid unit records are linked into a data structure modeling the rigid unit's physical linkages. Not shown are relative atomic spatial positions represented by the atoms rectangular coordinates.

All parameters defining the AMBER atomic representations and interatomic forces can be found in Weiner et al., J. of Computational Chem., 7:230–52 (1986), and Weiner et al., J. Amer. Chem. Soc., 106:765 (1984). Conventionally, these parameters are obtained from computer readable files from commercial sources. The preferred computer readable source of these parameters is from Insight II® 2.3.5 software from BIOSYM (San Diego, Calif.). Other sources are Tripos (St. Louis, Mo.) and CHARMm (Molecular Simulations, Inc., Burlington, Mass.).

Interaction Energy Evaluation Details

The form of the intramolecular energy, or Hamiltonian, evaluated at step 93, is an important element of this invention. The Hamiltonian consists of the components:

$$H_{total} = \sum_{l \in binders} H_{l,total} \tag{8}$$

$$H_{l,total} = H_{l,molecular} + H_{l,NMR} + H_{l,consensus}$$

The $H_{l,molecular}$ component is determined from the Weiner et al. references, J. of Computational Chem., 7:230–52 (1986), and J. Amer. Chem. Soc., 106:765 (1984).

$$H_{l,molecular} = \sum_{\substack{n,i \in \\ rigid\ unit \\ torsional \\ angles}} \frac{V_{in}}{2}(\cos(n\varphi_{l,i}) - \gamma_i) + 1) + \tag{9}$$

$$\sum_{\substack{i<j \\ i,j \in \\ atom\ pairs}} \left[\frac{A_{ij}}{R_{l,ij}^{12}} - \frac{B_{ij}}{R_{l,ij}^{6}}\right] \sum_{\substack{i<j \\ i,j \in \\ atom\ pairs}} \left[\frac{q_i q_j}{\in R_{l,ij}}\right] +$$

$$\sum_{\substack{i<j \\ i,j \in \\ H\text{-}bond\ pairs}} \left[\frac{C_{ij}}{R_{l,ij}^{12}} - \frac{D_{ij}}{R_{l,ij}^{10}}\right]$$

Here, $\varphi_{l,i}$ is the i'th torsional angle between rigid units of the l'th binder peptide, and $R_{l,ij}$ is the interatomic distance between the i'th and j'th atoms in different rigid units of the l'th binder. The first term in this equation is the torsional energy of rigid units; the second is the interatomic Lenard-Jones energy; the third is the interatomic electrostatic energy; and the fourth is the interatomic hydrogen bond energy. Rigid unit torsional rotations directly change the first term. Such rotations indirectly change all other terms as interatomic distances change.

The AMBER parameters $V_{in}$, $A_{ij}$, $B_{ij}$, $q_i$, $C_{ij}$ and $D_{ij}$ are obtained as stated above. The effect of water is approximated in a known manner by setting $\epsilon$ equal to $4\epsilon_0 r$, where r is distance (in Å) in the electrostatic term and $\epsilon_0$ is the vacuum permeability.

The distance constraint term, as described, makes energetically unfavorable moves which cause those measured interatomic separations in the simulation to depart from their measured values. If no measured values are available, this term is simply omitted from the Hamiltonian. Since this is not a physical energy and in simulation equilibrium the binders should have the measured distance, it is advantageous that this term should make only a small contribution to the equilibrium energy, no more than 10% of the total energy and preferably approximately 2.5 to 5%. Further, it is advantageous that the energetic disfavor be weighted by the confidence in the measurements, so that measurements having more confidence have a greater effect.

Many forms of this energy meet these criteria. The preferred form is:

$$H_{l,NMR} = \sum_{\substack{i<j \\ observed \\ distance\ pairs}} \frac{(R_{l,ij} - R_{l,ij}^{(o)})^2}{2w_{l,ij}} \tag{10}$$

where $R^{(o)}_{l,ij}$ is a measured distance in the l'th binder peptide between atomic pair ij. This makes the constraints appear as an elastic pseudo-bond with equilibrium length as measured. The $w_{l,ij}$ are weights designed to meet the above size criteria. In the preferred embodiment, they are calculated with an overall multiplicative factor limiting the contribution of $H_{l,NMR}$ to no more than approximately 5% of the total equilibrated energy. Their relative value is selected to reflect the lower reliability of longer measurements. Thus if $R^{(o)}_{l,ij}$ is between 0 and 3 Å, $w_{l,ij}$ has a relative value of 1; if the measurement is between 3 and 4.5 Å, the relative value is 2; if between 4.5 and 7 Å, the value is 3; and if the distance exceeds 7 Å, the term is dropped from the sum. Other alternative weight assignments meeting the general criteria are clearly possible.

The consensus constraint term, as described, makes energetically unfavorable moves which cause the candidate pharmacophore in each of the binders to depart from an average, shared configuration. In simulation equilibrium when the candidate is the actual pharmacophore, the binders share the pharmacophore structure and this term should be small. Since this is not a physical energy, in the case where the candidate pharmacophore is correct, this term should not be large compared to the total energy, in equilibrium no more than 10% of the total energy, and preferably approximately 5%. Further, the energetic disfavor should preferably be weighted by the affinity of each binder for the protein target, so that binders with greater affinity have a greater energetic effect.

Many forms of this energy meet these criteria. The preferred form is:

$$R_{ij}^{(c)} = \sum_{l \in binders} \frac{R_{l,ij}}{N} \qquad (11)$$

$$H_{l,consensus} = \sum_{\substack{i<j \\ i,j \in \\ pharmacophore \\ distance\ pairs}} \frac{(R_{l,ij} - R_{ij}^{(c)})^2}{2w'_{l,ij}}.$$

$R^{(c)}_{ij}$, the shared consensus structure for the candidate pharmacophore, is an average of the interatomic distances between corresponding atomic positions, ij, in the shared pharmacophore in all binders. This makes the constraints appear as a pseudo-bonds to a shared pharmacophore, which represents the binding to the protein target. The $w'_{l,ij}$ are weights designed to meet the above size criteria. In the preferred embodiment, they are calculated with an overall multiplicative factor limiting the contribution of $H_{l,consensus}$ to no more than approximately 5% of the total equilibrated energy. Their relative value is selected to reflect that binders with lower affinity are less reliable indicators of actual pharmacophore structure. Thus the relative value of the weights is proportional to the logarithm of the affinity of the corresponding binder with an affinity of 1 µmolar having a relative weight of 1. Other weight assignments meeting the general criteria are clearly possible. The heuristic $H_{consensus}$ is the only Hamiltonian term linking together the various binders.

All Hamiltonian components change only due to the dependence of the interatomic distances, $R_{l,ij}$, on the rigid unit's torsional rotation. The $R_{l,ij}$ are the well known Euclidean distances between the atomic coordinates stored in the rigid unit records. Calculation of coordinate changes due to rotation of angle φ about a bond with unit direction n originating at atom A with position x is well known, but will be detailed. (Throughout, symbols representing vector quantities are indicated by underlining.) First, translate from the current coordinate origin to an origin at position x by adding x to all relevant coordinate vectors. Second, apply a rotation matrix, T, to the atomic coordinate vectors. Third, translate back to the prior coordinate origin from x by subtracting x from all relevant coordinate vectors. A rotation matrix is given by:

$$T = \cos(\varphi)I + nn^T[1 - \cos(\varphi)] + M\sin(\varphi) \qquad (12)$$

$$M = \begin{bmatrix} 0 & -n_z & n_y \\ n_z & 0 & -n_x \\ -n_y & n_x & 0 \end{bmatrix}$$

A reference for this computation is Goldstein, *Classical mechanics,* Massachusetts, Addison-Wesley (1981), especially chapter 4, which is herein incorporated by reference.

Type I Move Generation

Type I moves alter side chain structure of a randomly chosen amino acid in a randomly chosen binder. These random choices are conventionally made by a random number subroutine. The chosen side chain is "removed" from the binder peptide and "grown" back rigid unit by rigid unit. For the next, i'th, rigid unit to be added, K possible new torsional angles are generated according to $p^{int}$. Preferably K is from 10 to 100. One of these torsional angles is selected according to $p^{ext}$, and the rigid unit is added at this new angle. Determination of $p^{ext}$ requires obtaining the normalization $w_i^{ext}$. At each step the $u^{int}$ and $u^{ext}$ used to calculate the respective probabilities include only interaction energies with rigid units present in other amino acids or already grown back. Rigid units not yet added are ignored. After all the side chain rigid units have been added back, $W^{new}$ is computed as the product of the normalization factors.

Figure 12:
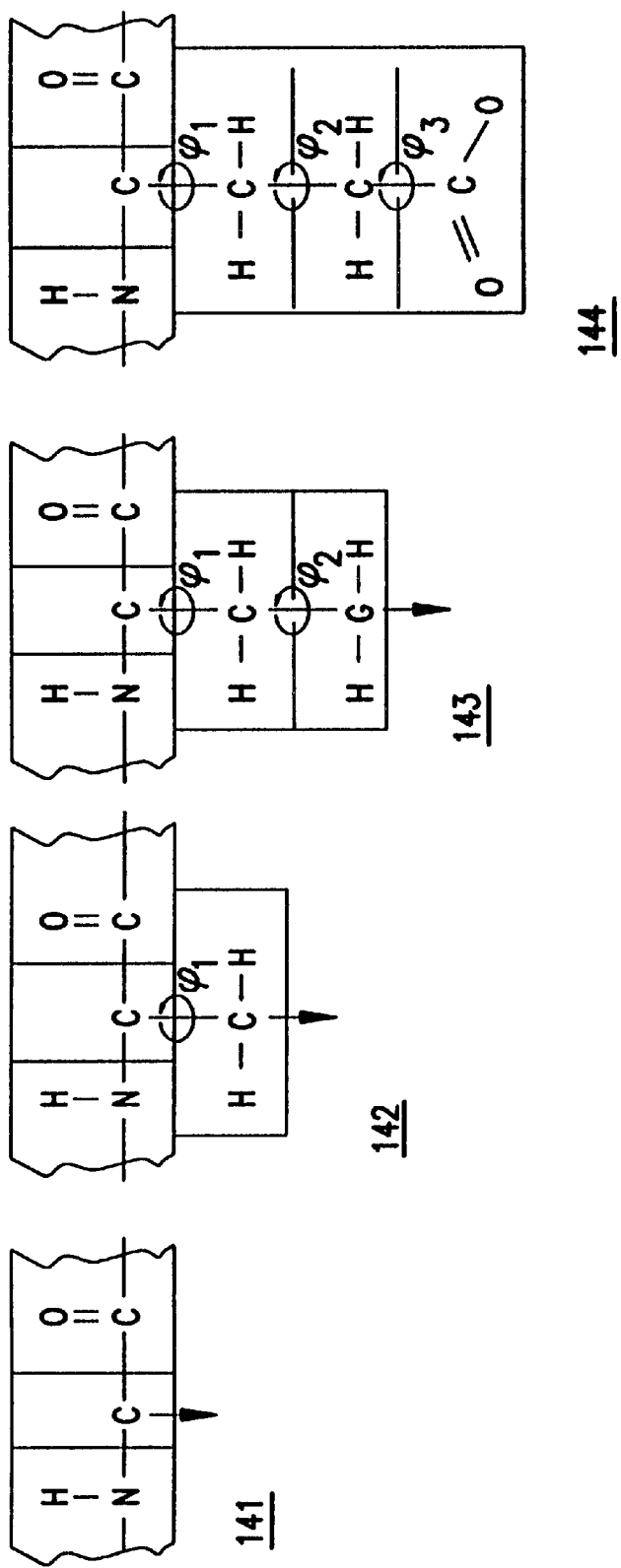
FIG. 12 is more detail for the step of FIG. 8 of processor generation of proposed modified structures by Type I moves.

FIG. 12 illustrates a Type I move for glutamate. At 141 the side chain has been removed. The first —$CH_2$— unit is added back at 142 with new torsional angle $\phi_1$. The generation according to $p^{int}$ and selection according to $p^{ext}$ of this angle ignores energy interactions with the other side chain rigid units not yet added. At 143, the next —$CH_2$— rigid unit is added back at angle $\phi_2$. Finally at 144, the last —$CO_2$ rigid unit is added at angle $\phi_2$. For this last step interaction energies with all the rigid units are considered in generating and selecting the new angle.

$W^{old}$ is the weight for the reverse move, the move from the proposed new structure to the current configuration. For this, the proposed side chain is removed and regrown in its current structure unit by unit. For the next, i'th, unit generate K−1 possible new torsional angles according to $p^{int}$, again ignoring interactions with units yet to be added. The K'th new angle is the current angle for that unit. The current torsional angle is selected. Although $p^{ext}$ is not used, normalization $w_i^{ext}$ is determined. After all units have been regrown at the current angles, $W^{old}$ is computed as the product of the normalizations.

The acceptance probability for the proposed side chain configuration is determined from equation 7 using $W^{new}$ and $W^{old}$.

Type II Move Generation

Type II moves alter a limited region of the amino acid backbone beginning at a randomly chosen backbone rigid unit of a randomly chosen binder peptide in a manner consistent with conformational constraints due to internal disulfide bonds. These random choices are made similarly to those for Type I moves.

In Type II moves, side chains attached to the altered rigid units move rigidly with their backbone rigid units.

For this move, important geometric constraints must be met. In a randomly chosen binder and at a randomly chosen backbone bond between adjacent rigid units, a torsional angle rotation by $\phi_0$ is made. Subsequent backbone torsional rotations are chosen so that a minimum number of rigid units undergo a spatial displacement. This constraint fixes a limited number (if any) of possible subsequent torsional angles as a function of $\phi_0$ so that at most 4 rigid units are spatially displaced and rotated with at most 3 additional rigid units undergoing a rotation. This move is an important aspect of this invention and is required to maintain the conformational constraint due to the disulfide bridge. Since only 7 rigid units are spatially modified, the Type II move preserves the 8 amino acid cycle (20 rigid units), including the cystine side chain.

Figure 13:
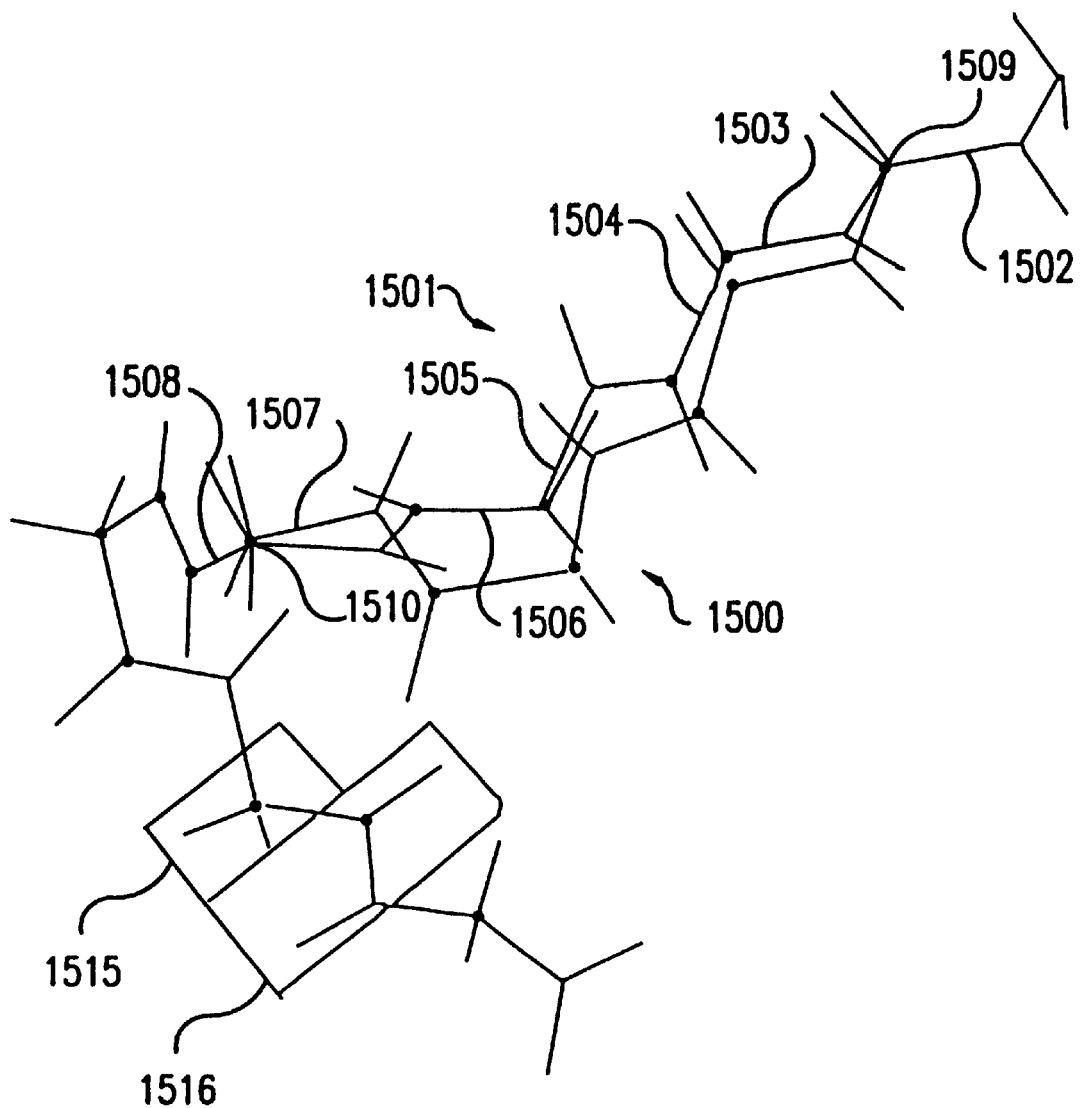
FIG. 13 is more detail for the step of FIG. 8 of processor generation of proposed modified structures by Type II moves.

FIG. 13 illustrates a Type II move of a poly-glycine 7-mer. Rigid unit positions are indicated generally by black circles as at 1509 with incoming bonds generally as at 1502. A $C_\alpha$ rigid unit (B unit) is illustrated in box 1515, and an amide bond (C unit) in box 1516. Backbone structure 1500 in transformed into structure 1501 by the Type II move generated by an initial rotation about bond 1502. Subsequent rotations about bonds 1503, 1504, 1505, 1506, 1507, and 1508 are thereby determined so that the rigid unit 1510 and at most three subsequent units undergo only a rotation without any spatial displacement. The four rigid units between units 1509 and 1510 undergo both a spatial displacement and a rotation as structure 1500 is transformed to structure 1501. No other backbone rigid units are altered.

Figure 14:
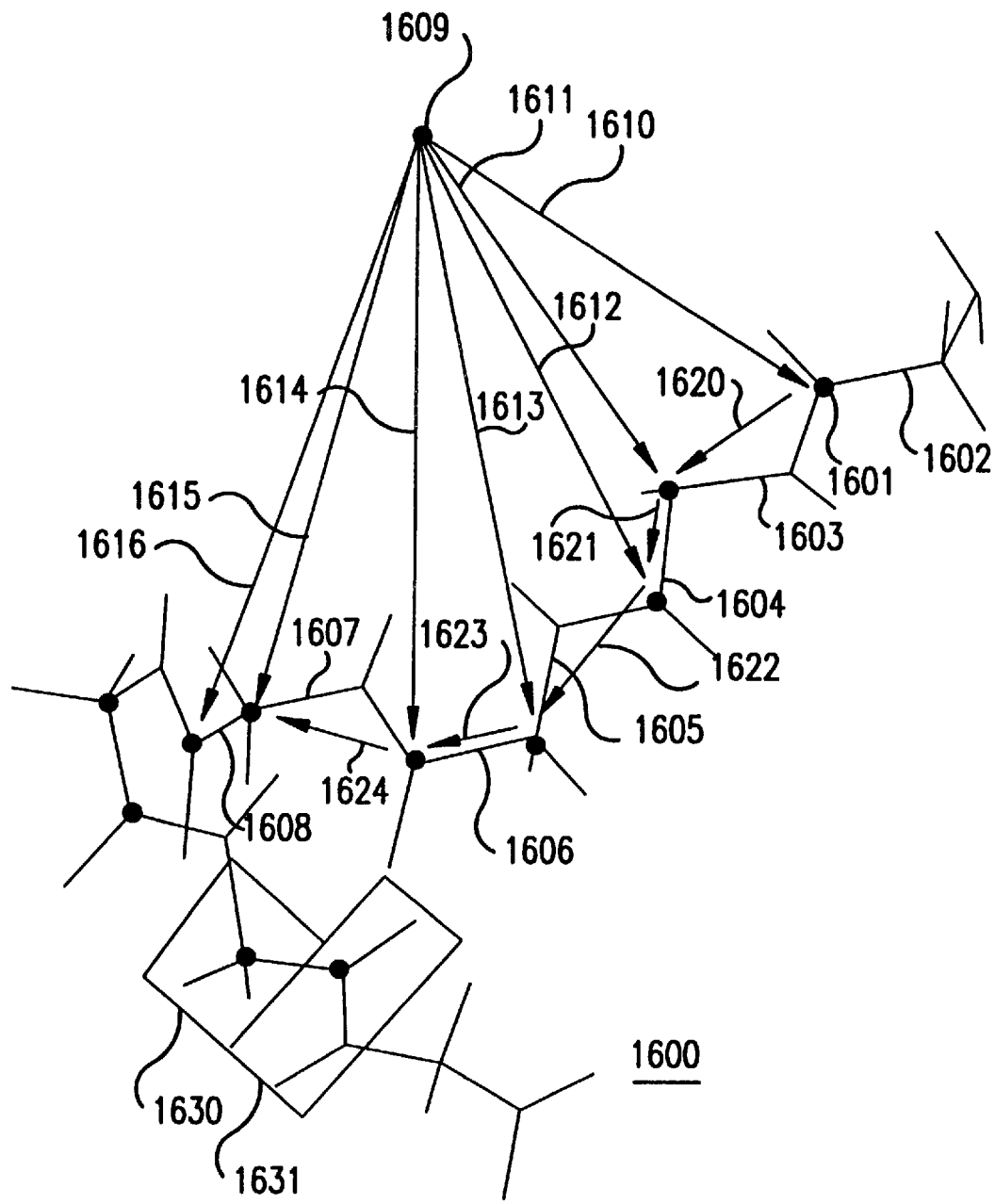
FIG. 14 is additional detail for the step of FIG. 8 of processor generation of proposed modified structures by Type II moves.

The derivation of these assertions, including expressions for the allowed angles, is in Section 8. Appendix: Concerted Rotation. FIG. 14 defines notation used in this Appendix: Concerted Rotation. Poly-glycine 7-mer backbone 1600 is the same as in FIG. 13. Rigid unit positions are indicated generally by black circles as at 1601 with incoming bonds generally as at 1602. The torsional rotations $\phi_0$ to $\phi_6$ are about bonds 1602 to 1608, respectively, between sequential, adjacent rigid units. The rigid unit position vectors $r_0$ to $r_6$, illustrated as vectors 1610 to 1616, respectively, define the position of these sequential rigid units with respect to a laboratory coordinate system with origin 1609. Summarizing this Appendix, the determination of the fixed torsional angles proceeds as follows. The allowed values for $\phi_1$ are the roots of equation 34, which depends on the $\phi_0$ driver angle and $\phi_2$ through $\phi_4$. But $\phi_2$ through $\phi_4$ can be determined in terms of $\phi_1$. Two solutions for $\phi_2$ are determined by equation 25 in terms of $\phi_1$. Two solutions for $\phi_3$ are determined by equation 29 in terms of the preceding $\phi$'s. Finally, a simple inversion of equation 32 determines one solution for $\phi_4$ in terms of the preceding $\phi$'s. Having found the allowed values of $\phi_1$, then equations 25, 29, and 32 determine corresponding allowed values for the other $\phi$'s, which in turn determine the alteration of the first four rigid units caused by the $\phi_0$ initial rotation.

More precisely, final torsional angles $\phi_0$ to $\phi_6$ determine position vectors $r_1$ to $r_4$ by applying rotation matrix 18 to equations 17 to obtain new position vectors in the laboratory coordinate system, the rotation matrices of equations 16 and 18 being determined by these final torsional angles. Position vectors $r_0$ and $r_5$ to $r_7$ do not change. Then rigid unit 0 is translated to position $r_0$; aligned so that its incoming bond axis is along the direction of the outgoing bond of unit $-1$; and finally rigidly rotated so that the end of its outgoing bond is at position $r_1$. Rigid unit 1 is then translated to position $r_1$; aligned so that its incoming bond axis is along the outgoing bond of unit 0; and rigidly rotated so that the end of its outgoing bond is at position $r_2$. Rigid units 2 to 6 are then added to the backbone in a similar fashion. In this fashion the Type II move geometry is determined. Any side chains attached to these rigid units are rigidly rotated when their parent unit is rotated.

The Type II rotation is chosen in the following manner. Using the configurational bias prescription, the Hamiltonian is divided into $u^{int}$ and $u^{ext}$. $u^{int}$ is preferably 0, or alternatively is the torsional energy associated with the rigid unit of interest, while $u^{ext}$ includes all remaining interaction energies. In the previous manner, $u^{int}$ determines $p^{int}$ according to which are generated K' candidate $\phi_0$ rotation angles. Preferably K' is 1. Then the geometric constraints are solved for each candidate $\phi_0$. Typically, but not always, 6K', denoted K, possible backbone alterations are obtained. One of these is selected by $p^{ext}$, determined by:

$$p^{ext}(\phi_{0,k}) = \frac{\exp[-\beta u_0^{ext}(\phi_{i,k})]}{W^{ext}(\phi_{i,k})} \quad (13)$$

$$W^{ext}(\phi_{i,k}) = \sum_{k=1}^{K} \exp[-\beta u_0^{ext}(\phi_{i,k})]$$

$u^{ext}$ includes all interactions not in $u^{int}$, that is all other backbone and side chain interactions. Because these determinations occur in torsional angle space and change the volume element in that space, the Jacobian, determined by equation 35, of the selected Type II move is also needed as a weight in the acceptance probability for detailed balance. This acceptance probability for Type II moves is:

$$\text{accept}(curr \rightarrow prop) = \min\left[1, \frac{W^{new} J^{new}}{W^{old} J^{old}}\right] \quad (14)$$

The weight and Jacobian of the reverse transformation from the proposed to the current structure are also needed in the acceptance probability for Monte Carlo detailed balance. These quantities are determined as follows. Using the proposed backbone structure just selected as the basis, generate a set of K'–1 new $\phi_0$ torsional angles according to $p^{int}$ and also include the current $\phi_0$ in the set. Then solve the geometric constraint to determine the permitted alterations. The current configuration, since it exists, must be among the permitted structures. From this set of permitted structures determine $W^{old}$ per equation 13. Then select the current configuration and compute the Jacobian $J^{old}$ per equation 35. This completes the determination or the acceptance probability.

Proline is approximated. Proline is not subject to Type I moves. However, proline is subject to normal Type II moves, with its side chain bond to the amino nitrogen broken. The side chain thus moves rigidly with its backbone rigid unit as in normal Type II move. To compensate for the broken bond approximation, the $C_\alpha$—N torsional energy amplitude in the proline backbone is set at approximately 5 kcal/mole. (By contrast the torsional energy in a typical amino acid of the $C_\alpha$—N bond is approximately 0.3 kcal/mole.) This invention is adaptable to other suitable approximations for proline. Alternatively, the proline side chain may be subject to alterations which preserve its cyclicity, such as for example, by an extension of the constraint scheme just described.

Program Detailed Description

Figure 15:
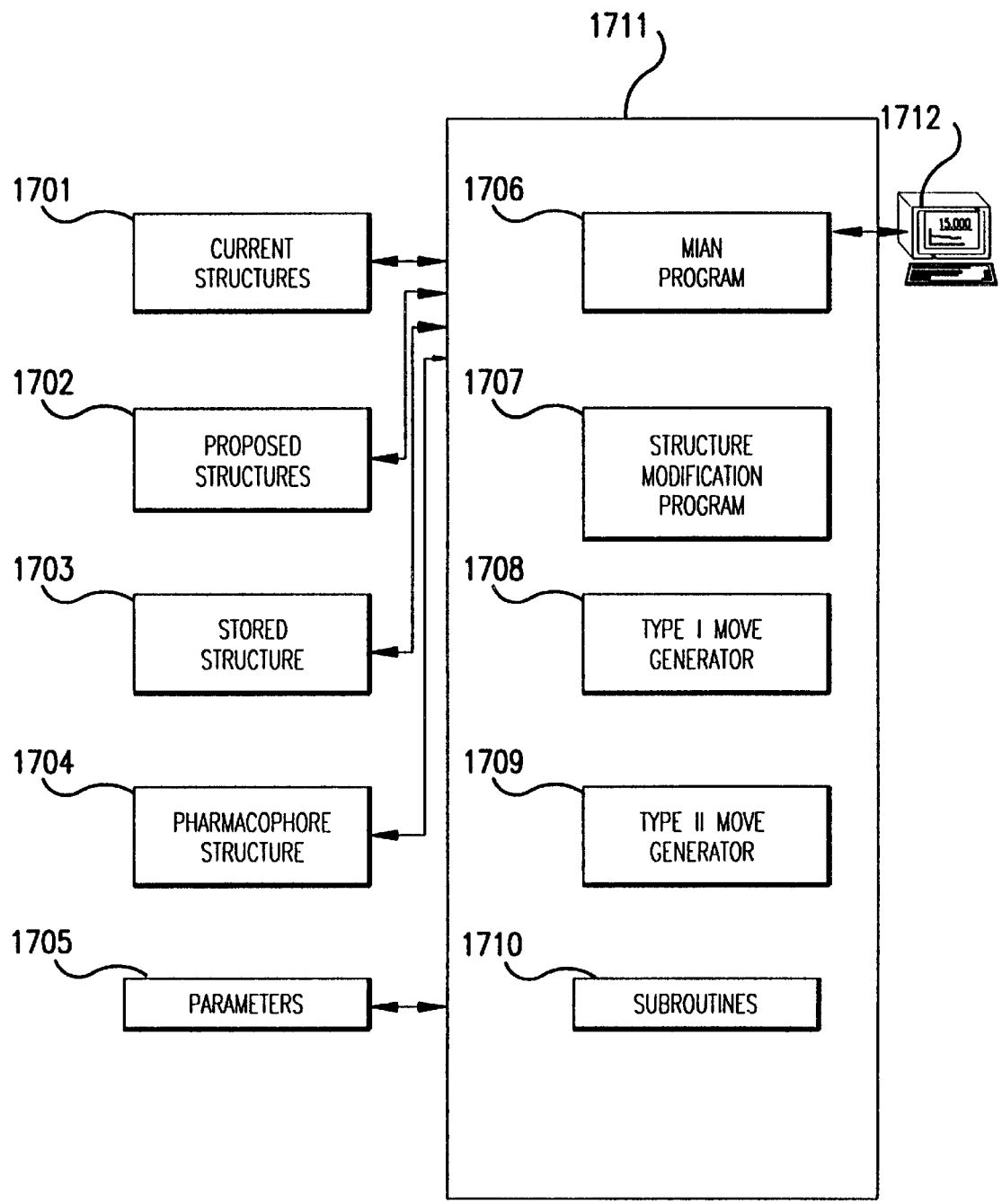
FIG. 15 is a structure for implementing the method of FIG. 8.

The following describes the construction and use of a computer method and apparatus to perform the method of step 5. The listing of this code is included in a microfiche appendix to this specification. FIG. 15 is a general view of the computer system and its internal data and program structures. To the left in FIG. 15 are the principal data structures of this method. Current structures 1701 contains the current structures of the N binders represented in memory as described. Proposed structure 1702 contains working memory areas used to generate a proposed new structure for one binder peptide. Structures 1701 and 1702 would typically be stored in RAM memory of the computer system, RAM memory being memory directly accessible to processor fetches. Stored structures 1703 contain similar memory representations of all the peptide structures generated, accepted, and selected for storage. This is typically stored on permanent disk file(s).

Candidate pharmacophore structures 1704 are input to the programs from either a disk file of the display and input unit 1712. The identified candidate structures are used to determine the $w'_{i,ij}$ in Eqn 11.

Parameters 1705 comprises several parts. First, are all the AMBER atomic interaction definitions and parameters. Second, are standard representations of the amino acids including component rigid units and atomic charge assignments. Third, are parameters controlling the run. These further comprise, by example, values for K and K', the Type I/II move branching ratio, the number of moves made in the simulations run, the simulation total energy record, etc. The parameters would typically be loaded from disk file(s) into RAM memory for manipulation during a simulation run.

Unit 1712 includes display and input devices-for monitoring and control. Depicted on the display are the total number of moves made in the current run and the course of the total energy, which is similar to that illustrated in FIG. 9.

Processor 1711 is loaded with necessary programs prior to a simulation run and executes the programs to perform the simulation method. The general structure consists of main program 1706, structure modification program 1707, Type I and II move generators 1708 and 1709, and subroutines 1710. The subroutines consist of common utility subprograms, such as for performing torsional rotations about bonds and computing interaction energies by the previous methods, and conventional library subprograms, such as for performing input and output and finding random numbers. Any scientifically adequate random number generator can be used. A reference for random number generators is Press et al., *Numerical recipes: the art of scientific computing,* Cambridge, U.K., Cambridge University Press, (1986), chapter 7. The invention is equally adaptable to other program structures that will occur to those skilled in computer simulation arts.

The preferred embodiment of these structure is an Indigo 2 workstation from Silicon Graphics (Mountain View, Calif.). Alternatively, any high performance workstation, such as products of Hewlett-Packard, IBM or Sun Microsystems, could be used. Preferably the data and program structures are coded in the C computer language. Alternatively any scientifically oriented language, such as Fortran, could be used. Conventional subroutine and scientific subroutine libraries are used where appropriate.

Figure 16:
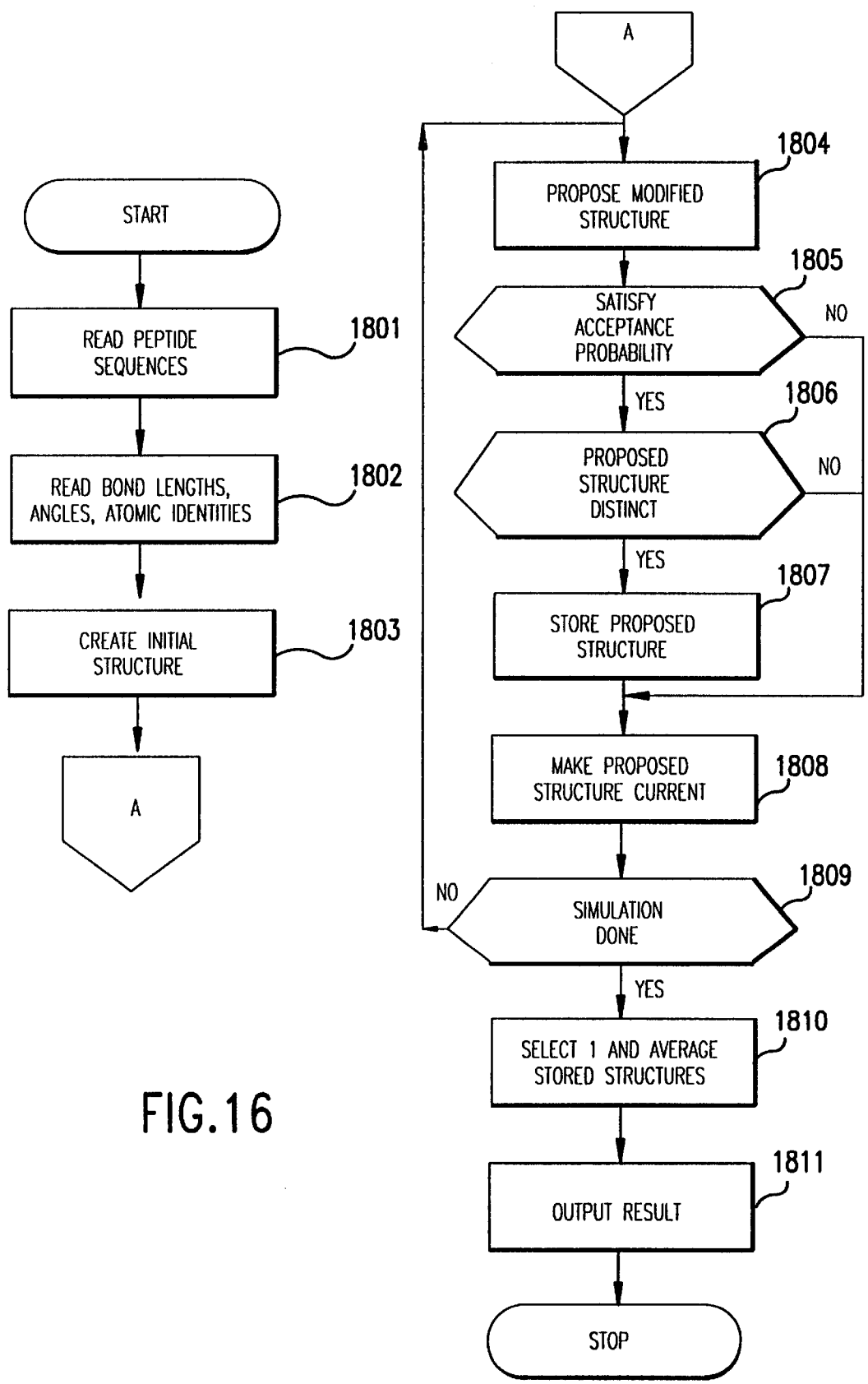
FIG. 16 is the main program structure of FIG. 15.

The program components will be now described in detail with reference to FIGS. 16, 17, 18, and 19. FIG. 16 illustrates main program 1706. The peptide sequences of the N binders are input at step 1801. All necessary AMBER parameters—bond lengths and angles, atomic types and charges, interaction parameters, amino acid definitions, etc.—are input at step 1802. Step 1803 creates initial structures from this input data. Rigid unit records for all rigid units are created and linked to represent peptides. The geometric structures of these peptides either are obtained from a prior run or are built by adding side chains to a prototypical backbone characteristic of the library of the binder. A prototypical backbone for the $CX_6C$ library is found in the microfiche appendix heading CX6C.CAR. The initial binder structures are stored in the current structure data areas in preparation for the beginning the main steps of the method.

Step 1804 begins the main loop of the simulation with the generation of a proposed modified structure for one of the binder peptides by structure modification program 1707. As part of proposed structure generation, an acceptance probability, accept(curr→prop) is determined as previously described. The proposed structure will be accepted at 1805 based on this probability. For example, a random number between 0 and 1 is generated, and the proposed structure accepted if the random number is less than the acceptance probability. If the proposed structure is accepted, then it is tested for sufficient distinctiveness at step 1806. This test is met if at least one atomic position in the proposed structure differs from the corresponding position in the current structure by at least approximately 0.2 Å. If the proposed structure is distinct, it is stored at 1807 in the structure store for later analysis. Whether distinct or not, the accepted proposed structure for the peptide replaces the corresponding current structure at step 1808.

The simulation is tested for completion at step 1809. Completion can be controlled by the operator at station 1712 depending on display of run progress-results. Alternatively, termination can be mechanically controlled. After completing a certain number of total moves after run energy equilibration, the moves being split between Types I and II according to the specified branching ratio, the run is terminated. The preferred number of total moves is 25,000, and the preferred Type I/II branching ratio is 4. Thus it is preferred to have 20,000 Type I and 5,000 Type II moves after equilibration per simulation run.

At step 1810, the stored structures are analyzed to determine both the consensus pharmacophore structure and the structures of the remainder of the binders. In the preferred embodiment, atomic positions in the equilibrated stored structures for each peptide are averaged to obtain the predicted geometric structure. The shared pharmacophore structure is obtained from the predicted structure of each peptide, again by averaging the shared position information for all peptides. Alternatively, before structure averaging, the structures generated for each binder can be clustered into similar groups and the clusters for each peptide separately averaged. The clusters would represent alternative peptide folding patterns. It is anticipated that because preferred binders are short peptides constrained by disulfide bridges, any alternative foldings identified will be structurally similar. The clustering can be done by the exemplary methods found in the previously referenced article Gordon et al. Fuzzy cluster analysis of molecular dynamics trajectories. Proteins: Structure, Function, and Genetics 14:249–264 (1992). For all analysis methods, the choice of the preferred number of stored moves is adjusted to achieve adequate estimated statistical position errors. Further, preferably, the results of three runs are combined to achieve increased statistical confidence.

Other information is also output. Particularly important is the course of the total energy for each peptide and for all the peptides, and the intra-molecular, consensus, and constraint components of the energies. These energy components are used in determining whether a consensus pharmacophore has been found. As previously described, this is preferably done by insuring that $H_{consensus}$ is small compared to the total energy and is minimized by a particular candidate pharmacophore. Also $H_{NMR}$ must be relatively small.

Finally at 1811, all results are output in a form usable for the subsequent steps 6 and 7 of FIG. 1. For example, this may be a particular file format suitable for subsequent lead compound search by a database query.

Figure 17:
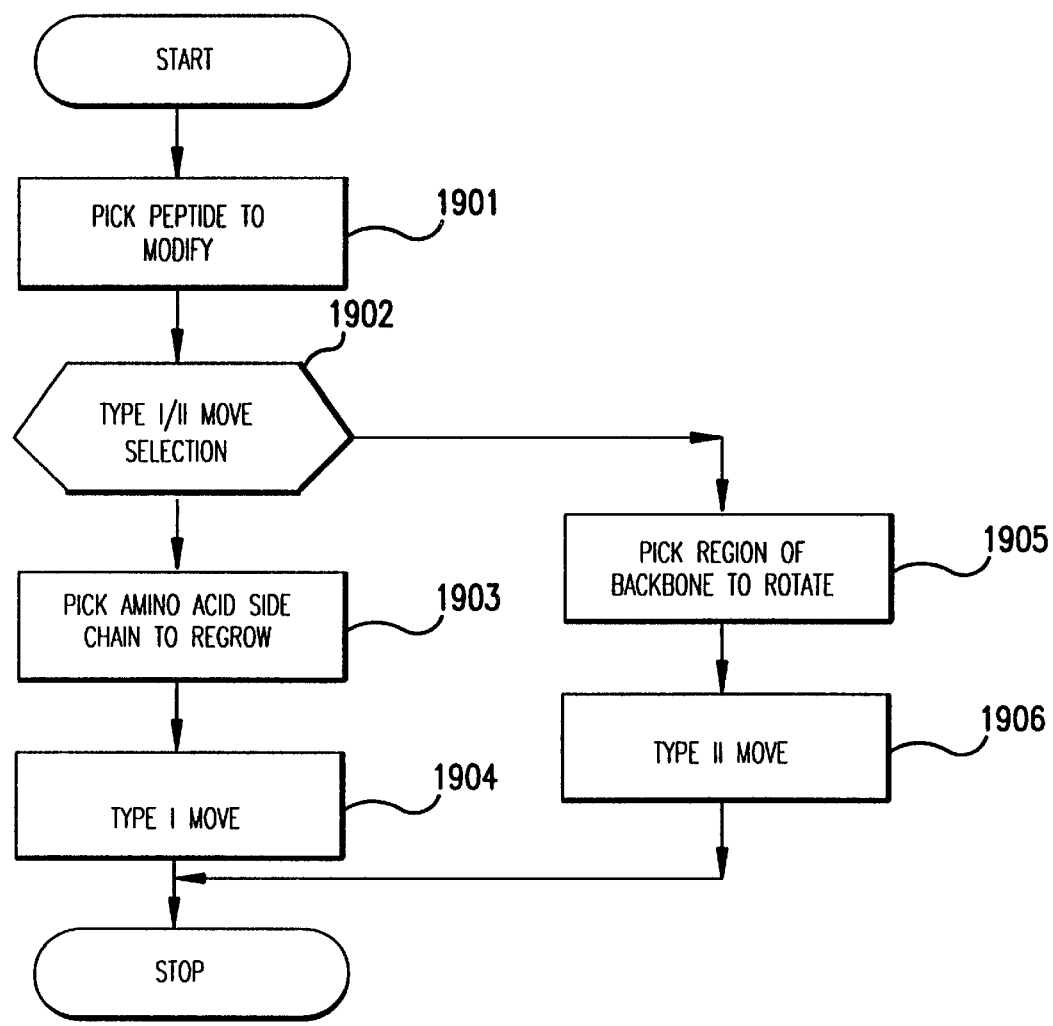
FIG. 17 is the structure modification program structure of FIG. 15.

Turning now to FIG. 17, structure modification program 1707 will be described. This is invoked from the main program at 1804. Upon entry, this program randomly picks one of the binder peptides at 1901 for which to generate a proposed structure and also picks which type of move to use at 1902. This latter random choice is made according to an adjustable Type I/II branching ratio (preferably 4). For a Type I move, step 1903 picks a random amino acid side chain of the selected peptide, and step 1904 invokes the Type I move program. (Proline has no Type I moves.) For a Type II move, step 1905 picks a random backbone bond between rigid units to rotate and also a random direction from the picked bond along which backbone rigid unit structure will be altered. Step 1906 invokes the Type II move program.

Figure 18A:
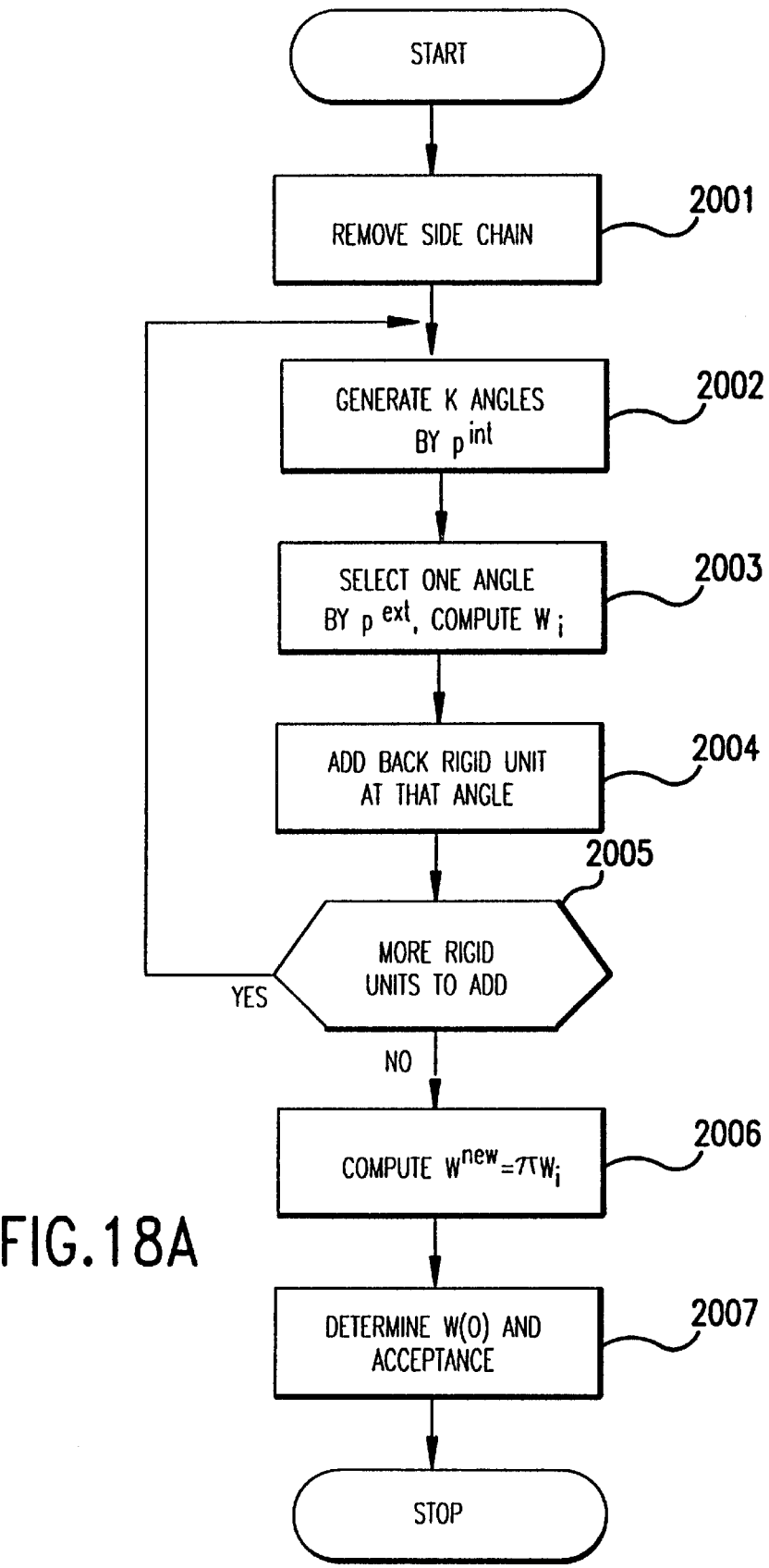
FIGS. 18A and 18B are the Type I move generator program structure of FIG. 17.
Figure 18B:
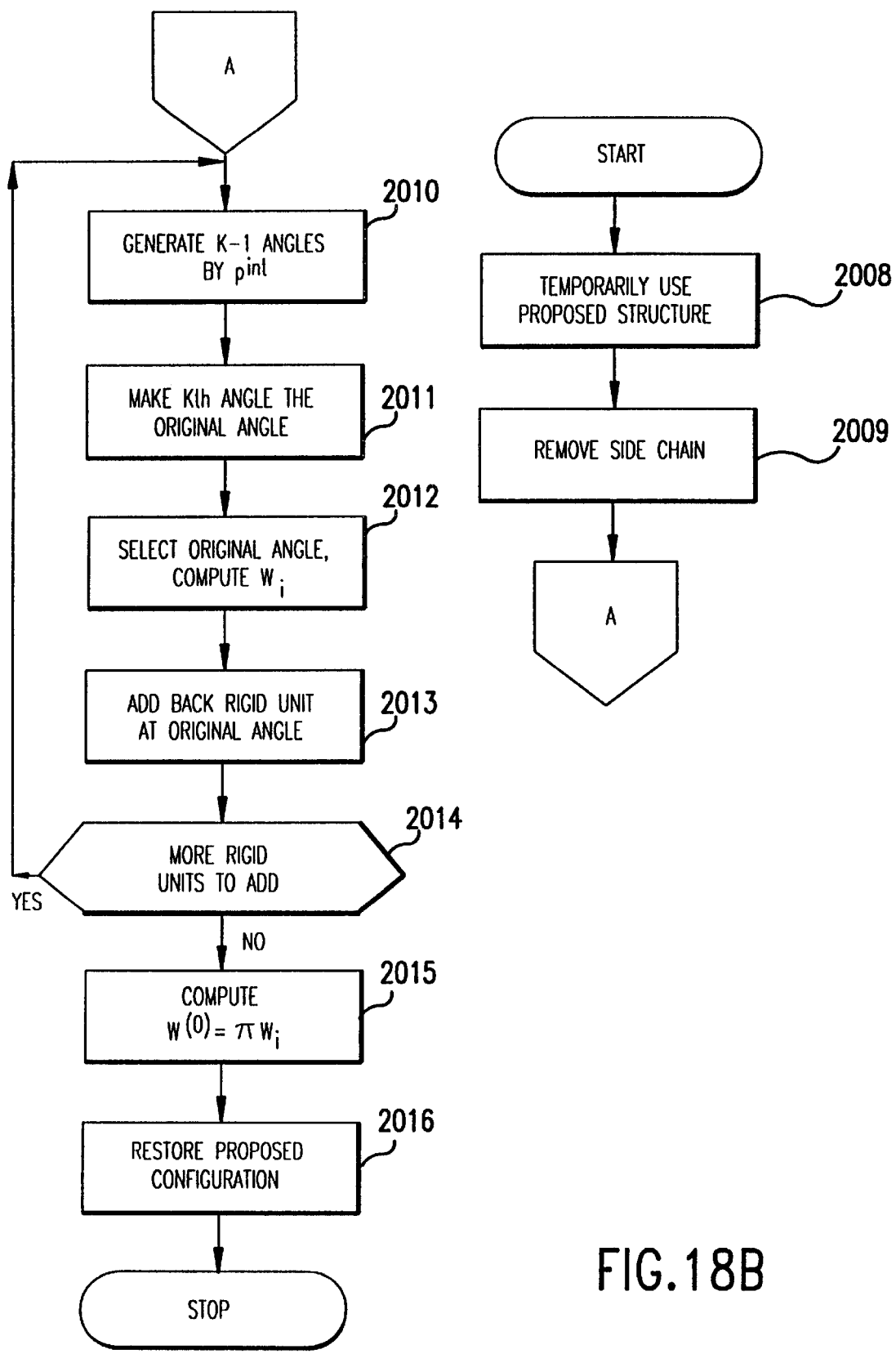

FIGS. 18A and 18B illustrate the Type I move generator 1708, which is defined by equations 6 and 7. With reference first to FIG. 18A, the proposed structure of the selected peptide is created from its current structure by removing the selected side chain. All intra-molecular interactions are subsequently determined with respect to the proposed structure absent side chain rigid units not yet regrown. K candidate new torsional angles for the next, i'th, rigid unit to add are generated by $p_i^{int}$ at 2002. Preferably K is between 10 and 100. Generation of these angles uses the conventional rejection method referenced in Press et al. at § 7.3. The weight $w_i^{ext}$ and $p_i^{ext}$ are determined for each of these candidate angles. This requires the rigid unit to be added to be rotated to the candidate angle using the previous rotation method. Candidate interaction energy is determined from candidate interatomic distances resulting from the candidate rotation. One of the candidate angles is probabilisticly selected at 2003 and the rigid unit added back at this torsional angle at 2004. If there are more units to add, which is tested at 2005, these steps are repeated. If not, the acceptance weight $W^{new}$ is determined as the product of the $w_i^{ext}$ at 2006. Lastly the old weight is determined at 2007. From the weights the move acceptance probability is found for use at 1805.

FIG. 18B details the determination 2007 of $W^{old}$, the weight for the reverse move from the proposed to the current side chain structure. Temporarily the proposed structure is used as a basis for energy determination at 2008, and then the current structure is restored at 2016, when this process is finished. The proposed side chain is removed at 2009 for regrowth rigid unit by rigid unit as in FIG. 18A. For the next, i'th, rigid unit to be added back, K–1 candidate angles are generated according to $p_i^{int}$ at 2010 with the current value of that angle for the-K-th candidate at 2011. As previously, the weight $w_i^{ext}$ is determined for these candidate angles at 2012. The rigid unit is added back at the current, K-th, angle at 2013. If there are more units to add, tested at 2014, these steps are repeated. If not, the acceptance weight $W^{old}$ is determined as the product of the $w_i^{ext}$ at 2006.

Figure 19A:
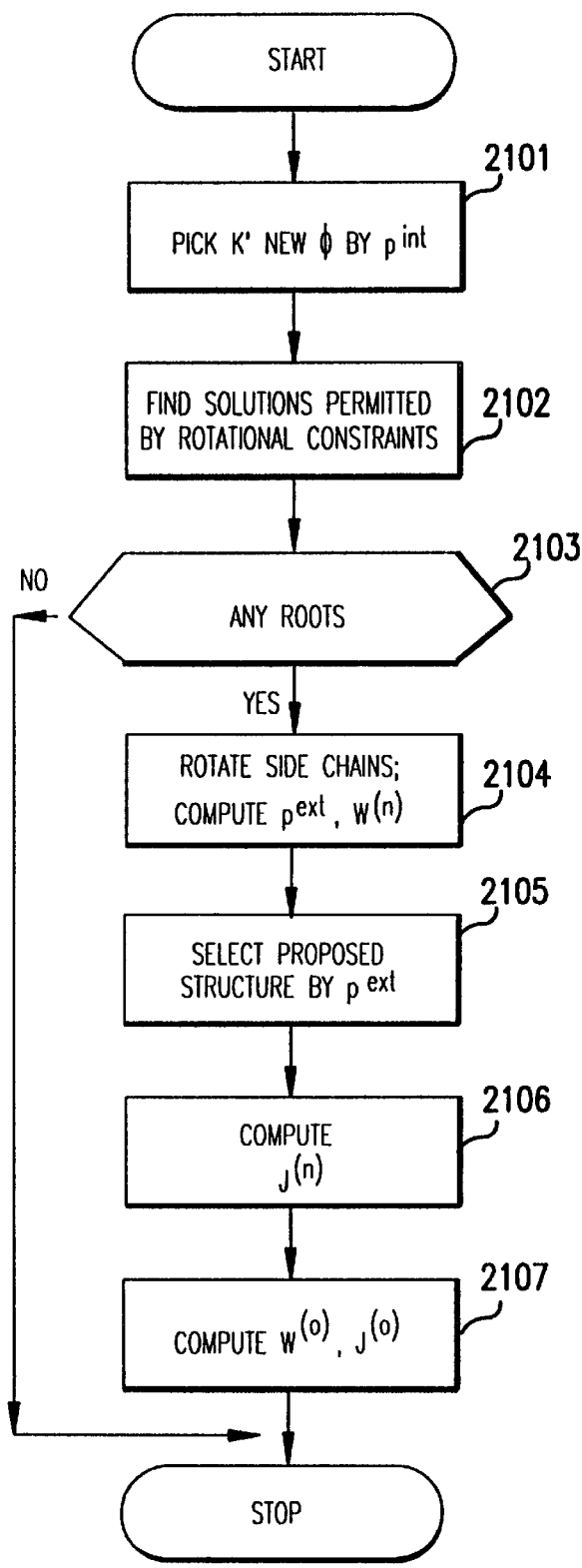
FIGS. 19A and 19B are the Type II move generator program structure of FIG. 17.
Figure 19B:
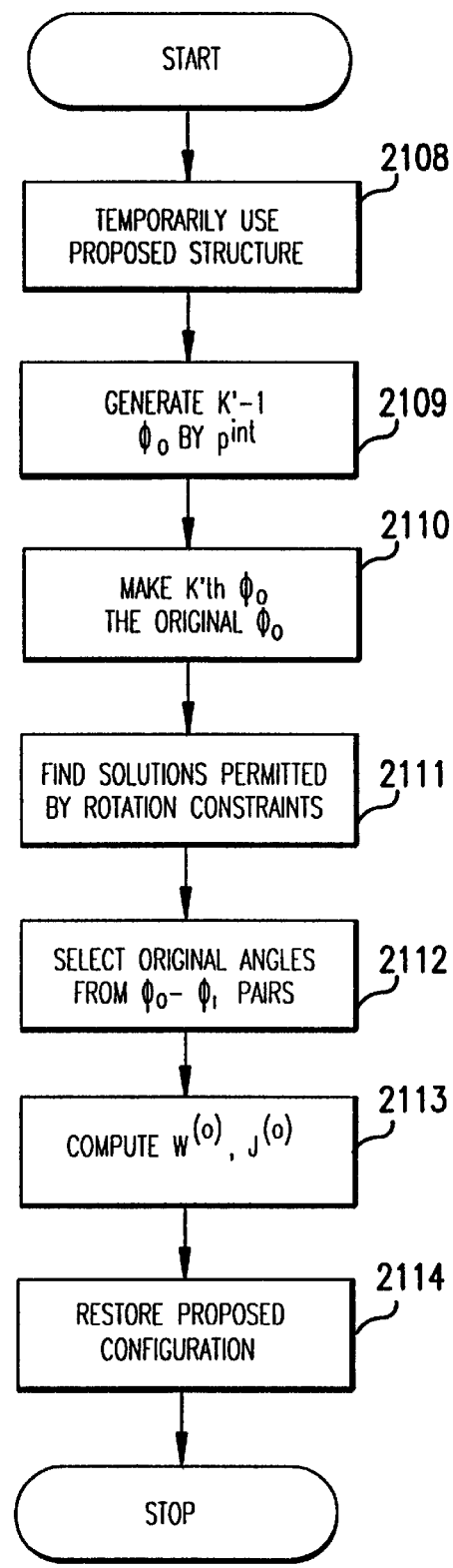

FIGS. 19A and 19B illustrate Type II move generator 1709, which is defined by equation 13 and 14 and the concerted rotation geometric constraints. With reference to FIG. 19A, K' candidate new torsional angles for the selected backbone bond are generated by $p^{int}$ using the rejection method. Preferably K' is 1. Torsional rotations about adjacent backbone bonds, in the selected direction along the backbone, permitted by the concerted rotation constraints are determined from the roots of equation 34 at 2102. Equation 34 depends on intermediate variables obtained from equations 25, 29, and 32 and determined in that order. The roots are simply found by searching the interval $[-\pi,\pi]$ in 0.04° increments. When a root is located in a 0.04° segment, it is refined with the bisection method referenced in Press et al. at § 9.1. It is expected on the average that six K' solutions will be found. If no roots are found at 2103, the candidate rotation is impossible and this move is skipped. If solutions exist, next, at 2104, $p^{ext}$ and $W^{new}$ are determined. Using the described rotation method, the backbone rigid units are rotated (with consequent spatial displacement of 4 units) to a candidate torsional angle solution about their mutual bonds. Additionally, any side chains attached to backbone rigid units are rigidly rotated using the same method. Having made these rotations, candidate interatomic distances and candidate interaction energies can be determined and used to obtain $p^{ext}$ for this candidate solution. One of the candidates is probabilisticly selected at 2104, and the backbone and any side chains are rotated according to this candidate into the proposed structure. The Jacobian of this transformation is determined at 2106 by equation 35. Lastly the old acceptance weight and Jacobian are determined at 2107. From the weights and Jacobians the move acceptance probability is found for use at 1805.

FIG. 19B details the determination 2107 of $W^{old}$ and $J^{old}$ for the reverse move from the proposed to the current side chain structure. Temporarily the proposed structure is used as the basis for energy determination at 2008, and the current structure is restored at 2016, when this process is finished. At 2109, a set of K'–1 candidate torsional angles is generated for the selected backbone bond according to $p^{int}$ using the rejection method and the current torsional angle is added to this set. If as preferred, K' is 1, this step results in a set with only the current angle. At 2111, similarly to 2102, the permitted torsional rotations about adjacent backbone bonds are determined from the equations expressing the concerted rotation constraints. Special care is taken to ensure that the original conformation is found by the root finding procedure. In particular, the search interval is centered on the known original $\phi_1$ and is made as small as necessary to isolate the root, which may be as small as 0.004° or smaller. The current structure must be among these solutions, since it exists. Select it at 2112. $W^{old}$ is computed from the candidate angle solution, making the candidate rotations and determining candidate interactions. Also the Jacobian, $J^{old}$, of the transformation is computed from the proposed to the current structure.

5.8. Consensus Structure Test

Having selected a candidate pharmacophore and determined a best possible consensus structure and best possible structures for the remainder of the binder molecules, the consensus test, step 6, tests whether a consensus structure has actually been found. A consensus pharmacophore structure consists of a spatial arrangement of chemically similar groups shared by all the N binders to high accuracy. Since an actual pharmacophore exists, the N specifically binding members of the screened libraries will share the actual structure. However, the remainder of binder molecules will share no other similar structures to such a high accuracy. Therefore, a structure consensus of the N binders is possible only if the candidate pharmacophore is the actual physical pharmacophore responsible for the actual binding. If the candidate selected relates to other parts of the binder molecules, no structure consensus will be found. Further, if the Monte Carlo determination attempts to impose a consensus on parts of the binder molecules that do not share structure, an inconsistent overall structure will be obtained for the remainder of the binder molecules.

Therefore, two preferred consensus tests are applied: one test asks whether a consistent candidate pharmacophore has been obtained, and a second test asks whether consistent structures have been obtained for the remainder of the binder molecules. Both tests have a preferred absolute and a less preferred relative version.

There are two portions for the first test. First, are all the consensus pharmacophore distances obtained in the N binders within at least a specified distance, preferably approximately 0.25 Å, of each other? Second, is the consensus energy, $H_{consensus}$, relatively small compared to the total molecular energy (e.g., less than at most approximately 5–10% of the total molecular energy) as determined by the Monte Carlo method?

There are also two portions of the second test. First, can the intramolecular distances predicted by the Monte Carlo method be confirmed by additional distance measurements? Second, since the Monte Carlo method utilizes distance constraints previously measured, one or more of these measurement constraints can be ignored and the predicted distance checked against that measured distance. Tolerances for these tests are distance agreements of at least specified distances, e.g., approximately 0.5 Å, in each binder.

The two preferred tests have been described in the absolute version as requiring checks against absolute tolerances. Alternatively, the values of the pharmacophore distance differences among the binders, $H_{consensus}$, and the differences of the predicted and measured distances can be accumulated for all the possible candidate pharmacophores, the candidate selected being that one minimizing these departures. Therefore, the selected candidate will have the minimum values for the differences of the pharmacophore distances in the binders, the minimum value for $H_{consensus}$, and the minimum values of the differences of predicated from measured distances.

This invention is adaptable to other tests that evaluate the consistency of the consensus structure obtained for the candidate pharmacophore and the-accuracy of the structure obtained for the remainder of the binder molecules.

5.9. Lead Compound Determination

Having started at step 1 with a target of interest, upon completion of step 6 of FIG. 1 a high resolution pharmacophore structure has been determined as well as supporting structures of the N binder peptides. This high resolution structure is used in step 7 to determine lead compounds for use as a drug that will bind to the original target of interest.

Thus, one or more lead compounds are determined, that share a pharmacophore specification with the determined consensus pharmacophore structure. This determination can be preferably done by one of several methods: by a search of a database of potential drug compounds or of chemical structures (e.g., the Standard Drugs File (Derwent Publications Ltd., London, England), the Bielstein database (Bielstein Information, Frankfurt, Germany or Chicago), and the Chemical Registry (CAS, Columbus, Ohio)) to identify compounds that contain the pharmacophore specification; by modification of a known lead compound to include the pharmacophore specification; by synthesizing a de novo structure containing the pharmacophore specification; or by modification of binders to the target molecule (e.g., isolated in step 2) outside of the pharmacophore structure to render the binder more attractive for use as a drug (e.g., to increase half-life, solubility, ability to achieve desired in vivo localization).

Database search queries are based not only on chemical property information but also on precise geometric information. Computer-based approaches rely on database searching to find matching templates; Y. C. Martin, Database searching in drug design, J. Medicinal Chemistry, vol. 35, pp 2145–54 (1992), which is herein incorporated by reference. Existing methods for searching 2-D and 3-D databases of compounds are applicable to this step. Lederle of American Cyanamid (Pearl River, N.Y.) has pioneered molecular shape-searching, 3D searching and trend-vectors of databases. Commercial vendors and other research groups have enhanced searching capabilities [MACSS-3D, Molecular Design Ltd. (San Leandro, Calif.); CAVEAT, Lauri, G. et al., University of California (Berkeley, Calif.); CHEM-X, Chemical Design, Inc. (Mahwah, N.J.)].

The pharmacophore structure determined in this invention is adaptable to any of these methods and sources of chemical database searching and to the enumerated non-database methods. Output will be lead compounds suitable for drug design. An important aspect of this invention is that the high resolution pharmacophore structure will lead-to highly targeted leads. Lower resolution structures result in a geometric increase in the number of lead compound query matches. Example 1 illustrates this effect.

5.10. Appendix: Concerted Rotation

Since the preferred molecules under consideration are conformationally constrained by disulfide bridge(s), a Monte Carlo move that preserves this constraint is required. The "concerted rotation" scheme used for alkanes can be extended to allow rotation of the torsional angles in conformationally constrained peptides. This appendix describes this extension. Dodd et al. (1993) discusses the original, restricted method. (The essential extensions are expressed in equations 27, 28, and 34.) This method is directly applicable to the cyclic residue of proline, and an alternative embodiment of this invention would thermally perturb proline with a move of similar geometric constraints.

FIG. 14 illustrates the geometry under consideration. Illustrated backbone 1600 is a poly-glycine 7-mer. Rigid unit positions are indicated generally by black circles as at 1601 with incoming bonds generally as at 1602. The torsional rotations $\phi_0$ to $\phi_6$ are about bonds 1602 to 1608, respectively, between sequential, adjacent rigid units. The rigid unit position vectors $r_0$ to $r_6$, illustrated as vectors 1610 to 1616, respectively, define the position of these sequential rigid units with respect to a laboratory coordinate system with origin 1609. A $C_\alpha$ rigid unit (B unit) is illustrated in box 1630, and an amide bond (C unit) in box 1631.

To formulate this method, let us consider rotating about seven torsional angles, which will displace the root positions and rotate four rigid units, rotate up to three additional ones, and leave the rest of the peptide fixed. The root position of a rigid unit is the C, position for a B unit, the C position for a C unit, the C position for a $CH_2$ unit, and the S position for the S unit in cystine. If unit 5 is a C unit, however, $r_5$ is defined to be the backbone amino nitrogen position of that unit. For each unit, let us define $\theta_i$ to be the fixed angle between the incoming and outgoing bonds. Thus, $\theta_i=0$ for a C unit, and $\theta_i \approx 70.5°$ for all others.

The method leaves the positions $r_i$ of units $i \leq 0$ or $i \geq 5$ fixed. The torsion $\phi_o$ is changed by an amount $\delta\phi_o$. The values of $\phi_i$, $1 \leq i \leq 6$ are then determined so that only the positions $r_i$ of units $1 \leq i \leq 4$ are changed.

The method requires several definitions to present the solution for the new torsional angles. The bond vectors are defined to be the difference in position between unit i and unit i−1, as seen in the coordinate system of unit i:

$$l_i = r_i^{(i)} - r_{i-1}^{(i)}. \quad (15)$$

Bond vectors $l_1$ to $l_5$ are illustrated in FIG. 14 at 1620 to 1624, respectively. The length and orientations of the $l_i$ are determined by rigid unit structure and the length and angle AMBER parameters for bonds between atom types. The coordinate system of i is such that the incoming bond is along the $\hat{x}$ direction. Thus $l_i = l_i \hat{x}$ if atoms $r_i$ and $r_{i-1}$ are directly bonded to each other and has x- and y-components otherwise. Here $\hat{x}$ is a fixed unit vector along the x direction. Now define a rotation matrix that transforms from the coordinate system of unit i+1 to unit i $$T_i = \begin{pmatrix} \cos\theta_i & \sin\theta_i & 0 \\ \sin\theta_i\cos\phi_i & -\cos\theta_i\cos\phi_i & \sin\phi_i \\ \sin\theta_i\sin\phi_i & -\cos\theta_i\sin\phi_i & -\cos\phi_i \end{pmatrix} \quad (16)$$

The positions of the units in the frame of unit 1 are, thus, given by:

$$r_1^{(1)} = l_1$$

$$r_2^{(1)} = l_1 + T_1 l_2$$

$$r_3^{(1)} = l_1 + T_1(l_2 + T_2 l_3) \quad (17)$$

$$r_4^{(1)} = l_1 + T_1(l_2 + T_2(l_3 + T_3 l_4))$$

Further define the matrix that converts from the frame of reference of unit 1 to the laboratory reference frame $$T_1^{lab} = [\cos\psi I + nn^T(1-\cos\psi) + M\sin\psi]A. \quad (18)$$

where $$M = \begin{pmatrix} 0 & -n_z & n_y \\ n_z & 0 & -n_x \\ -n_y & n_x & 0 \end{pmatrix} \quad (19)$$

and $$n = \frac{\hat{x} \times r}{|\hat{x} \times r|}$$

$$\cos\psi = \frac{r \cdot \hat{x}}{|r||\hat{x}|}$$

$$\sin\psi = \frac{|r \times \hat{x}|}{|r||\hat{x}|},$$

where r is the axis of the bond coming into unit 1. The matrix A is a rotation about $\hat{x}$ and is defined so that $Al_1 = \Delta r$:

$$A = \begin{pmatrix} 1 & 0 & 0 \\ 0 & c & -s \\ 0 & s & c \end{pmatrix} \quad (20)$$

where $$c = (l_{1y}\Delta r_y + l_{1z}\Delta r_z)/(\Delta i\ r_y^2 + \Delta r_z^2) \quad (21)$$

$$s = (-l_{1z}\Delta r_y + l_{1y}\Delta r_z)/(\Delta r_y^2 + \Delta r_z^2).$$

Here $\Delta R = A[T_1^{lab}]^{-1}(r_1 - r_0)$ if unit 0 is a C unit. Otherwise, $\Delta r = l_1$.

The method proceeds by solving for $\phi_i$, $2 \leq i \leq 6$, analytically in terms of $\phi_1$. Then a nonlinear equation is solved numerically to determine which values of $\phi_1$, if any, are possible for the chosen value of $\phi_0$.

The derivation proceeds in the coordinate system of unit 1, after it has been rotated by the chosen $\phi_0$. Define $$t = r_5^{(1)} - l_1 = [T_1^{lab}]^{-1}(r_5 - r_0) - l_1. \quad (22)$$

If $\theta_3 \neq 0$ and $\theta_5 \neq 0$, one can see from FIG. 14 that the distance between unit 3 and unit 5 is known and equal to $$q_1^2 = (l_{4x}\cos\theta_4 - l_{4y}\sin\theta_4 + l_{5x})^2 + (l_{4x}\sin\theta_4 + l_{4y}\cos\theta_4 + l_{5y})^2 \quad (23)$$

But this distance can also be written as $$q_1^2 = |x - T_2 l_3|^2 \quad (24)$$

$$x = T_1^{-1} t - l_2.$$

Equating these two results, two values of $\phi_2$ are possible $$\phi_2' = \arcsin(c_1) - \arctan(x_y/x_z) - H(x_z) \quad (25)$$

$$\phi_2'' = \pi - \arcsin(c_1) - \arctan(x_y/x_z) - H(x_z)$$

with $$H(x) = \begin{cases} 0, & x > 0 \\ \pi, & x < 0 \end{cases} \quad (26)$$

The constant $c_1$ is given by $$c_1 = \begin{cases} \dfrac{q_1^2 - x^2 - l_3^2 + 2x_x(\cos\theta_2 l_{3x} + \sin\theta_2 l_{3y})}{-(\sin\theta_2 l_{3x} - \cos\theta_2 l_{3y})(x_y^2 + x_z^2)^{1/2}}, & \theta_3 \neq 0, \theta_5 \neq 0 \\ \dfrac{l_{3x} + l_{4x} + l_{5x}\cos\theta_4 - x_x\cos\theta_2}{\sin\theta_2(x_y^2 + x_z^2)^{1/2}}, & \theta_3 = 0, \theta_5 \neq 0 \\ \dfrac{(r_5 - r_2)\cdot(r_6 - r_5)/l_6 - l_5 - l_{4x}\cos\theta_4 - x_x(\cos\theta_2 l_{3x} + \sin\theta_2 l_{3y})}{(\sin\theta_2 l_{3x} - \cos\theta_2 l_{3y})(x_y^2 + x_z^2)^{1/2}}, & \theta_3 \neq 0, \theta_5 = 0 \\ \dfrac{l_{3x}\cos\theta_4 - x_x(\cos\theta_2 l_{3x} + \sin\theta_2 l_{3y})}{(\sin\theta_2 l_{3x} - \cos\theta_2 l_{3y})(x_y^2 + x_z^2)^{1/2}}, & \theta_3 = 0, \theta_5 = 0 \end{cases} \quad (27)$$

where x is given by Eqn. 24 if $\theta_5 \neq 0$, and $x = T_1^{-1}[T_1^{lab}]^{-1}(r_6 - r_5)/l_6$ if $\theta_5 = 0$. Clearly for there to be a solution $|c| \leq 1$. The last three equations for $c_1$ were determined by conditions similar to equating Eqns. 23 and 24. For $\theta_3 = 0$, $\theta_5 \neq 0$, the x component of $r_5^{(3)} - r_3^{(3)}$ is known to be equal to $(l_{4x} + l_5\cos\theta_4)$. For $\theta_3 \neq 0$, $\theta_5 = 0$, the x component of $r_5^{(5)} - r_3^{(5)}$ is known to be equal to $l_{5x} + l_{4x}\cos\theta_4$. For $\theta_3 = 0$, $\theta_5 = 0$, the angle between $r_3 - r_2$ and $r_6 - r_5$ is known to be equal to $\theta_4$.

To determine $\theta_3$ two expressions for $|r_5 - r_4|^2$ are again equated to determine that:

$$c_2 = \frac{l_5^2 - y^2 - l_4^2 + 2y_x(\cos\theta_3 l_{4x} + \sin\theta_3 l_{4y})}{2(\sin\theta_3 l_{4x} - \cos\theta_3 l_{4y})(y_y^2 + y_z^2)^{1/2}} \quad (28)$$

$$\phi_3' = \arcsin(c_2) - \arctan(y_y/y_z) - H(y_z) \quad (29)$$

$$\phi_3'' = \pi - \arcsin(c_2) - \arctan(y_y/y_z) - H(y_z),$$

where $y = T_2^{-1}(T_1^{-1}t - l_2) - l_3$. Again, $|c_2| \leq 1$ for there to be solution.

If $\theta_5 \neq 0$, the value of $\phi_4$ can now be determined from:

$$r_5^{(1)} = r_4^{(1)} + T_1 T_2 T_3 T_4 l_5. \quad (30)$$

Defining $$q_3 = T_3^{-1} T_2^{-1} T_1^{-1} [T_1^{lab}]^{-1}(r_5 - r_4). \quad (31)$$

the equations that define $\phi_4$ are given by $$q_{3y} = \cos \phi_4 (\sin \theta_4 l_{5x} - \cos \theta_4 l_{5y}) \quad (32)$$

$$q_{3z} = \sin \phi_4 (\sin \theta_4 l_{5x} - \cos \theta_4 l_{5y})$$

This is a successful rotation if the position of $r_6$ is successfully predicted. That is, the equation $$r_6^{(1)} - r_5^{(1)} = T_1 T_2 T_3 T_4 T_5 l_6 = [T_1^{lab}]^{-1} (r_6 - r_5). \quad (33)$$

must be satisfied. Consider the x-component, which implies $$F_5(\phi_1) = \begin{cases} (r_6^{(1)} - r_5^{(1)})^T T_1 T_2 T_3 T_4 \hat{x} - (l_{6x} \cos\theta_5 + l_{6y} \sin\theta_5) = 0, \theta_5 \neq 0 & (34) \\ (r_4 - r_3) \cdot (r_6 - r_5) - l_4 l_6 \cos\theta_4 = 0, \theta_3 \neq 0, \theta_5 = 0 \\ |r_6 - r_4| - [(l_{6x} + l_{5x})^2 + l_{5y}^2]^{1/2} = 0, \theta_3 = 0, \theta_5 = 0 \end{cases}$$

must be satisfied if the rotation is successful. The equations for the case $\theta_5 = 0$ clearly express the geometric conditions required for a successful rotation.

Eqn. 34 is the nonlinear equation for $\theta_1$ because $\theta_2$, $\theta_3$, and $\theta_4$ are determined by Eqns. (25), (29), and (32) in terms of $\phi_1$. This equation has between zero and four values for each value of $\phi_1$, however, due to the multiple root character of Eqns. (25) and (29). The equation is solved by searching the region $-\pi < \phi < \pi$ for zero crossings. The search is in increments of $\approx 0.04°$. These roots are then refined by a bisection method.

The transformation from $\phi_i$, $0 \leq i \leq 6$ to the new solution which is constrained to change only $r_i$, $1 \leq i \leq 4$ actually implies a change in volume element in torsional angle space. This change in volume element is the reason for the appearance of the Jacobian in the acceptance probability. The Jacobian of this transformation is calculated in Dodd et al. (1993) at pp. 991–93. It is slightly different here since root position $r_5$ is not necessarily the head position. The Jacobian is given by.

$$J = \frac{1}{|det B|} \quad (35)$$

where the 5×5 matrix B is given by $B_{ij} = [u_j \times (r_5 - h_j)]_i$ for $i \leq 3$ and $B_{ij} = [u_j \times (r_6 - r_5)/|r_6 - r_5|]_{i-3}$ for $i = 4, 5$. Here $h_i = r_i$, except that $h_5$ is the head position even if $\theta_5 = 0$, and $u_i$ is the incoming bond vector for unit i.

Repeated application of the concerted rotation may lead to a slightly imperfect structure, due to numerical precision errors. In an alternative embodiment, peptide geometry would be restored to an ideal state by application of the Random Tweek algorithm after several thousand moves (Shenkin et al., 1987, Biopolymers 26:2053–85)

The invention is further described in the following examples which are in no way intended to limit the scope of the invention.

6. EXAMPLES

6.1. Relation Between Effectiveness of Potential Drug Identifications and Pharmacophore Geometric Tolerance Searches of a drug library well known to medicinal chemists, the Standard Drugs File (Derwent Publications Ltd., London, England), illustrate the geometric increase in the number of compounds found (and thus decrease in expected effectiveness of identification of potential drugs) as pharmacophore geometric tolerance is increased. Table 4 tabulates the results.

TABLE 4

| Tolerance (Å) | Number of drug compounds |
|---|---|
| 5HT3 (5 Hydroxytryptophan) | |
| 2.0 | 64 |
| 1.0 | 35 |
| 0.5 | 27 |
| 0.25 | 12 |
| 0.10 | 1 |
| Dopamine | |
| 2.0 | 188 |
| 1.0 | 185 |
| 0.5 | 60 |
| 0.25 | 48 |
| 0.10 | 5 |

The pharmacophores are two well known neurotransmitters, 5-hydroxytryptophan and dopamine. As the tolerance of one distance in the pharmacophore structure is decreased from 2.0 to 0.1 Å, the number of compounds retrieved from the database is listed. The advantage of achieving pharmacophore resolution better than approximately 0.25 Å is clear.

If the tolerance of three distances were involved, the expected number of compound retrieved would be the cube of these numbers. For the dopaminergic pharmacophore, the number of lead compounds would decrease from over $6.5 \times 10^6$ to about 125 as three tolerances were decreased from 2.0 Å to 0.1 Å.

This example illustrates the geometric increase in the number of leads identified as pharmacophore geometry is less well defined. It is thus a very preferred-aspect of this invention that the computational method results in determining pharmacophore structure accurate to at least approximately 0.25 to 0.30 Å. Thus an exponentially large improvement in lead compound selection for drug design can be expected to result from this invention.

6.2. Expression and Purification of Target Proteins

Target molecules that are proteins, for example ras, raf, vEGF and KDR, are expressed in the *Pichia pastoris* expression system (Invitrogen, San Diego, Calif.) and as glutathione-S-transferase (GST)-fusion proteins in *E. coli* (Guan and Dixon, 1991, Anal. Biochem. 192:262–267).

The cDNAs of these target proteins are cloned in the Pichia expression vectors pHIL-S1 and pPIC9 (Invitrogen). Polymerase chain reaction (PCR) is used to introduce six Histidines at the carboxy-terminus of these proteins, so that this His-tag can be used to affinity-purify these proteins. The recombinant plasmids are used to transform Pichia cells by the spheroplasting method or by electroporation. Expression of these proteins is inducible in Pichia in the presence of methanol. The cDNAs cloned in the pHIL-S1 plasmid are expressed as a fusion with the PHO1 signal peptide and hence are secreted extracellularly. Similarly cDNAs cloned in the pPIC9 plasmid are expressed as a fusion with the α-factor signal peptide and hence are secreted extracellularly. Thus, the purification of these proteins is simpler as it merely involves affinity purification from the growth media. Purification is further facilitated by the fact that Pichia secretes very low levels of homologous proteins and hence the heterologous protein comprises the vast majority of the protein in the medium. The expressed proteins are affinity purified onto an affinity matrix containing nickel. The bound proteins are then eluted with either EDTA or imidazole and are further concentrated by the use of centrifugal concentrators.

As an alternative to the Pichia expression system, the target proteins are expressed as glutathione-S-transferase (GST) fusion proteins in E. coli. The target protein cDNAs are cloned into the PGEX-KG vector (Guan and Dixon, 1991, Anal. Biochem. 192:262–267) in which the protein of interest is expressed as a C-terminus fusion with the GST protein. The pGEX-KG plasmid has an engineered thrombin cleavage site at the fusion junction that is used to cleave the target protein from the GST tag. Expression is inducible in the presence of IPTG, since the GST gene is under the influence of the tac promoter. Induced cells are broken up by sonication and the GST-fusion protein is affinity purified onto a glutathione-linked affinity matrix. The bound protein is then cleaved by the addition of thrombin to the affinity matrix and recovered by washing, while the GST tag remains bound to the matrix. Milligram-quantities of recombinant protein per liter of E. coli culture are expected to be obtainable in this manner.

6.3. Synthesis and Screening of Polysome-based Libraries Encoding Random Constrained Peptides of Various Lengths

6.3.1. Preparation of DNA Templates

DNA libraries with a high degree of complexity are made as two components: an expression unit, and a semi-random (or degenerate) unit. The expression unit has been synthesized chemically as an oligonucleotide (termed T7RBSATG), and contains the promoter region for bacteriophage T7 RNA polymerase, a ribosome binding site, and the initiating ATG codon. The random region, also synthesized as an oligonucleotide (termed MMN6) contains a region complementary to the expression unit, the antisense version of the codons specifying Cys-X$_6$-Cys, and a restriction site (BstXI). The library is constructed by annealing 100 pmol of oligonucleotide T7RBSATG [having the sequence 5'ACTTCGAAATTAATACGACTCACTAT-AGGGAGACCACAACGGTTTCCCTCCAGAAAT AATTTTGTTTAACTTTAACTTTAAGAAG-GAGATATACATATGCAT3' (SEQ ID NO:2)]; and oligonucleotide MMN6 [having the sequence 5'CCCAGAC-CCGCCCCCAGCATTGTGGGTTCCAAC GCCCTCTAGACA[MNN]$_6$ACAATG TATATCTCCT-TCTT3' (SEQ ID NO:3); M=A or C, N=G, A, T, or C], and extending the DNA in a reaction mixture containing 10–100 units of Sequenase (United States Biochemical Corp., Cleveland, Ohio), all four dNTPS (at 1 mM), and 10 mM dithiothreitol for 30 min at 37° C. The extended material is then digested with BstXI, ethanol precipitated and resuspended in water. This fragment of DNA is then ligated via the BstXI end to a 250 base pair (bp), PCR-amplified Glycine-Serine coding fragment derived from gene III of M13 bacteriophage DNA. The gene III fragment has been amplified by use of two primers, respectively termed FGSPCR [having the sequence 5'TCGTCTGACCTGCCT-CAACCTCCCCACAATGCTGGCGGCGGCTCTGGT3' (SEQ ID NO: 4)], and RGSPCR [having the sequence 5'ATCAAGTTTGCCTTTACCAGCATTGTG-GAGCGCGTTTTCATC3' (SEQ ID NO:5)], and Taq DNA polymerase (Gibco-BRL). The amplified DNA (250 bp) was cut with BstXI to yield a 200 bp fragment that has been gel purified. The 200 bp fragment is then ligated to the random peptide coding DNA fragment. This DNA specifies the synthesis of a peptide of the sequence Met-His-Cys-(X)$_6$-Cys- (SEQ ID NO:6) fused to the Gly-Ser rich region of the M13 gene III protein. The Gly-Ser rich domain is thought to behave as a flexible linker and assist in presentation of the random peptide to the target molecules.

To make constrained random peptides of different lengths, oligonucleotides are made that are similar to MNN6, except that the degenerate region is 5, 7, 8, and 9 codons long. In addition, oligonucleotides are made that code for various shapes of constrained random peptides by specifying sequences comprising three cysteine residues interspersed between 6–10 randomly specified amino acids.

6.3.2. In Vitro Synthesis and Isolation of Polysomes

An E. coli S30 extract is prepared from the B strain SL119 (Promega). Coupled transcription-translation reactions are performed by mixing the S30 extract with the S30 premix (containing all 20 amino acids), the linear DNA template coding for peptides of random sequences (prepared as described in Section 6.3.1 above), and rifampicin at 20 µg/ml. The reaction is initiated by the addition of 100 units of T7 RNA polymerase and continues at 37° C. for 30 min. The reaction is terminated by placing the reactions on ice and diluting them 4-fold with polysome buffer (20 mM Hepes-NaOH, pH 7.5, 10 mM MgCl$_2$, 1.5 µg/ml chloramphenicol, 100 µg/ml acetylated bovine serum albumin, 1 mM dithiothreitol, 20 units/ml RNasin, and 0.1% Triton X-100). Polysomes are isolated from a 50 µl reaction programmed with 0.5–1 µg of linear DNA template specifying the synthesis of random constrained peptides. To isolate polysomes, the diluted S30 reaction mixtures are centrifuged at 288,000×g for 30–40 min at 4° C. The pellets are suspended in polysome buffer and centrifuged a second time at 10,000×g for 5 min to remove insoluble material.

6.3.3. Affinity Selection/Screening of Polysomes

The isolated polysomes are incubated in microtiter wells coated with the target proteins. Microtiter wells are uniformly coated with 1–5 µg of 6-His tagged, or glutathione S-transferase fused, target proteins (see Section 6.2 hereinabove). Target proteins that are used include the oncoproteins ras and raf, KDR (the vascular endothelial growth factor [vEGF] receptor protein) and vEGF. The microtiter wells are coated with 1–5 µg of these target proteins by incubation in PBS (phosphate-buffered saline; 10 mM sodium phosphate, pH 7.4, 140 mM NaCl, 2.7 mM KCl), for 1–5 hours at 37° C. The wells are then washed with PBS, and the unbound surfaces of the wells blocked by incubation with PBS containing 1% nonfat milk for 1 hr at 37° C. Following a wash with polysome buffer, each well is incubated with polysomes isolated from a single 50 µl reaction for 2–24 hr at 4° C. Each well is washed five times with polysome buffer and the associated mRNA is eluted with polysome buffer containing 20 mM EDTA.

After affinity selection of the polysomes, the associated mRNAs are isolated, and treated with 5–10 units of DNase I (RNase-free; Ambion) for 15 min at 37° C. after addition of MgCl$_2$ to 40 mM. The mRNA is phenol-extracted and ethanol-precipitated and dissolved in 20 µl of RNase-free water. A portion of the mRNA is used for cDNA preparation and subsequent amplification using 15 pmol each of primers RGSPCR [5'ATCAAGTTTGCCTTTACCAGCATTGTG GAGCGCGTTTTCATC3' (SEQ ID NO:5)], and SELEXF1 [5'ACTTCGAAATTAATACGACTCACTATAGGGAGA CCACAACGGTTTCC3' (SEQ ID NO:9)] and rTth Reverse Transcriptase RNA PCR kit (Perkin Elmer Cetus). Specifically, the mRNA is reverse-transcribed into cDNA in a 20 µl reaction containing 1 pg mRNA, 15 pmol of RGSPCR primer, 200 µM each of dGTP, dATP, dTTP, and dCTP, 1 mM MnCl$_2$, 10 mM Tris-HCl, pH 8.3, 90 mM KCl, and 5 units of rTth DNA polymerase at 70° C. for 15 min. In the next step, the cDNA is amplified by the addition of 2.5 mM MgCl$_2$, 8% glycerol, 80 mM-Tris-HCl, pH 8.3, 125 mM KCl, 0.95 mM EGTA, 0.6% Tween 20, and 15 pmol of the SELEXF1 primer. The reaction conditions that are employed are 2 min at 95° C. for one cycle, 1 min at 95° C. and 1 min at 60° C. for 35 cycles, and 7 min at 60° C. for one cycle. The amplified product is then gel-purified and quantitated by spectrophotometry at 260 nm. A portion-of the amplified DNA is digested with NsiI and XbaI and the resulting 30 base pair fragment is directionally cloned into a monovalent phage display vector. The DNAs inserted in the monovalent phage display vector are then sequenced to determine the identity of the peptides that were selectively retained by one cycle of affinity binding to the target protein. A second portion (0.5–1 μg) of the amplified DNA is subjected to another cycle of affinity selection, mRNA isolation, cDNA amplification, and cloning.

6.4. Phagemid Screening

Three different protocols for screening of a phagemid library are presented in the subsections hereinbelow. These protocols, particularly the immobilization and binding steps, are readily adaptable to use for screening of different libraries, e.g., polysome libraries. Preferably, different methods are used in different rounds of screening.

6.4.1. Plate Protocol

In this example, a protocol is presented for screening a phagemid library, in which in the first round of screening, a biotinylated target protein is immobilized (by the specific binding between biotin and streptavidin) on a streptavidin coated plate. The immobilized target protein is then contacted with library members to select binders.

Reagents Used

Purified target protein, microfuge tubes, FALCON 2059, Binding Buffer, Wash Buffer, Elute Buffer, phage display Library of >10$^{11}$ pfu/Screened Target, fresh overnight cultures of appropriate host cells, LB Agar plates with antibiotics as needed, biotinylating agent NHS-LC-Biotin (Pierce Cat. #21335), streptavidin, 50 mM NaHCO$_3$ pH 8.5, 1 M Tris pH 9.1, M280 Sheep anti-mouse IgG coated Dynabeads (Dynal), phosphate buffered saline (PBS), FALCON 1008 petri dishes.

Wash Buffer=1× PBS (Sigma Tablets), 1 mM MgCl$_2$, 1 mM CaCl$_2$, 0.05% Tween 20; (For one liter: 5 PBS tablets, 1 ml 1 M MgCl$_2$, 1 ml 1 M CaCl$_2$, 0.5 ml Tween 20, nanopure H$_2$O to 1 liter).

Binding Buffer=Wash Buffer with 5 mg/ml bovine serum albumin (BSA).

Elute Buffer=0.1 N HCl adjusted to pH-2.2 with glycine: 1 mg/ml BSA.

Procedure

Protein Biotinylation

1. Wash 50–100 μg of target protein in 50 mM NaHCO$_3$ pH 8.5 in a Centricon (Amicon) of the appropriate molecular weight cut-off.
2. Bring the total volume to 100 μl with 50 mM NaHCO$_3$ pH 8.5.
3. Dissolve 1 mg of NHS-LC-Biotin in 1 ml H$_2$O. Do not store this solution.
4. Immediately add 37 μl of the NHS-LC-Biotin solution to the target protein and incubate for 1 hr at room temperature (RT).
5. Remove the unreacted biotin by washing 2× PBS in a Centricon (Amicon) of the appropriate molecular weight cutoff. Store the biotinylated protein at 4° C.

Coating a 1008 Plate with Streptavidin

6. The night before the binding experiment precoat a 1008 plate with streptavidin.
7. Add 10 μg of streptavidin (1 mg/ml H$_2$O) per 1 ml of 50 mM NaHCO$_3$ pH 8.5.
8. Add 1 ml of this solution to each plate and place in a humidified chamber overnight at 4° C.

Prebinding; Blocking Non-Specific Sites

9. To a streptavidin coated plate add 400 μl of Binding Buffer (BSA blocking) for one hour at room temperature.
10. Rinse wells six times with Wash Buffer by slapping dry on a clean piece of labmat.

Binding; Specific Target/Phage Complexes Round 1

11. Add 10 μg of biotinylated target protein in 400 μl of Binding Buffer to the well and incubate for 2 hr at 4° C.
12. Add 4 μl of 10 mM biotin and swirl for 1 hr at 4° C.
13. Wash as in step 10.
14. Add concentrated phage library (>10$^{11}$ pfu) in 400 μl of Binding Buffer and swirl overnight at 4° C.

Washing and Elution

15. Slap out binding mixture and wash as in step 10.
16. To elute bound phage add 400 μl of Elution Buffer and rock at RT for 15 min.
17. Transfer the elution solution to a sterile 1.5 ml tube which contains 75 μl of 1 M Tris pH 9.1. Vortex briefly.

Amplification of Round 1 Eluted Phage

18. Plate all of the eluted round 1 phage by adding 157 μl of phage to 200 μl of cells incubated overnight (previously checked free of contamination) in three aliquots. Incubate 25 min in a 37° C. water bath and then spread onto LB agar/antibiotics plate containing 2% glucose.
19. Scrape plates with 5 ml of 2XYT (growth broth)/Antibiotics/Glucose and leave swirling for 30 min at RT.
20. Add the appropriate amount of 2XYT/Antibiotics/Glucose to bring the O.D. 600 down to 0.4 and then grow at 37° C. at 250 rpm until the O.D. 600 reaches 0.8.
21. Remove 5 ml and add to it 1.25×10$^{10}$ M13 helper phage.
22. Shake 30 min at 150 rpm and then 30 min at 250 rpm at 37° C.
23. Centrifuge 10 min at 3000×g at RT.
24. Resuspend cells in 5 ml 2XYT with no glucose. (This step removes glucose).
25. Centrifuge as in step 23 and resuspend in 5 ml 2XYT with kanamycin and the appropriate antibiotics (no glucose). Spin 18 hr at 37° C. and 250 rpm.
26. Pellet cells at 10,000×g and sterile filter the phage containing supernatant which is now ready for round 2 screening.
27. Titer the round 1 eluted phage stocks.

Binding; Specific Target/Phage Complexes Rounds 2–5

6. Combine ~1 μg of biotinylated target protein with the eluted and titered round 1 phage (10$^9$ pfu) in 200 μl of Binding Buffer and rock 4 hr at 4° C.
7. The night before the round 2 screening is started, prewash 200 μl/target protein to be screened of sheep antimouse IgG magnetic beads (M280 IgG Dynabeads) with 2× 1 ml of Wash Buffer using the Dynal Magnet. Let the beads collect at least 1 min before removing the buffer. Let the beads stand 15 sec to allow residual Binding Buffer to collect and remove with a P200 Pipetman.

8. Resuspend the washed beads in 200 µl of Binding Buffer and add 100 µl of mouse anti-biotin IgG (Jackson IRL). Rock overnight at 4° C.

10. Wash the unbound anti-biotin IgG from the Dynabeads by placing them on the Dyna magnet for at least 1 min and remove all liquid as in Step 7. Remove the tube from the magnet and resuspend the beads in 1 ml of Wash Buffer, rock at 4° C. for 30 min, and return to the magnet. Again let the beads pellet for 1 min; repeat this process 3 more times and resuspend the beads in 400 µl of Binding Buffer.

10a. The coated beads are now ready for use (100 µl/round/target protein). The remainder can be stored for use for up to 2 weeks.

11. Add the 100 µl of anti-biotin coated Dynabeads (Step 10) to the protein/phage fraction (Step 9) bringing the total binding volume to 300 µl and rock for 2 hr at 4° C. Ensure that the beads mix thoroughly with the phage/protein solution.

Washing and Elution

12. Place the binding reaction into the Dynal magnet and let sit for 1 min.

13. Remove the solution using a P1000 Pipetman and discard. Let the beads stand 15 sec to allow residual binding buffer to collect and remove with a P200 Pipetman. Note serial dilution depends upon all residual liquid being removed (i.e., 5 µl into 500 is 100× washing; 50 µl into 500 is only 10×).

14. Remove the tube from the magnet and resuspend the beads in 750 µl of Wash Buffer and return to the magnet. Again let the beads pellet by waiting 1 min.

15. Remove the Wash solution as in Step 7 and repeat this process several more times.

16. After the removal of the final wash, resuspend the beads and transfer them to a fresh, labeled tube and wash once more.

17. To elute bound phage, add 400 µl of Elution Buffer, titrate and rock for 14 min at RT.

18. Place the tube on the magnet for one minute and transfer the eluate to a sterile 1.5 ml tube which contains 75 µl of 1 M Tris pH 9.1. Vortex briefly.

Amplification of Round 2 15 Eluted Phage

15a. Plate 10 µl and 100 µl of round 2,3,4 eluates using 200 µl of contamination free (previously tested) *E. coli* XL1Blue cells onto each plate containing tetracycline/ampicillin/glucose and tetracycline/ampicillin and amplify as in Steps 17–25.

6.4.2. Biotin-Antibiotin IgG Bead Protocol

In this example, a protocol is presented for screening a phagemid library, in which a biotinylated target protein is immobilized (by the specific binding between anti-biotin antibodies and biotin) on a magnetic bead containing anti-biotin antibodies on the bead surface. The immobilized target protein is then contacted with library members to select binders.

Reagents Used

M280 Sheep anti-Mouse IgG coated Dynabeads (Dynal)

Binding; Specific Target/Phage Complexes Round 1

6. Combine 10 µg of biotinylated target protein with the phage library (>$10^{10}$ pfu) in 400 µl of Binding Buffer and rock overnight at 4° C.

7. That same night prewash 50 µl sheep anti-mouse IgG magnetic beads (M280 IgG Dynabeads) with 500 µl of Binding Buffer twice using the Dynal Magnet. Let the beads collect at least 1 min before removing the buffer. Let the beads stand 15 sec to allow residual binding buffer to collect and remove with a P200 Pipetman.

8. Resuspend the washed beads in 100 µl of Binding Buffer and add 33 µl of mouse anti-biotin IgG (40 µg, Jackson IRL). Rock overnight at 4° C.

9. Remove unbound protein from the phage/protein reaction in Step 6 with a Microcon 100. Spin at 800×g until exclusion volume is met and wash twice with Wash Buffer (again at 800×g). Collect phage/protein with a Pipetman and add an additional 50 µl of Wash Buffer to the Microcon, gently titrate and combine with first fraction to ensure maximal recovery.

10. Wash the unbound anti-biotin IgG from the Dynabeads by placing them on the Dyna magnet for at least 1 min and remove all liquid as in Step 7. Remove the tube from the magnet and resuspend the beads in 750 µl of Wash Buffer, rock at 4° C. for 30 min, and return to the magnet. Again, let the beads pellet for 1 min; repeat this process 3 more times and resuspend the beads in 100 µl of Binding Buffer.

11. Add the anti-biotin coated Dynabeads (Step 10) to the protein/phage fraction (Step 9), bring the total binding volume to 500 µl with Binding Buffer, and rock for 2 hr at RT. Ensure that the beads mix thoroughly with the phage/protein solution.

Washing and Elution

12. Place the binding reaction into the Dynal magnet and let sit for 1 min.

13. Remove the solution using a P1000 Pipetman and discard. Let the beads stand 15 sec to allow residual binding buffer to collect and remove with a P200 Pipetman. Note that serial dilution depends upon all residual liquid being removed (i.e., 5 µl into 500 is 100× washing; 50 µl into 500 is only 10×).

14. Remove the tube from the magnet and resuspend the beads in 750 µl of Wash Buffer and return to the magnet. Again let the beads pellet by waiting 1 min.

15. Remove the wash solution as in Step 7 and repeat this process 3 more times.

16. After the removal of the fourth wash, resuspend the beads and transfer them to a fresh, labeled tube and wash once more.

17. To elute bound phage, add 400 µl of Elution Buffer, titrate and rock for 14 min at RT.

18. Place the tube on the magnet for one minute and transfer the eluate to a sterile 1.5 ml tube which contains 75 µl of 1 M Tris pH 9.1. Vortex briefly.

Amplification of Round 1 Eluted Phage

17. Plate all of the eluted round 1 phage by adding 157 µl of phage to 200 ml of cells incubated overnight (previously checked to be free of contamination) in three aliquots. Incubate 25 min in a 37° C. water bath and then spread onto LB agar/antibiotics plate containing 2% glucose. Place plates upright in 37° C. incubator until dry and then invert and incubate overnight.

18. Scrape plates with 5 ml of 2XYT/Antibiotics/Glucose and leave swirling for 30 min at RT.
19. Add the appropriate amount of 2XYT/Antibiotics/Glucose to bring the O.D. 600 down to 0.4 and then grow at 37° C. at 250 rpm until the O.D. 600 reaches 0.8.
20. Remove 5 ml and add to it $1.25 \times 10^{10}$ M13 helper phage.
21. Shake 30 min at 150 rpm and then 30 min at 250 rpm at 37° C.
22. Centrifuge 10 min at 3000×g at RT.
23. Resuspend cells in 5 ml 2XYT with no glucose. (This step removes glucose)
24. Centrifuge as in step 23 and resuspend in 5 ml 2XYT with kanamycin and the appropriate antibiotics (no glucose). Spin 18 hr at 37° C. and 250 rpm.
25. Pellet cells at 10,000×g and sterile filter the phage-containing supernatant which is now ready for round 2 screening.

Binding; Specific Target/Phage Complexes Round 2, 3, & 4

6a. Bind 1 μg of target protein with 100 μl of amplified phage from the previous round as before, overnight at 4° C.
7a. Prepare the IgG anti biotin/anti IgG beads as in Steps 7–10 using, however, only 20 μl of sheep anti-mouse IgG and 13 μl of anti-biotin IgG.
8a. All other binding procedures are identical with Steps 6–11.

Washing and Elution

9a. Place the binding reaction into the Dynal magnet and let sit for 1 min.
19a. Remove the solution and discard using a P1000 Pipetman. Let the beads stand 30 sec to allow residual Binding Buffer to collect and remove with a P200 Pipetman.
11a. Remove the tube from the magnet and resuspend the beads in 750 μl of Wash Buffer and return to the magnet. Again let the beads pellet by waiting 1 min.
12a. Remove the wash solution as in Step 11a and repeat this process 3 more times.
13a. After the removal of the fourth wash, resuspend the beads and transfer them to a fresh, labeled tube and wash 4 more times.
14a. Elute and neutralize as in Step 15.

Amplification of Rounds 2, 3, & 4 Eluted Phage

15a. Plate 10 μl and 100 μl of round 2,3,4 eluates and amplify as in Steps 17–25.

6.4.3. Biotin-Streptavidin, Magnetic Bead Protocols

In this example, a protocol is presented for screening a phagemid library, in which a biotinylated target protein is immobilized (by the specific binding between biotin and streptavidin) on a streptavidin coated magnetic bead. The immobilized target protein is then contacted with library members to select binders.

Reagents Used

Purified target protein, M280 streptavidin coated Dynabeads (Dynal)

Binding; Specific Target/Phage Complexes Round 1

6. Combine 10 μg of biotinylated target protein with the phage library ($>10^{10}$ pfu) in 400 μl of Binding Buffer and rock overnight at 4° C.

7. Remove unbound protein with a Microcon 100. Spin at 800×g until exclusion volume is met, and wash twice with Wash Buffer (again at 800×g). Collect phage/protein with a Pipetman and add an addition 50 μl of Wash Buffer to the Microcon, gently titrate and combine with the first fraction to ensure maximal recovery.
8. Prewash 50 μl (per reaction) of streptavidin magnetic beads (M280 streptavidin Dynabeads) twice with 500 μl of Washing Buffer using the Dynal magnet.
9. Add the prewashed Dynabeads to the protein/phage fraction (add Binding Buffer to a total of 500 μl) and rock for 30 min. Ensure that the beads mix thoroughly with the phage/protein solution.

Washing and Elution

10. Place the binding reaction into the Dynal magnet and let sit for 1 min.
11. Remove the solution using a P1000 Pipetman and discard. Let the beads stand 15 sec to allow residual Binding Buffer to collect and remove with a P200 Pipetman. Note that serial dilution depends upon all residual liquid being removed (i.e., 5 μl into 500 is 100× washing; 50 μl into 500 is only 10×).
12. Remove the tube from the magnet and resuspend the beads in 750 μl of Wash Buffer and return to the magnet. Again let the beads pellet by waiting 1 min.
13. Remove the wash solution as in step 11 and repeat this process 3 more times.
14. After the removal of the fourth wash, resuspend the beads and transfer them to a fresh, labeled tube and wash once more.
15. To elute bound phage add 400 μl of Elution Buffer, titrate and rock for 14 min at RT.
16. Place the tube on the magnet for one minute and transfer the eluate to a sterile 1.5 ml tube which contains 75 μl of 1 M Tris pH 9.1. Vortex briefly.

Amplification of Round 1 Eluted Phage

17. Plate all of the eluted round 1 phage by adding 157 μl of phage to 200 μl of overnight cells (previously checked to be free of contamination) in three aliquots. Incubate 25 min in a 37° C. water bath and then spread onto LB agar/antibiotics plate containing 2% glucose. Place plates upright in 37° C. incubator until dry and then invert and incubate overnight.
18. Scrape plates with 5 μl of 2XYT/Antibiotics/Glucose and leave swirling for 30 min at RT.
19. Add the appropriate amount of 2XYT/Antibiotics/Glucose to bring the O.D. 600 down to 0.4 and then grow at 37° C. at 250 rpm until the O.D. 600 reaches 0.8.
20. Remove 5 ml and add to it $1.25 \times 10^{10}$ M13 helper phage.
21. Shake 30 min at 150 rpm and then 30 min at 250 rpm at 37° C.
22. Centrifuge 10 min at 3000×g at RT.
23. Resuspend cells in 5 μl 2XYT with no glucose. (This step removes glucose).
24. Centrifuge as in step 22 and resuspend in 5 ml 2XYT with kanamycin and the appropriate antibiotics (no glucose). Shake 18 hr at 37° C. and 250 rpm.
25. Pellet cells at 10,000×g and sterile filter the phage containing supernatant which is now ready for round 2 screening.

Binding; Specific Target/Phage Complexes Round 2, 3, & 4

6a. Combine 1 μg of biotinylated target protein with 100 μl of the previous round's phage (>10⁹ pfu) in 400 μl of Binding Buffer and rock overnight at 4° C.

7a. Remove unbound protein with a Microcon 100. Spin at 800×g until exclusion volume is met and wash twice with Wash Buffer (again at 800×g). Collect phage/protein with a Pipetman and add an addition 50 μl of Wash Buffer to the Microcon, gently titrate and combine with the first fraction to ensure maximal recovery.

8a. Prewash 20 μl (per reaction) of streptavidin magnetic beads (M280 streptavidin Dynabeads) twice with 500 μl of Washing Buffer using the Dynal magnet.

9a. Add the prewashed Dynabeads to the protein/phage fraction and rock for 30 min. Add Binding Buffer to a total of 500 μl. Ensure that the beads mix thoroughly with the phage/protein solution.

Washing and Elution

10a. Place the binding reaction into the Dynal magnet and let sit for 1 min.

11a. Remove the solution and discard using a P1000 Pipetman. Let the beads stand 30 sec to allow residual Binding Buffer to collect and remove with a P200 Pipetman.

12a. Remove the tube from the magnet and resuspend the beads in 750 μl of Wash Buffer and return to the magnet. Again let the beads pellet by waiting 1 min.

13a. Remove the wash solution as in Step 11a and repeat this process 3 more times.

14a. After the removal of the fourth wash resuspend the beads and transfer them to a fresh, labeled tube and wash 4 more times.

15a. Elute and neutralize as in Step 15.

Amplification of Rounds 2, 3, & 4 Eluted Phage

16a. Plate 10 μl and 100 μl of round 2,3,4 eluates and amplify as in Steps 17–25.

6.5. Affinity Measurements of Peptide-Target Protein Interactions

Once peptides that bind to a target protein have been identified, the affinities of these peptides to their respective targets are measured by measuring the dissociation constants ($K_d$) of each of these peptides to their respective targets. Oligonucleotides that encode the peptides are constructed so as to encode also an epitope tag fused to the peptide (for example, the myc epitope) that can be detected by a commercially available antibody. These oligonucleotides are incubated with polysome extracts to produce the peptide tagged with the epitope. Binding of the target protein to the peptide is done in solution, and separation of the bound peptide from the unbound peptide is done by immunoaffinity purification using an anti-target protein antibody. This immunoaffinity purification is done by a modified ELISA (enzyme-linked immunosorbent assay) protocol, in which the target protein-peptide mixture is exposed to the anti-target protein antibody immobilized on a solid support such as a nitrocellulose membrane, and the unbound peptide is then washed off. In this protocol, the concentration of the target protein is varied and then the amount of bound peptide is estimated by detecting the epitope tag on the peptide by use of anti-epitope antibody. In this manner, the affinity of each peptide for its target protein can be determined.

6.6. Redor Measurements on a $CX_6C$ Peptide Resin

This example demonstrates successful synthesis and cyclization of a $CX_6C$ peptide resin of greater than 95% purity and with a labeled glycine followed by successful REDOR distance measurements on the $CX_6C$ peptide resin using the preferred REDOR methods of this invention. The labeled peptide used was Cys-Asn-Thr-Leu-Lys-($^{15}$N-2-$^{13}$C)Gly-Asp-Cys-Gly-mBHA resin, where a glycine linker attached the peptide of interest to the nBHA resin. (Cys-Asn-Thr-Leu-Lys-Gly-Asp-Cys-Gly=SEQ ID NO:10)

The peptide resin was synthesized by solid phase synthesis on p-MethylBenzhydrilamine (mBHA) resin using a combination of Boc and Fmoc chemistry. MethylBenzhydrilamine resin (Subst. 0.36 meq/g) was purchased from Advanced Chem Tech (Louisville, Ky.). Fmoc($^{15}$N-2-$^{13}$C)Gly was prepared from HCl, ($^{15}$N-2-$^{13}$C)Gly (Isotec Inc., Miamisburg, Ohio) and Fmoc-OSu. Boc-Gly, (Trt), Fmoc-Asp(OtBu), Fmoc-Lys(Boc), Fmoc-Leu, Fmoc-Thr(OtBu), Fmoc-Asn and Boc-Cys(Acm) were purchased from Bachem (Torrance, Calif.). Reagent grade solvents were purchased from Fisher Scientific, Diisopropylcarbodiimide (DIC), Trifluoroacetic acid (TFA) and Diisopropylethylamine (DIEA) were purchased from Chem Impex (Wooddale, Ill.). Nitrogen, HF were purchased from Air Products (San Diego, Calif.).

The first step 43 was the synthesis of Boc-Cys(ACM)-Asn-Thr(OtBu)-Leu-Lys(Boc)-Gly-Asp(OtBu)Cys(Trt)-Gly-mBHA resin. 1.11 g (0.40 meq) of mBHA resin were placed in a 150 ml reaction vessel (glass filter at the bottom) with Methylene Chloride ($CH_2Cl_2$) ["DCM"] and stirred 15 min with a gentle bubbling of Nitrogen in order to swell the resin. The solvent was drained and the resin was neutralized with DIEA 5% in DCM (3×2 min). After washes with DCM, the resin was coupled 60 min with Boc-Gly (0.280 g-1.6 meq-4 fold excess-0.1 M) and DIC (0.25 ml-1.6 meq-4 fold excess-0.1 M) in DCM. Completion of the coupling was checked with the Ninhydrin test. After washes, the resin was stirred 30 min in TFA 55% in DCM in order to remove the Boc protecting group. The resin was then neutralized with DIEA 5% in DCM and coupled with Fmoc-Cys(Trt)(0.937 g-1.6 meq-4 fold excess-0.1 M) and DIC (0.25 ml-1.6 meq-4 fold excess-0.1 M) in DCM/DMF (50/50). After washes the resin was stirred with Piperidine 20% in DMF (5 min and 20 min) in order to remove the Fmoc group. After washes, this same cycle was repeated with Fmoc-Asp(OtBu), Fmoc($^{15}$N-2-$^{13}$C)Gly (2 fold excess only), Fmoc-Lys(Boc), Fmoc-Leu, Fmoc-Thr(OtBu), Fmoc-Asn and Boc-Cys(Acm). After the last coupling, the Boc group was left on the peptide. The resin was washed thoroughly with DCM and dried under a nitrogen stream. Yield was 1.49 g (Expected: ~1.7 g).

The next step 44 was cyclization of the Boc-Cys-Asn-Thr(OtBu)-Leu-Lys(Boc)-Gly-Asp(OtBu)-Cys-Gly-mBHA resin. 600 mg of protected peptide resin were sealed in a polypropylene mesh packet. The bag was shaken in a mixture of solvent (DCM/Methanol/Water-640/280/47) in order to swell the resin. The bag was then shaken 20 min in 100 ml of a solution of iodine in the same mixture of solvent (0.4 mg $I_2$/ml solvent mixture). This operation was performed 4 times. No decoloration was observed after the third time. The resin was then thoroughly washed with DCM, DMF, DCM, and methanol successively.

The last step 45 was side-chain deprotection of the Cys-Asn-Thr-Leu-Lys-Gly-Asp-Cys-Gly-mBHA resin. After cyclization the resin in the polypropylene bag was reacted 1.5 hour with 100 ml of a mixture TFA/p-Cresol-Water (95/2.5/2.5). After washes with DCM and Methanol, the resin was dried 48 hours under vacuum. Yield was 560 mg.

The resulting peptide resin was analyzed for its purity and the presence of the disulfide bridge. 40 mg of resin were sealed in a propylene mesh packet and treated with HF at 0 C for 1 hour in presence of anisole (HF/Anisole: 90/10). The scavenger and by-products were extracted from the resin with cold ethyl ether. The peptide was extracted with 10% Acetic Acid and lyophilized 36 hours. The dry isolated peptide was characterized by PDMS (mass spectrography) and HPLC (high performance liquid chromatography). This analysis demonstrated that greater than 95% of the product peptide was of the correct amino acid composition, having a disulfide loop and without inter-molecular disulfide dimers.

Figure 6:
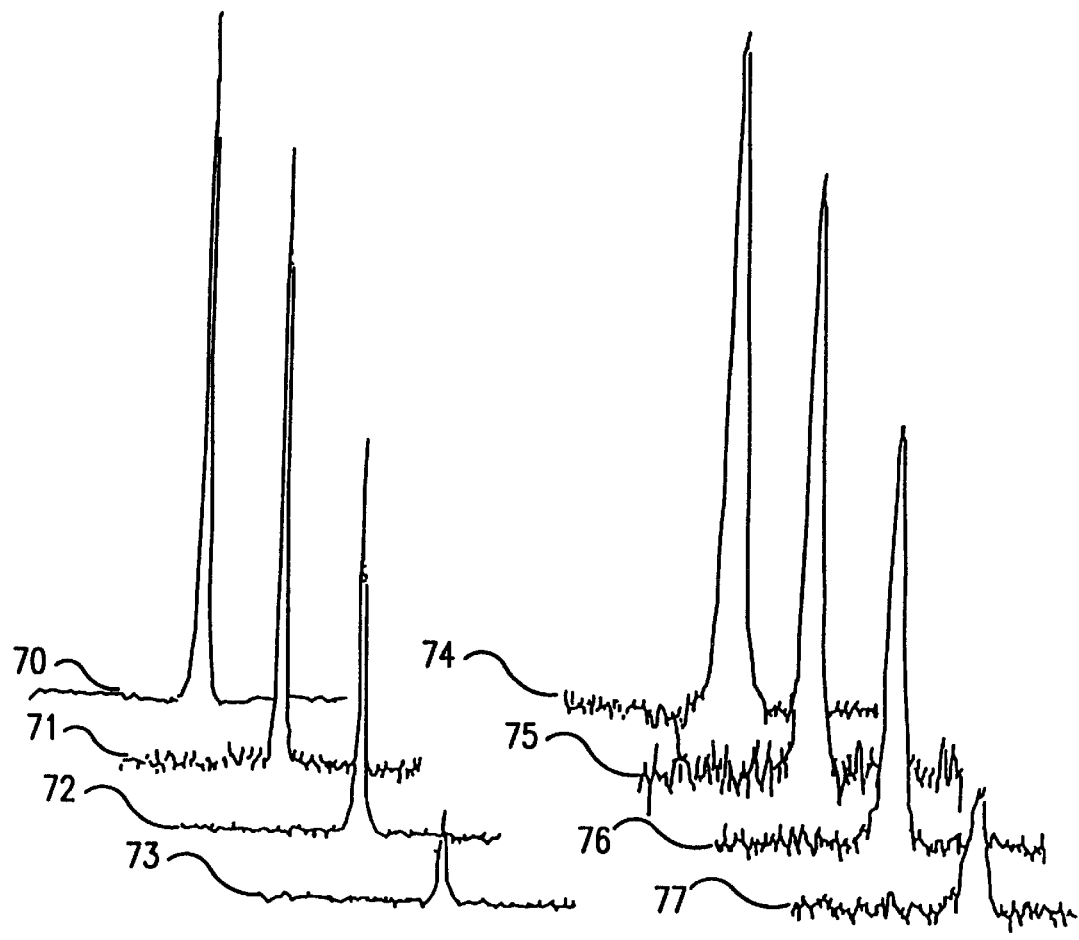
FIG. 6 is sample REDOR NMR spectra according to the method of FIG. 3.

REDOR measurements were made on the peptide resin prepared by this method, and as a control, also on dried ($^{15}$N-2-$^{13}$C) labeled glycine. The preferred REDOR methods and parameters, as previously detailed, were used. FIG. 6 illustrates the $^{15}$N resonance spectral signals obtained. Signal 70 is the signal produced by dried glycine after no rotor periods. Signals 71, 72, 73 are glycine signals after 2, 4, and 8 rotor periods, respectively. Signals 74, 75, 76, and 77 are the peptide resin signals after 0, 2, 4, and 8 rotor periods, respectively.

Figure 7:
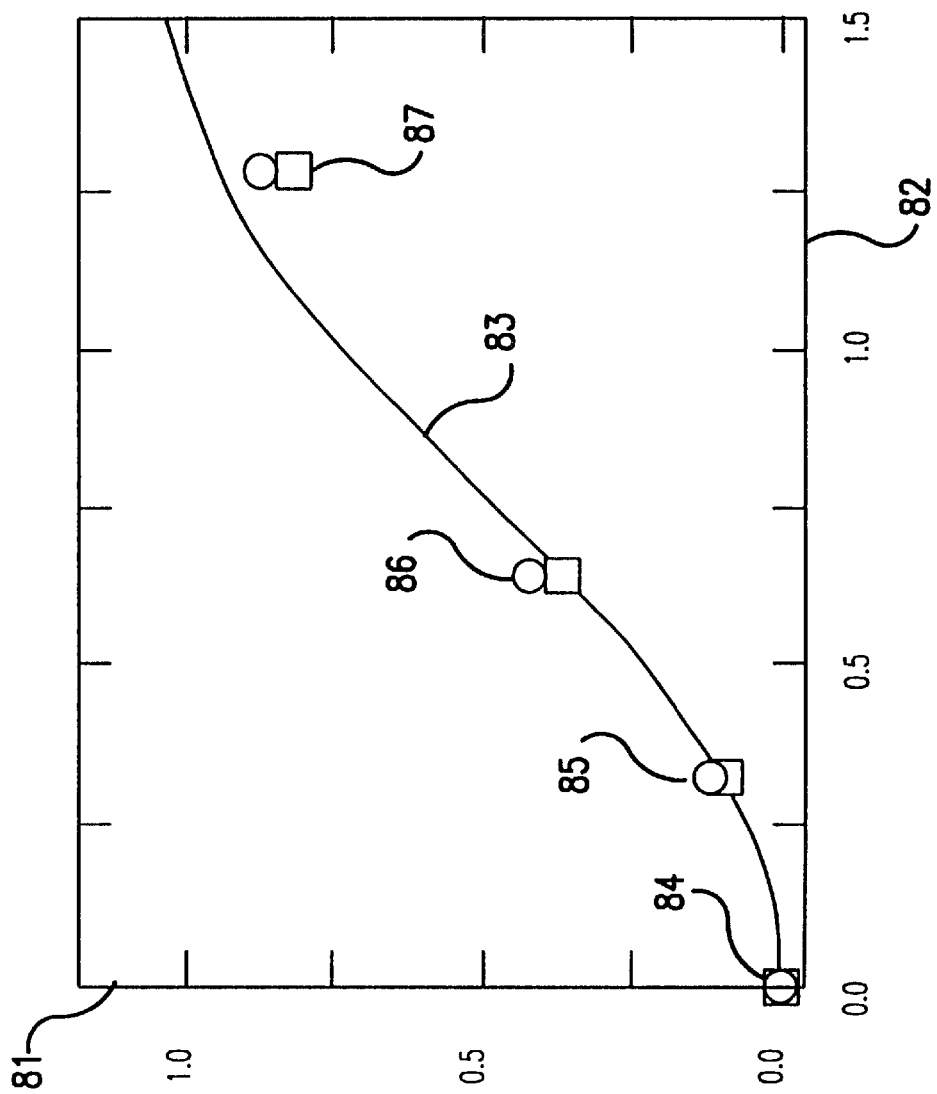
FIG. 7 is sample data analysis according to the method of FIG. 3.

FIG. 7 illustrates the data analysis. As in FIG. 5, axis 81 is the ΔS/S axis, and axis 82 is the λ axis. The variables are as used in equation 5. Graph 83 is defined by equation 5, and is the initial rising part of the full curve shown in FIG. 5. Data points 84, 85, 86, and 87 are best fits of the data for 0, 2, 4, and 8 rotor periods, respectively. At these points, the circles represent the glycine values and the squares the peptide resin values. These values correspond to a C-N distance in glycine and the peptide of 1.55 Å (and a DN of 800 Hz). Repeated measurements gave a C-N distance of 1.50 Å (and a $D_{CN}$ of 875 Hz). The accepted distance in glycine is 1.48 Å. The above procedure was repeated for ($^{15}$N-1-$^{13}$C) labeled glycine in Cys-Asn-Thr-Leu-Lys-($^{15}$N-1-$^{13}$C)Gly-Asp-Cys-Gly-mBHA resin, and the measured C-N distance of 2.50 Å is in excellent agreement with the predicted value of 2.46 Å.

Thus REDOR accuracy to better that 0.1 Å is demonstrated. Also demonstrated is the peptide resin as an appropriate substrate for NMR measurements. Inter-molecular dipole-dipole interactions between adjacent peptides did not interfere. Also the overlap of the distances measured in free glycine and in glycine incorporated in the peptide demonstrated that the peptide was held sufficiently rigidly by the resin that any remaining peptide motions did not interfere with the NMR measurements.

7. Specific Embodiments, Citation of References

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

---

What is claimed is:

1. A method for measuring one or more interatomic distances of a binder compound comprising measuring internuclear dipole-dipole interaction strengths between selected nuclei in a sample of the binder compound by means of solid state nuclear magnetic resonance, wherein:

(i) said binder compound binds to a target compound, and (ii) said sample of the binder compound covalently is attached to the surface of a substrate during said step of measuring internuclear dipole-dipole interaction strengths, said substrate being different from said sample.

2. The method of claim 1, wherein the solid state nuclear magnetic resonance measurements are made by means of REDOR NMR.

3. The method of claim 1, wherein the method further comprises attaching a plurality of molecules of the binder compound to the surface of the substrate.

4. The method of claim 3, wherein the plurality of molecules is synthesized directly on the surface of the substrate.

5. The method of claim 3, wherein the step of attaching a plurality of molecules of the binder compound to the surface of the substrate comprises:

(a) synthesizing a plurality of molecules of the binder compound on a first solid phase substrate;

(b) cleaving the plurality of molecules of the binder compound from the first solid phase substrate;

(c) purifying the plurality of molecules of the binder compound; and (d) attaching the plurality of molecules of the binder compound to a second substrate.

6. The method of claim 1, wherein the sample of the binder compound is attached to the surface of the substrate by means of:

(a) condensation of a free carboxyl terminal group on the binder compound with an amino labeled resin of the substrate surface; or (b) a heterofunctional linker group.

7. The method of claim 1, wherein the substrate is selected from the group consisting of p-methylbenzyhydrilamine resin, divinylbenzyl polystyrene resin, and a glass bead.

8. The method of claim 1, wherein the surface density of molecules of the binder compound on the substrate is such that the internuclear dipole-dipole interaction strength between nuclei in different molecules of the binder compound is less than 10% of the internuclear dipole-dipole interaction strength between nuclei in the same molecule of the binder compound.

9. The method of claim 8, wherein adjacent molecules of the binder compound on the surface of the substrate are separated by approximately 2 to 3 times the distance to be measured.

10. The method of claim 1, wherein the density of molecules of the binder compound in the sample is no less than 0.0017 mmole/g.

11. The method of claim 10, wherein the density of molecules of the binder compound in the sample is no less than 0.017 mmole/g.

12. The method of claim 1, wherein the binder compound is bound to the target compound during said step of measuring internuclear dipole-dipole interaction strengths.

13. The method of claim 12, wherein the substrate has pores of sufficient size to permit a molecule of the target compound to diffuse and bind to a molecule of the binder compound.

14. The method of claim 1, wherein the binder compound is a peptide, a peptide derivative, or a peptide analogue, having a constrained conformation.

15. The method of claim 14, wherein the peptide, peptide derivative, or peptide analogue is constrained by internal bonds.

16. The method of claim 15, wherein the internal bonds are disulfide bonds.

17. The method of claim 16, wherein the peptide, peptide derivative, or peptide analogue contains a pair of cysteine residues.

18. The method of claim 17, wherein the cysteine residues are separated by 2 to 16 amino acid residues.

19. The method of claim 18, wherein the cysteine residues are separated by 6 to 8 amino acid residues.

20. The method of claim 14, wherein the peptide, peptide derivative, or peptide analogue is of the form $R^1CX_nCR^2$, wherein:

$R^1$ is a first sequence of 0 to 10 amino acid residues;

$R^2$ is a second sequence of 0 to 10 amino acid residues;

$X_n$ is a sequence of n amino acid residues; and n is an integer ranging from 2 to 16.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 8 amino acids
      (B) TYPE: amino acid
      (D) TOPOLOGY: unknown (ii) MOLECULE TYPE: peptide (ix) FEATURE:
      (A) NAME/KEY: Disulfide-bond
      (B) LOCATION: 1..8
      (D) OTHER INFORMATION: /note= "A disulfide bond is formed
          between the cysteine residues."

(xi) SEQUENCE DESCRIPTION: SEQ ID NO:1:

Cys Xaa Xaa Xaa Xaa Xaa Xaa Cys
1               5

(2) INFORMATION FOR SEQ ID NO:2:

(i) SEQUENCE CHARACTERISTICS:
      (A) LENGTH: 102 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:2:

```
ACTTCGAAAT TAATACGACT CACTATAGGG AGACCACAAC GGTTTCCCTC CAGAAATAAT        60

TTTGTTTAAC TTTAACTTTA AGAAGGAGAT ATACATATGC AT                         102
```

(2) INFORMATION FOR SEQ ID NO:3:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

```
CCCAGACCCG CCCCCAGCAT TGTGGGTTCC AACGCCCTCT AGACAMNNMN NMNNMNNMNN        60

MNNACAATGT ATATCTCCTT CTT                                              83
```

(2) INFORMATION FOR SEQ ID NO:4:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

```
TCGTCTGACC TGCCTCAACC TCCCCACAAT GCTGGCGGCG GCTCTGGT                    48
```

(2) INFORMATION FOR SEQ ID NO:5:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

```
ATCAAGTTTG CCTTTACCAG CATTGTGGAG CGCGTTTTCA TC                          42
```

(2) INFORMATION FOR SEQ ID NO:6:

(i) SEQUENCE CHARACTERISTICS:
        (A) LENGTH: 10 amino acids
        (B) TYPE: amino acid
        (D) TOPOLOGY: unknown (ii) MOLECULE TYPE: peptide (xi) SEQUENCE DESCRIPTION: SEQ ID NO:6:

```
Met His Cys Xaa Xaa Xaa Xaa Xaa Xaa Cys
1               5                   10
```

(2) INFORMATION FOR SEQ ID NO:7:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (xi) SEQUENCE DESCRIPTION: SEQ ID NO:7:

```
Cys Gly Gly Gly Gly Gly Gly Cys
```

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:8:

NNKNNKNNKN NKNNKNNKNN KNNKNNKNNK                    30

(2) INFORMATION FOR SEQ ID NO:9:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

ACTTCGAAAT TAATACGACT CACTATAGGG AGACCACAAC GGTTTCC        47

(2) INFORMATION FOR SEQ ID NO:10:

(i) SEQUENCE CHARACTERISTICS:
        (A) LENGTH: 9 amino acids
        (B) TYPE: amino acid
        (D) TOPOLOGY: unknown (ii) MOLECULE TYPE: peptide (xi) SEQUENCE DESCRIPTION: SEQ ID NO:10:

Cys Asn Thr Leu Lys Gly Asp Cys Gly
1          5

(2) INFORMATION FOR SEQ ID NO:11:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 2...3
        (D) OTHER INFORMATION: Xaa=any amino acid
        (A) NAME/KEY: Other
        (B) LOCATION: 4...11
        (D) OTHER INFORMATION: Xaa=any amino acid and may
            or may not be present
        (A) NAME/KEY: Other
        (B) LOCATION: 13...14
        (D) OTHER INFORMATION: Xaa=any amino acid
        (A) NAME/KEY: Other
        (B) LOCATION: 15...22
        (D) OTHER INFORMATION: Xaa=any amino acid and may
            or may not be present (xi) SEQUENCE DESCRIPTION: SEQ ID NO:11:

Cys Xaa Xaa Xaa Xaa Xaa Xaa Xaa Xaa Xaa Xaa Cys Xaa Xaa Xaa Xaa
1          5                10             15

```
-continued

Xaa Xaa Xaa Xaa Xaa Xaa Cys Cys
            20
```